US007067624B2

(12) United States Patent
Manners et al.

(10) Patent No.: US 7,067,624 B2
(45) Date of Patent: *Jun. 27, 2006

(54) ANTIMICROBIAL PROTEINS

(75) Inventors: John Michael Manners, Paddington (AU); John Paul Marcus, Corinda (AU); Kenneth Clifford Goulter, Jamboree Heights (AU); Jodie Lyn Green, Jamboree Heights (AU); Neil Ivan Bower, Kenmore (AU)

(73) Assignees: Commonwealth Scientific and Industrial Research Organisation, Australian Capital Territory (AU); The State of Queensland Department of Primary Industries, Queensland (AU); The University of Queensland, Queensland (AU); Bureau of Sugar Experiment Stations, Queensland (AU); Queensland University of Technology, Queensland (AU)

( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/331,631

(22) PCT Filed: Dec. 22, 1997

(86) PCT No.: PCT/AU97/00874

§ 371 (c)(1),
(2), (4) Date: Jun. 21, 1999

(87) PCT Pub. No.: WO98/27805

PCT Pub. Date: Jul. 2, 1998

(65) Prior Publication Data

US 2002/0168392 A1 Nov. 14, 2002

(30) Foreign Application Priority Data

Dec. 20, 1996 (AU) .................................... PO4275

(51) Int. Cl.
*C07K 1/00* (2006.01)

(52) U.S. Cl. ...................... 530/350; 530/300; 530/350; 530/370; 530/377; 435/6; 435/69.1; 435/320.1; 435/252.33; 435/172.3; 536/23.6; 536/23.2

(58) Field of Classification Search .................... 435/6, 435/9.1, 320.1, 172.3, 252.33, 240.1; 536/23.2, 536/23.6; 530/350, 300, 370, 377; 800/205, 800/DIG. 56; 426/534
See application file for complete search history.

(56) References Cited

U.S. PATENT DOCUMENTS

| | | | | | |
|---|---|---|---|---|---|
| 5,422,265 | A | * | 6/1995 | Civelli et al. | 435/252.3 |
| 5,468,615 | A | * | 11/1995 | Chio et al. | 435/7.2 |
| 5,770,433 | A | * | 6/1998 | Spencer et al. | 435/252.33 |
| 5,905,187 | A | * | 5/1999 | Duvick et al. | 800/205 |

FOREIGN PATENT DOCUMENTS

| | | | |
|---|---|---|---|
| EP | 093652 | * | 11/1996 |
| WO | WO 91/19801 | | 12/1991 |
| WO | WO91/19801 A | * | 12/1991 |
| WO | WO 96/13585 | * | 5/1996 |

OTHER PUBLICATIONS

Alignments.*

Chlan et al. *Development Biochemistry of Cottonseed Embryogenesis and Germination XIX.*, Plant Molecular Biology 9:533-546 (1987).

McHenry et al. *Comparison of the Structure and Nucleotide Sequences to Vicilin Genes of Cocoa and Cotton*, Plant Molecular Biology 18:1173-1176 (1992).

Belanger et al. *Molecular Basis for Allelic Plymorphism of the Maize Globulin-1 Gene*, Genetics Society of America, 129: 865-872 (Nov., 1991).

Alan L. Kriz, *Characterization of Embryo Globulins Encoded by the Maize Gib Genes*, Biochemical Genetics, al. 27, Nos. 3/4, (1989).

Heck et al., *Barley Embryo Globulin 1 Gene, Beg1: Characterization of Cdna*, Mol. Gen. Genet. 239: 209-218 (1993).

Burks et al., *Recombinant Peanut Allergen Ara h l Expression and IgE Binding in Patients with Peanut Hypersensitivity*, vol. 96, 1715-1721, Oct. 1995.

Sebastiani et al., *Complete Sequence of a Cdna of a subunit of soybean β-conglycinin*, Plant Molecular Biology, 15: 197-201, (1990).

Chlan et al., *Developmental Biochemistry of Cottonseed Embryogenesis and Germination XVIII cDNA*, Plant Molecular Biology 7:475-489, (1986).

* cited by examiner

*Primary Examiner*—Kathleen M. Kerr
*Assistant Examiner*—Hope Robinson
(74) *Attorney, Agent, or Firm*—Knobbe, Martens, Olson & Bear, LLP

(57) ABSTRACT

A new family of antimicrobial proteins is described. Prototype proteins can be isolated from *Macadamia integrifolia* as well as other plant species. DNA encoding the protein is also described as well as DNA constructs which can be used to express the antimicrobial protein or to introduce the antimicrobial protein into a plant. Compositions comprising the antimicrobial protein or the antimicrobial protein per se can be administered to plants or mammalian animals to combat microbial infestation.

23 Claims, 21 Drawing Sheets

| | | | |
|---|---|---|---|
| Mi2a | 1 | SEFDRQEYEECKRQCMQLE-TSG-QMRRCVSQCD | 32 |
| Mi2b | 1 | NQEDPQTECQQCQRRCRQQE-SGPRQQQYCQRRCK | 34 |
| Mi2c | 1 | NRQRDPQQQYEQCQKHCQRRE-TEPRHMQTCQQRCE | 35 |
| Mi2d | 1 | KRDPQQREYEDCRRRCEQQE---PRQQHQCQLRCR | 32 |
| Cocoa-a | 1 | YERDPRQQYEQCQRRCESEA-TEEREQEQCEQRCE | 34 |
| Cocoa-b | 1 | LQRQYQQCQGRCQEQQ-QGQREQQQCQRKCW | 30 |
| Cotton-a | 1 | GDDDPPKRYEDCRRRCEWDT-RGQKEQQQCEESCK | 34 |
| Cotton-b | 1 | PEDPQRRYEECQQECRQQE---ERQQPQCQQRCL | 31 |
| Cotton-c | 1 | SQRQFQECQQHCHQQE-QRPEKKQQCVRECR | 30 |
| maize glb1_0 fr | 1 | EDDNHHHHGGHKSGRCVRRCEDR---PWHQRPRCLEQCR | 36 |
| barley glob fra | 1 | HDDEDDRRGGHSLQQCVQRCRQER--PRYSHARCVQECR | 37 |
| Peanut-a | 1 | TENP--CAQRCLQSCQQE--PDDLKQKACESRCT | 30 |
| alpha conglycin | 1 | ENP--KHNKCLQSCNSER--DSYRNQACHARCN | 29 |
| SsAMP1 partial | 1 | VKEDHQFETRGEILECYRLCQQQ | 23 |
| SsAMP2 partial | 1 | QKHRSQILGCYLXCQQL | 17 |
| SsAMP3 partial | 1 | LDPIRQQQLCQMRCQQQEKD-PRQQQQCK | 28 |

Fig. 4

| | | | |
|---|---|---|---|
| Mi2a | 33 | KR**F**EEDIDWSKYD | 45 |
| Mi2b | 35 | EI**CEEEEE**Y | 43 |
| Mi2c | 36 | RR**Y**EKEKRKQQKRYEEQQREDEEKYEERMK**EED**N | 69 |
| Mi2d | 33 | EQQRQHGRGGDMMNPQRGGSGRY**EE**G**EEE**QS | 63 |
| Cocoa-a | 35 | RE**Y**KEQQRQQ**EEE** | 47 |
| Cocoa-b | 31 | EQ**Y**KEQERGEHENYHNHKKNRS**EEEE**GQQR | 60 |
| Cotton-a | 35 | SQ**Y**GEKDQQQRHR | 47 |
| Cotton-b | 32 | KR**F**EQEQQQ | 40 |
| Cotton-c | 31 | EK**Y**QENPWRGER | 42 |
| maize glb1 | 37 | EEEREKRQERSRHEADDRSGEGSS | 60 |
| barley glob | 38 | DDQQQHGRHEQEEEQGRGRGWHGEG**E**R**EE** | 66 |
| Peanut-a | 31 | KLEYDPR**C**VYDTGATNQRHPPGERT--RGRQP | 60 |
| alpha conglycin | 30 | LLKVEKEE**C**EEGEIPRPRPRPQHPER | 55 |
| SsAMP1 partial | 23 | | 23 |
| SsAMP2 partial | 17 | | 17 |
| SsAMP3 partial | 28 | | 28 |

Fig. 4 (continued)

```
AACTCTAGAG CGGCCGCGTC GACTATTTTT ACAACAATTA CCAACAACAA CAAACAACAA 60

ACAACATTAC AATTACTATT TACAATTACA GGATCCACAA CAATGGCTTG GTTCCACGTT 120
                                              M  A  W   F  H  V>

TCTGTTTGTA ACGCTGTTTT CGTTGTTATT ATTATTATTA TGCTTCTTAT GTTCGTTCCT 180
 S  V  C   N  A  V  F   V  V  I   I  I  I  M  L  L  M   F  V  P>

GTTGTTAGAG GTAGACAAAG AGATCCTCAA CAACAATACG AGCAATGTCA AAAGAGGTGT 210
 V  V  R   G  R  Q  R   D  P  Q   Q  Q  Y  E  Q  C  Q   K  R  C>

CAAAGGAGAG AGACTGAGCC TAGACACATG CAAATTTGTC AGCAAAGGTG TGAAAGGAGG 240
 Q  R  R   E  T  E  P   R  H  M   Q  I  C  Q  Q  R  C   E  R  R>

TACGAGAAGG AGAAGAGGAA GCAACAAAAG AGGTGAGGAT CCGTCGACGC GGCCGCAGAT 270
 Y  E  K   E  K  R  K   Q  Q  K   R  *

CTAGACAA 278
```

Fig. 5

```
Mi clone 1      1  MAINTSNLCSLLFLLSL-FLLSTTVSLAE----SEFDRQEYEE  38
Mi clone 2      1  MAINTSNLCSLLFLLSL-FLLSTTVSLAE----SEFDRQEYEE  38
Mi clone 3      0                                                0
cotton vicilin  1  MVRNKSACVVLLFSLFLSFGLLCSAKDFPGRRGDD--------  35
cocoa vicilin   1  MVISKSPFIVLIFSLLLSFALLCSGVSAYGRKQYER-------  36
                   *. . *    *.* * * *.*  ..  .

Mi clone 1     39 CKRQCMQLETSGQMRRCVSQCDKRFEEDIDWSKYDNQEDPQTECQ  83
Mi clone 2     39 CKRQCMQLETSGQMRRCVSQCDKRFEEDIDWSKYDNQdDPQTdCQ  83
Mi clone 3     42    QCMQLETSGQMRRCVSQCDKRFEEDIDWSKYDNQEDPQTECQ  83
cotton vicilin 36 --------------------------------------DPPKRYE  42
cocoa vicilin  37 --------------------------------------DPRQQYE  43
                                                      **     .

Mi clone 1     84 QCQRRCRQQESGPRQQQYCQRRCKEICEEEEEYNRQR--DPQQQY 126
Mi clone 2     84 QCQRRCRQQESGPRQQQYCQRRCKEICEEEEEYNRQR--DPQQQY 126
Mi clone 3     84 QCQRRCRQQESdPRQQQYCQRRCKEICEEEEEYNRQR--DPQQQY 126
cotton vicilin 43 DCRRRCEWDTRGQKEQQQCEESCKSQYGEKDQQQRHRPEDPQRRY  87
cocoa vicilin  44 QCQRRCESEATEEREQEQCEQRCEREYKEQQRQQ---EEELQRQY  85
                   *.***       ..*. *.  *     *    .     . *..*
```

Fig. 6

```
Mi clone 1      127 EQCQKhCQRRETEPRHMQTCQQRCERRYEKEKRKQQKRYEEQQRE 171
Mi clone 2      127 EQCQeRCQRhETEPRHMQTCQQRCERRYEKEKRKQQKRYEEQQRE 171
Mi clone 3      127 EQCQKRCQRRETEPRHMQICQQRCERRYEKEKRKQQKRYEEQQRE 171
cotton vicilin   88 EECQQECRQQEE--RQQPQCQQRCLKRFEQEQQ------------ 118
cocoa vicilin    86 QQCQGRCQEQQQGQREQQQCQRKCWEQY-KEQ------------- 116
                    ..**  *. ..    *    **..*   .. .*.

Mi clone 1      172 DEEKYEERMKEEDNKRDPQQREYEDCRRRCEQQE--PRQQHQCQl 214
Mi clone 2      172 DEEKYEERMKEEDNKRDPQQREYEDCRRRCEQQE--PRQQYQCQR 214
Mi clone 3      172 DEEKYEERMKEgDNKRDPQQREYEDCRRhCEQQE--PRlQYQCQR 214
cotton vicilin  119 -----------------QSQRQFQECQQHCHQQEQRPEKKQQCVR 146
cocoa vicilin   117 --------------------------------------------- 116

Mi clone 1      215 RCREQQRQHGRGGDmMNPQRGGSGRYEEGEEeQSDNPYYF-DERS 258
Mi clone 2      215 RCREQQRQHGRGGDLiNPQRGGSGRYEEGEEKQSDNPYYF-DERS 258
Mi clone 3      215 RCqEQQRQHGRGGDLMNPQRGGSGRYEEGEEKQSDNPYYF-DERS 258
cotton vicilin  147 ECREKY--QENPWRGEREEEAEEEETEEGEQEQSHNPFHF-HRRS 188
cocoa vicilin   117 ---------ER-GEHENYHNHKKNRSEEEEGQQRNNPYYFPKRRS 151
                                               ** *  *  **. *   **
```

Fig. 6 (continued)

```
Mi clone 1       259 LSTRFRTEEGHISVLENFYGRSKLLRALKNYRLVLLEANPNAFVL 303
Mi clone 2       259 LSTRFRTEEGHISVLENFYGRSKLLRALKNYRLVLLEANPNAFVL 303
Mi clone 3       259 LSTRFRTEEGHISVLENFYGRSKLLRALKNYRLVLLEANPNAFVL 303
cotton vicilin   189 FQSRFREEHGNFRVLQRFASRHPILRGINEFRLSILEANPNTFVL 233
cocoa vicilin    152 FQTRFRDEEGNFKILQRFAENSPPLKGINDYRLAMFEANPNTFIL 196
                     *  **   * .*  ** .*  *     **    ******.*.*

Mi clone 1       304 PTHLDADAILLVIGGRGALKMIHhDNRESYNLECGDVIRIPAGTT 348
Mi clone 2       304 PTHLDADAILLVIGGRGALKMIHRDNRESYNLECGDVIRIPAGTT 348
Mi clone 3       304 PTHLDADAILLVIGGRGALKMIHRDNRESYNLECGDVIRIPAGTT 348
cotton vicilin   234 PHHCDAEKIYLVTNGRGTLTFLTHENKESYNIVPGVVVKVPAGST 278
cocoa vicilin    197 PHHCDAEAIYFVTNGKGTITFVTHENKESYNVQRGTVVSVPAGST 241
                     *  ** .  ..*.* * *  .  . .*****.  * .***.*

Mi clone 1       349 FYLINRDNNERLHIAKFLQTISTPGQYKEFFPAGGQNPEPYLSTF 393
Mi clone 2       349 FYLINRDNNERLHIAKFLQTISTPGQYKEFFPAGGQNPEPYLSTF 393
Mi clone 3       349 FYLINRDNNERLHIAKFLQTISTPGQYKEFFPAGGQNPEPYLSTF 393
cotton vicilin   279 VYLANQDNKEKLIAVLHRPVNNPGQFEEFFPAGSQRPQSYLRAF  323
cocoa vicilin    242 VYVVSQDNQEKLTIAVLALPVNSPGKYELFFPAGNNKPESYYGAF 286
                     .*  ..**.. *  .. .*.*  *  * ******   * ..*
```

Fig. 6 (continued)

```
Mi clone 1       394  SKEILEAALNTQTEkLRGVf----GQQRE-GVIIRASQEQIRELT  433
Mi clone 2       394  SKEILEAALNTQaERLRGVL----GQQRE-GVIISASQEQIRELT  433
Mi clone 3       394  SKEILEAALNTQTERLRGVL----GQQRE-GVIIRASQEQIRELT  433
cotton vicilin   324  SREILEPAFNTRSEQLDELFGGRQSRRRQQGQG-MFRKASQEQIR  367
cocoa vicilin    287  SYEVLETVFNTQREKLEEILEEQRGQKRQQGQQQGMFRKAKPEQIR 331
                      *  *. *** **  ** *.   .   ..**  .

Mi clone 1       434  RDDSESRhWHIRRGGESSRGPYNLFNKRPLYSNKYGQAYEVKPED  478
Mi clone 2       434  RDDSESRRWHIRRGGESSRGPYNLFNKRPLYSNKYGQAYEVKPED  478
Mi clone 3       434  RDDSESRRWHIRRGGESSRGPYNLFNKRPLYSNKYGQAYEVKPED  478
cotton vicilin   368  ALSQEATSPREK-SGE--RFAFNLLSQTPRYSNQNGRFFEACPPE  409
cocoa vicilin    332  AISQQATSPRHR-GGE--RLAINLLSQSPVYSNQNGRFFEACPED  373
                       . * *** .  **   *. ** .  ***** ****.** *

Mi clone 1       479  YRQLQDMDlSVFIANvTQGSMMGPFFNTRSTKVVVASGEADVEM   523
Mi clone 2       479  YRQLQDMDVSVFIANITQGSMMGPFFNTRSTKVVVASGEADVEM   523
Mi clone 3       479  YRQLQDMDVSVFIANITQGSMMGPFFNTRSTKVVVASGEADVEM   523
cotton vicilin   410  FRQLRDINVTVSALQLNQGSIFVPHYNSKATFVILVTEGNGYAEM  454
cocoa vicilin    374  FSQFQNMDVAVSAFKLNQGAIFVPHYNSKATFVVFVTDGYGYAQM  418
                      : * :.:*.:*:     **::: ****  ::::    * *:*
```

Fig. 6 (continued)

```
Mi clone 1     524 ACPHLSGRHGGRGGGKRHEEEED-----VHYEQVRARLSKREAIV 563
Mi clone 2     524 ACPHLSGRHGGRrGGKRHEEEED-----VHYEQVkARLSKREAIV 563
Mi clone 3     524 ACPHLSGRHGGRGGGKRHEEEEE-----VHYEQVRARLSKREAIV 563
cotton vicilin 455 VSPHLPRQSSYEEEEEEDEEEEQEQEEERRSGQYRKIRSRLSRGD 499
cocoa vicilin  419 ACPHLSRQSQGSQSGRQDRREQEEESEEETFGEFQQVKAPLSPGD 463
                    .***  .              *.          . .   .

Mi clone 1     564 ---VLAGHPVVFVSSGNENLLLFAFGINAQNNHEN-----FLAGR 600
Mi clone 2     564 ---VpvGHPVVFVSSGNENLLLFAFGINAQNNHEN-----FLAGR 600
Mi clone 3     564 ---VLAGHPVVFVSSGNENLLLFAFGINAQNNHEN-----FLAGR 600
cotton vicilin 500 IFVVPANFPVTFVASQNQNLRMTGFGLYNQNINPDHNQRIFVAGK 544
cocoa vicilin  464 VFVAPAGHAVTFFASKDQPLNAVAFGLNAQN-----NQRIFLAGR 503
                           .  * * .*  . *   **.  **         *.**.

Mi clone 1     601 ERNVLQQIEPQAMELAFAAPRKEVEEsFNSQ-DqSIFFPGPRQHQQ 645
Mi clone 2     601 ERNVLQQIEPQAMELAFAAPRKEVEELFNSQ-DESIFFPGPRQHQQ 645
Mi clone 3     601 ERNVLQQIEPQAMELAFAAsRKEVEELFNSQ-DESIFFPGPRQHQQ 645
cotton vicili  545 INHVRQ-WDSQAKELAFGVSSRLVDEIFNSNPQES-YF-VSRQRQR 587
cocoa vicilin  504 --------- ------------------------PFFLNHKQNTN 514
                                                     .*   ..
```

Fig. 6 (continued)

```
Mi clone 1       646 QSPRSTKQQQPLVSILDFVGF 666
Mi clone 2       646 QSsRSTKQQQPLVSILDFVGF 666
Mi clone 3       646 QSPRSTKQQQPLVSILDFVGF 666
cotton vicilin   588 ASE                   590
cocoa vicilin    515 VIKFTVKASAY           525
```

Fig. 6 (continued)

| | 1 | 10 | 20 | 30 | 40 | 47 |
|---|---|---|---|---|---|---|
| **MiAMP2c** | **RQRDPQQQYE** | | **QCQKRCQRRE** | **TEPRHMQICQ** | **QRCERRYEKE** | **KRKQQKR** |
| Gibrat method | CCCCCCCCCH | | HHECCCCCCC | CCCCCCEEEC | CCCCCCCHHH | HHHHHHH |
| Levin method | CCCCCHCCHH | | HHHHHHCHHT | HCSCCCCECC | CHHHTHHHHH | HHHHCHH |
| DPM method | CCCCCCCCCH | | HHHHHHHHHH | CHCCCHHEEH | HHHHHHHHHH | HHHHHCC |
| SOPMA method | CCCCCHHHHH | | HHHHHEECCC | CCCCHEEEEE | EHHHHHHHHH | HHHHHHH |
| PhD method | CCCCHHHHHH | | HHHHHHHHHH | CCCCCHHHHH | HHHHHHHHHH | HHHHCCC |
| Consensus | CCCCCHCCHH | | HHHHHH-HH- | CCCCC--EE- | -HHHHHHHHH | HHHHHHH |

Fig. 7

ANTIMICROBIAL PROTEINS

This is the U.S. national phase under 35 U.S.C. § 371 of International application PCT/AU97/00874, filed Dec. 22, 1997, which claims priority to Australian application PO 4275, filed Dec. 20, 1996.

TECHNICAL FIELD

This invention relates to isolated proteins which exert inhibitory activity on the growth of fungi and bacteria, which fungi and bacteria include some microbial pathogens of plants and animals. The invention also relates to recombinant genes which include sequences encoding the proteins, the expression products of which recombinant genes can contribute to plant cells or cells of other organism's defence against invasion by microbial pathogens. The invention further relates to the use of the proteins and/or genes encoding the proteins for the control of microbes in human and veterinary clinical conditions.

BACKGROUND ART

Microbial diseases of plants are a significant problem to the agricultural and horticultural industries. Plant diseases in general cause millions of tonnes of crop losses annually with fungal and bacterial diseases responsible for significant portions of these losses. One possible way of combating fungal and bacterial diseases is to provide transgenic plants capable of expressing a protein or proteins which in some way increase the resistance of the plant to pathogen attack. A simple strategy is to first identify a protein with antimicrobial activity in vitro, to clone or synthesise the DNA sequence encoding the protein, to make a chimaeric gene construct for efficient expression of the protein in plants, to transfer this gene to transgenic plants and to assess the effect of the introduced gene on resistance to microbial pathogens by comparison with control plants.

The first and most important step in the strategy for disease control described above is to identify, characterise and describe a protein with strong antimicrobial activity. In recent years, many different plant proteins with antimicrobial and/or antifungal activity have been identified and described. These proteins have been categorised into several classes according to either their presumed mode of action and/or their amino acid sequence homologies. These classes include the following: chitinases (Roberts, W. K. et al. [1986] *Biochim. Biophys. Acta* 880:161–170); β-1,3-glucanases (Manners, J. D. et al. [1973] *Phytochemistry* 12:547–553); thionins (Bolmann, H. et al. [1988] *EMBO J.* 7:1559–1565 and Fernadez de Caleya, R. et al. [1972] *Appl. Microbiol.* 23:998–1000); permatins (Roberts, W. K. et al. [1990] *J. Gen. Microbiol.* 136:1771–1778 and Vigers, A. J. et al. [1991] *Mol. Plant-Microbe Interact.* 4:315–323); ribosome-inactivating proteins (Roberts, W. K. et al. [1986] *Biochim. Biophys. Acta* 880:161–170 and Leah, R. et al. [1991] *J. Biol. Chem.* 266:1564–1573); plant defensins (Terras, F. R. G. et al. [1995] *The Plant Cell* 7:573–588); chitin binding proteins (De Bolle, M. F. C. et al. [1992] *Plant Mol. Biol.* 22:1187–1190 and Van Parijs, J. et al. [1991] *Planta* 183:258–264); thaumatin-like, or osmotin-like proteins (Woloshuk, C. P. et al. [1991] *The Plant Cell* 3:619–628 and Hejgaard, J. [1991] *FEBS Letts.* 291:127–131); PR1-typ proteins (Niderman, T. et al. [1995] *Plant Physiol.* 108:17–27.) and the non-specific lipid transfer proteins (Terras, F. R. G. et al. [1992] *Plant Physiol.* 100:1055–1058 and Molina, A. et al. [1993] *FEBS Letts.* 3166:119–122). Another class of antimicrobial proteins from plants is the knottin or knottin-like antimicrobial proteins (Cammue, B. P. A. et al. [1992] *J. Biol. Chem.* 67:2228–2233; Broekaert W. F. et al. (1997) *Crit. Rev. in Plant Sci.* 16(3):297–323). A class of antimicrobial proteins termed 4-cysteine proteins has also been reported in the literature which class includes Maize Basic Protein (MBP-1) (Duvick, J. P. et al. [1992] J. Biol. Chem. 267:18114–18120). A novel antimicrobial protein which does not fit into any previously described class of antimicrobial proteins has also been isolated from the seeds of *Macadamia integrifolia* termed MiAMP1 (Marcus, J. P. et al. [1997] *Eur. J. Biochem.* 244:743–749). In addition, plants are not the sole source of antimicrobial proteins and there are many reports of the isolation of antimicrobial proteins from animal and microbial cells (reviewed in Gabay, J. E. [1994] *Science* 264:373–374 and in "Antimicrobial peptides" [1994] *CIBA Foundation Symposium* 186, John Wiley and Sons Publ., Chichester, UK).

There is evidence that the ectopic expression of genes encoding proteins that have in vitro antimicrobial activity in transgenic plants can result in increased resistance to microbial pathogens. Examples of this engineered resistance include transgenic plants expressing genes encoding: a plant chitinase, either alone (Broglie, K. et al. [1991] *Science* 254:1194–1197) or in combination with a β-1,3-glucanase (Van den Elzen, P. J. M. et al. [1993] *Phil. Trans. Roy. Soc.* 342:271–278); a plant defensin (Terras, F. R. G. et al. [1995] *The Plant Cell* 7:573–588); an osmotin-like protein (Liu, D. et al. [1994] *Proc. Natl. Acad. Sci. USA* 91:1888–1892); a PR1-class protein (Alexander, D. et al. [1993] *Proc. Natl. Acad. Sci. USA* 90:7327–7331) and a ribosome-inactivating protein (Logemann, J. et al. [1992] *Bio/Technology* 10:305–308).

Although the potential use of antimicrobial proteins for engineering disease resistance in transgenic plants has been described extensively, there are other applications which are worthy of mention. Firstly, highly potent antimicrobial proteins can be used for the control of plant disease by direct application (De Bolle, M. F. C. et al. [1993] in *Mechanisms of Plant Defence Responses*, B. Fritig and M. Legrand eds., Kluwer Acad. Publ., Dordrecht, N L, pp. 433–436). In addition, antimicrobial peptides have potential therapeutic applications in human and veterinary medicine. Although this has not been described for peptides of plant origin it is being actively explored with peptides from animals and has reached clinical trials (Jacob, L. and Zasloff, M. [1994] in "Antimicrobial Peptides", *CIBA Foundation Symposium* 186, John Wiley and Sons Publ., Chichester, UK, pp. 197–223).

Antimicrobial proteins exhibit a variety of three-dimensional structures which will determine in large part the activity which they manifest. Many of the global structures exhibited by these proteins have been determined (Broekaert W. F. et al. (1997) *Crit. Rev. in Plant Sci.* 16(3):297–323). A large factor in determining the stability of these proteins is the presence of disulfide bridges between various cysteines located in α-helical and β-sheet regions. Many peptides with toxic activity such as conotoxin are well known to be stabilized by disulfide bridges (see for example Hill, J. M. et al. (1996) *Biochemistry* 35(27): 8824–8835). In the case of the conotoxin referenced above, a compact structure is formed consisting of a helix, a small-hairpin, a cis-hydroxyproline, and several turns. The molecule is stabilized by three disulfide bonds, two of which connect the α-helix and the β-sheet, forming a solid structural core. Interestingly, eight arginine and lysine side chains in this molecule project into the solvent in a radial orientation relative to the core of the molecule. These cationic side chains form potential sites of interaction with anionic sites on pathogen membranes (Hill, J. M. et al. supra).

The invention described herein constitutes previously undiscovered and thus novel proteins with antimicrobial activity. These proteins can be isolated from *Macadamia integrifolia* (Mi) seeds or from cotton or cocoa seeds. In addition, protein fragments which are antifungal can be derived from larger seed storage proteins containing regions of substantial similarity to the antimicrobial proteins from macadamia described here. Examples of seed storage proteins which contain regions similar to the proteins which have been purified can be seen in FIG. 4. *Macadamia integrifolia* belongs to the family Proteaceae. *M. integrifolia*, also known as Bauple Nut or Queensland Nut, is considered by some to be the world's best edible nut. Cotton (*Gossypium hirsutum*) belongs to the family Malvaceae and is cultivated extensively for its fiber. Cocoa (*Threobroma cacao*) belongs to the family Sterculiaceae and is used around the world for a wide variety of cocoa products.

The fact that both the macadamia and cocoa antimicrobial proteins are found in edible portions of these plants makes these peptides attractive for use in genetic engineering for disease resistance since trangenic plants expressing these proteins are unlikely to show added toxicity. Proteins may also be safe for human and veterinary use.

SUMMARY OF THE INVENTION

According to a first embodiment of the invention, there is provided a protein fragment having antimicrobial activity, wherein said protein fragment is selected from:

(i) a polypeptide having an amino acid sequence selected from:
 residues 29 to 73 of SEQ ID NO: 1
 residues 74 to 116 of SEQ ID NO: 1
 residues 117 to 185 of SEQ ID NO: 1
 residues 186 to 248 of SEQ ID NO: 1
 residues 29 to 73 of SEQ ID NO: 3
 residues 74 to 116 of SEQ ID NO: 3
 residues 117 to 185 of SEQ ID NO: 3
 residues 186 to 248 of SEQ ID NO: 3
 residues 1 to 32 of SEQ ID NO: 5
 residues 33 to 75 of SEQ ID NO: 5
 residues 76 to 144 of SEQ ID NO: 5
 residues 145 to 210 of SEQ ID NO: 5
 residues 34 to 80 of SEQ ID NO: 7
 residues 81 to 140 of SEQ ID NO: 7
 residues 33 to 79 of SEQ ID NO: 8
 residues 80 to 119 of SEQ ID NO: 8
 residues 120 to 161 of SEQ ID NO: 8
 residues 32 to 91 of SEQ ID NO: 21
 residues 25 to 84 of SEQ ID NO: 22
 residues 29 to 94 of SEQ ID NO: 24
 residues 31 to 85 of SEQ ID NO: 25
 residues 1 to 23 of SEQ ID NO: 26
 residues 1 to 17 of SEQ ID NO: 27
 residues 1 to 28 of SEQ ID NO: 28;

(ii) a homologue of (i);

(iii) a polypeptide containing a relative cysteine spacing of C-2X-C-3X-C-(10–12)X-C-3X-C wherein X is any amino acid residue other than cysteine, and is C is cysteine;

(iv) a polypeptide containing a relative cysteine and tyrosine/phenylalanine spacing of Z-2X-C-3X-C-(10–12)X-C-3X-C-3X-Z wherein X is any amino acid residue other than cysteine, and C is cysteine, and Z is tyrosine or phenylalanine;

(v) a polypeptide containing a relative cysteine spacing of C-3X-C-(10–12)X-C-3X-C wherein X is any amino acid residue other than cysteine, and C is cysteine;

(vii) a fragment of the polypeptide of any one of (i) to (vi) which has substantially the same antimicrobial activity as (i).

According to a second embodiment of the invention, there is provided a protein containing at least one polypeptide fragment according to the first embodiment, wherein said polypeptide fragment has a sequence selected from within a sequence comprising SEQ ID NO: 1, SEQ ID NO: 3 or SEQ ID NO: 5.

According to a third embodiment of the invention, there is provided a protein having a sequence selected from SEQ ID NO: 1, SEQ ID NO: 3 or SEQ ID NO: 5.

According to a fourth embodiment of the invention, there is provided an isolated or synthetic DNA encoding a protein according to the first embodiment According to a fifth embodiment of the invention, there is provided a DNA construct which includes a DNA according to the fourth embodiment operatively linked to elements for the expression of said encoded protein.

According to a sixth embodiment of the invention, there is provided a transgenic plant harbouring a DNA construct according to the fifth embodiment.

According to a seventh embodiment of the invention, there is provided reproductive material of a transgenic plant according to the sixth embodiment.

According to an eighth embodiment of the invention, there is provided a composition comprising an antimicrobial protein according to the first embodiment together with an agriculturally-acceptable carrier diluent or excipient.

According to a ninth embodiment of the invention, there is provided a composition comprising an antimicrobial protein according to the first embodiment together with an pharmaceutically-acceptable carrier diluent or excipient.

According to a tenth embodiment of the invention, there is provided a method of controlling microbial infestation of a plant, the method comprising:

i) treating said plant with an antimicrobial protein according to the first embodiment or a composition according to the eighth embodiment; or ii) introducing a DNA construct according to the fifth embodiment into said plant.

According to an eleventh embodiment of the invention, there is provided a method of controlling microbial infestation of a mammalian animal, the method comprising treating the animal with an antimicrobial protein according to the first embodiment or a composition according to the ninth embodiment.

According to a twelfth embodiment of the invention, there is provided a method of preparing an antimicrobial protein, which method comprises the steps of:

a) obtaining or designing an amino acid sequence which forms a helix-turn-helix structure;

b) replacing individual residues to achieve substantially the same distribution of positively charged residues and cysteine residues as in one or more of the amino acid sequences shown in FIG. 4;

c) synthesising a protein comprising said amino acid sequence chemically or by recombinant DNA techniques in liquid culture; and d) if necessary, forming disulphide linkages between said cysteine residues.

Other embodiments of the invention include methods for producing antimicrobial protein.

BRIEF DESCRIPTION OF THE DRAWINGS

FIG. 4 shows the amino acid sequences of MiAMP2a, b, c and d Mi2a, b, c, and d (MiAMP2a, b, c, and d and protein fragments derived from other seed storage proteins which contain regions of homology to the MiAMP2 series of antimicrobial proteins.

FIG. 5 shows an example of a synthetic nucleotide sequence which can be used for the expression and secretion of MiAMP2c in transgenic plants.

FIG. 6 shows the alignment of clones 1–3 from macadamia containing MiAMP2a, b, c and d subunits together with sequences from cocoa and cotton vicilin seed storage proteins which exhibit significant homology to the macadamia clones.

FIG. 7 displays a series of secondary structure predictions for MiAMP2c.

BEST MODE AND OTHER MODES FOR CARRYING OUT THE INVENTION

Figure 1:
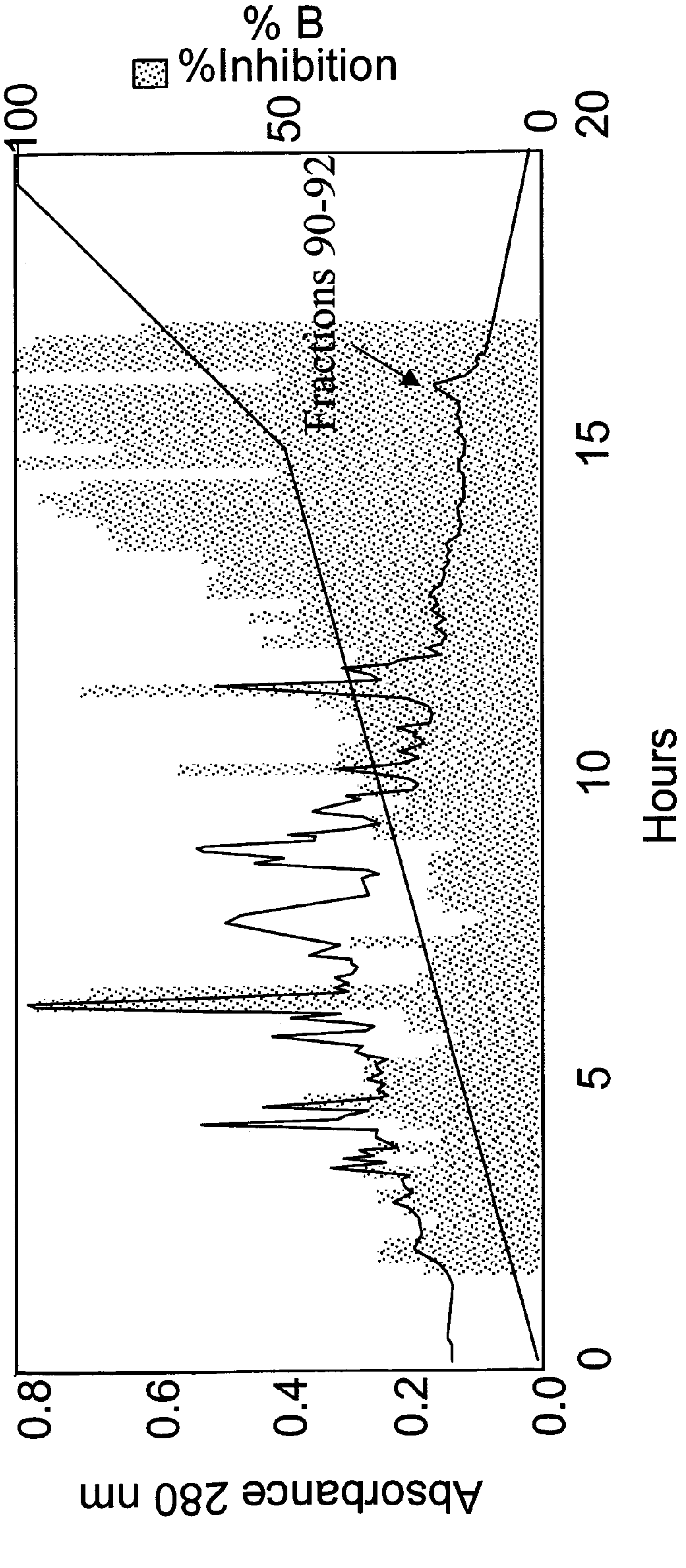
FIG. 1 shows the results of cation-exchange chromatography of the basic protein fraction of a *Macadamia integrifolia* extract with the results of a bioassay for antimicrobial activity shown for fractions in the region of MiAMP2c elution.

The following abbreviations are used hereafter:

| | |
|---|---|
| EDTA | ethylenediaminetetraacetic acid |
| IPTG | Isopropyl-β-D-thiogalactopyranoside |
| MeCN | methyl cyanide (acetonitrile) |
| Mi | *Macadamia integrifolia* |
| MiAMP2 | *Macadamia integrifolia* antimicrobial protein series number 2 |
| Ni-NTA | Nickel-nitrilotriacetic acid chromatography media |
| ND | not determined |
| PCR | polymerase chain reaction |
| PMSF | phenylmethylsulphonyl fluoride |
| SDS-PAGE | sodium-dodecylsulphate polyacrylamide gel electrophoresis |
| TFA | trifluoroacetate |

The term homologue is used herein to denote any polypeptide having substantial similarity in composition and sequence to the polypeptide used as the reference. The homologue of a reference polypeptide will contain key elements such as cysteine or other residues spaced at identical intervals such that a substantially similar three-dimensional global structure is adopted by the homologue as compared to the reference. The homologue will also exhibit substantially the same antimicrobial activity as the reference protein.

The present inventors have identified a new class of proteins with antimicrobial activity. Prototype proteins can be isolated from seeds of *Macadamia integrifolia*. The invention thus provides antimicrobial proteins per se and also DNA sequences encoding these antimicrobial proteins.

The invention also provides amino acid sequences of proteins which are homologous to the prototype antimicrobial proteins from *Macadamia integrifolia*. Thus, in addition to the antimicrobial proteins from Macadamia, this invention also provides amino acid sequences of homologues from other species which have hitherto been unrecognized as having antimicrobial activity.

While the first antimicrobial protein in the present series was isolated directly from *Macadamia integrifolia*, additional antimicrobial proteins were identified through cloning efforts, homology searches and subsequent antimicrobial testing of the encoded proteins after expression in and purification from liquid culture. After the first protein from this series was purified from macadamia and termed MiAMP2, clones were obtained which encoded a preproprotein containing MiAMP2. This large protein (666 amino acids), represented by several almost identical clones, contained four adjacent regions with significant similarity to the purified antimicrobial protein fragment (MiAMP2) which itself was found to lie within region three in the cloned nucleotide sequence; hence the purified antimicrobial protein is termed MiAMP2c. Other fragments contained in the 666-amino-acid clone are termed MiAMP2a, b and d as per their locations in the cloned nucleotide sequence. Several other sequences with significant homology to the MiAMP2a, b, c, and d protein fragments were then identifed in the Entrez data base. These homologous sequences were contained within larger seed storage proteins from cotton and cocoa which sequences had not been previously described as containing antimicrobial protein sequences or as exhibiting antimicrobial activity. Fragments of larger seed storage proteins containing sequences homologous to MiAMP2c were tested and are here demonstrated to exhibit antimicrobial activity. Thus, the inventors have established a process for obtaining antimicrobial protein fragments from larger seed storage proteins. In the light of these findings, it is evident that fragments of other seed storage proteins containing sequences similar to the proteins described will also exhibit antimicrobial activity.

In particular, the 47-amino-acid TcAMP1 (for *Theobroma cacao* antimicrobial protein 1) and the 60-amino-acid TcAMP2 sequences were derived from a cocoa vicilin seed storage protein gene sequence (which contains 525 amino acids) (Spencer, M. E. and Hodge R. [1992] *Planta* 186: 567–576). These derived fragments were then expressed in liquid culture. Cocoa vicilin fragments thus expressed and subsequently purified (Examples 10 and 11), were shown to be antimicrobial (Example 15). This is the first report that fragments of the cocoa vicilin protein possess antimicrobial activity. Pools of sequences containing fragments homologous to the MiAMP2c apparently released from cotton vicilin seed storage protein have been shown to possess antimicrobial activity (Chung, R. P. T. et al. [1997] *Plant Science* 127:1–16). This finding is clearly embodied in sequences disclosed in this application.

In addition to showing that cocoa-vicilin-derived fragments exhibit antimicrobial activity, there is herein described additional proteins which exhibit antimicrobial activity. For example, there is described below proteins from Stenocarpus sinuatus which are of similar size to MiAMP2 subunits, react with MiAMP2c antiserum, and contain sequences homologous to MiAMP2 proteins (see FIG. 4). Based on the evidence provided herein, sequences homologous to the MiAMP2c subunit (i.e., MiAMP2a, b, d; TcAMP1; TcAMP2; and cotton fragments 1, 2 and 3—see FIG. 4) constitute proteins which contain the fragment with antimicrobial activity. The antimicrobial activity of MiAMP2 fragments from macadamia, and the TcAMP1 and 2 fragments from cocoa, is exemplified below. R. P. T. Chung et al. (*Plant Science* 127:1–16 [1997]) have demonstrated that the cotton fragments exhibit antimicrobial activity. Other antimicrobial proteins can also be derived from seed storage proteins such as peanut allergen Ara h (Burks, A. W. et al. [1995] *J. Clin. Invest.* 96 (4), 1715–1721), maize globulin (Belanger, F. C. and Kriz, A. L. [1991] *Genetics* 129 (3), 863–872), barley globulin (Heck, G. R. et al. [1993] *Mol. Gen. Genet.* 239 (1–2), 209–218), and soy conglycinin (Sebastiani, F. L. et al. [1990] *Plant Mol. Biol.* 15 (1), 197–201), all of which contain the same key elements which are present in the sequences which are here shown to exhibit antimicrobial activity.

The proteins which contain regions of sequence homologous to MiAMP2 (as in FIG. 4) can be used to construct nucleotide sequences encoding 1) the active fragments of larger proteins, or 2) fusions of multiple antimicrobial fragments. This can be done using standard codon tables and cloning methods as described in laboratory manuals such as *Current Protocols in Molecular Biology* (copyright 1987–1995 edited by Ausubel F. M. et al. and published by John Wiley & Sons, Inc., printed in the USA). Subsequently, these can be expressed in liquid culture for purification and testing, or the sequences can be expressed in transgenic plants after placing them in appropriate expression vectors.

The antimicrobial proteins per se will manifest a particular three-dimensional structure which may be determined using X-ray crystallography or nuclear magnetic resonance techniques. This structure will be responsible in large part for the antimicrobial activity of the protein. The sequence of the protein can also be subjected to structure prediction algorithms to assess whether any secondary structure elements are likely to be exhibited by the protein (see Example 8 and FIG. 7). Secondary structures, thus predicted, can then be used to model three-dimensional global structures.

Although three-dimensional structure prediction is not feasible for most proteins, the secondary structure predictions for MiAMP2c were sufficiently simple and clear that a three-dimensional model structure has been obtained for the MiAMP2c protein. Homologues exhibiting the same cysteine spacing and other key elements will also adopt the same three-dimensional structure. Example 8 shows that the structure most likely to be adopted by MiAMP2c (and homologues) is a helix-turn-helix structure stabilised by at least two disulfide bridges connecting the two antiparallel α-helical segments (see FIG. 8). Additional stabilization can be provided by an extra disulfide bridge (e.g., as in MiAMP2b) or by a hydrophobic ring-stacking interaction between tyrosine and/or phenylalanine residues (e.g., MiAMP2a and MiAMP2c), each located on the same face of the α-helical segments as the normally present cysteine residues which participate in the 2 disulfide linkages mentioned above. NMR signals exhibited by MiAMP2c are consistent with the three-dimensional global model produced from the secondary-structure predictions mentioned above.

It will be appreciated that one skilled in the art could take a protein with known structure, alter the sequence significantly, and yet retain the overall three-dimensional shape and antimicrobial activity of the protein. One aspect of the structure that most likely could not be altered without seriously affecting the structure (and, therefore, the activity of the protein) is the content and spacing of the cysteine residues since this would disrupt the formation of disulfide bonds which are critical to a) maintaining the overall structure of the protein and/or b) making the protein more resistant to denaturation and proteolysis (stabilizing the protein structure). In particular, it is essential that cysteine residues reside on one face of the helix in which they are contained. This can best be accomplished by maintaining a three-residue spacing between the cysteine residues within each helix, but, can also be accomplished with a two-residue interval between the systeine residues provided the cysteines on the other helical segment are separated by three residues (i.e., C-X-X-C-X-X-C-nX-C-X-X-X-C-X-X-X-C where C is cysteine, X is any amino acid other than cysteine, and n is the number of residues forming a turn between the two α-helical segments). Aromatic tyrosine (or phenylalanine) residues can also function to add stability to the protein structure if they are located on the same face of the helix as the cysteine side chains. This can be accomplished by providing appropriate spacing of two or three residues between the aromatic residue and the proximate cysteine residue (i.e., Z-X-X-C-X-X-X-C-nX-C-X-X-X-C-X-X-X-Z where Z is tyrosine or phenylalanine).

Figure 8:
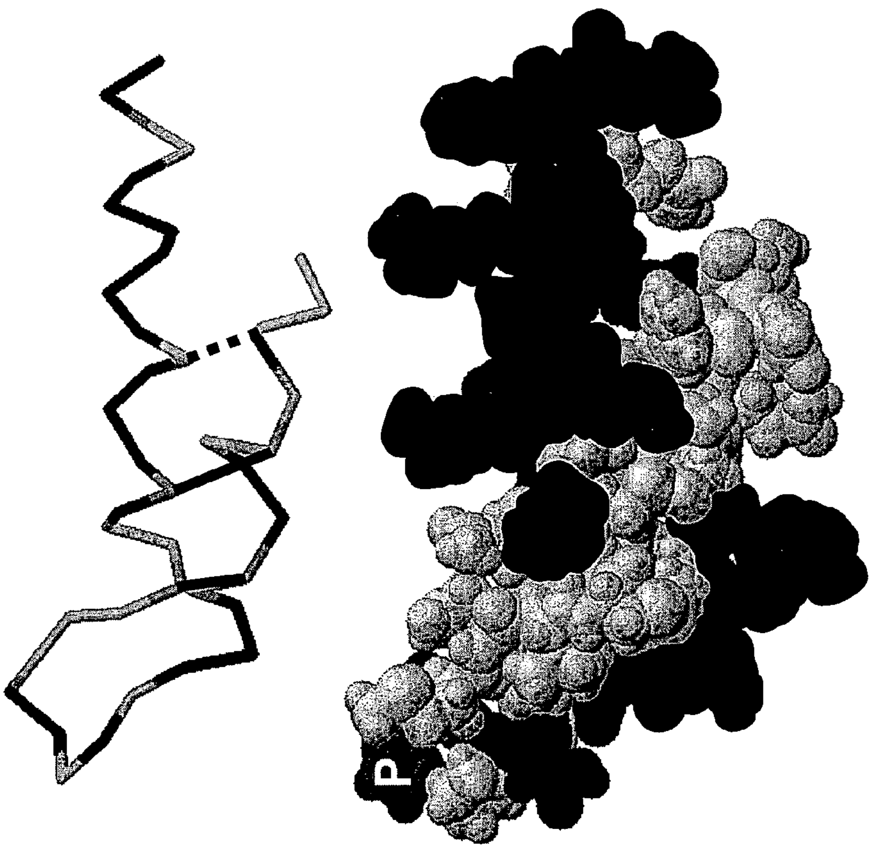
FIG. 8 shows a three-dimensional model of the MiAMP2c protein.

The distribution of positive (and negative) charges on the various surfaces of the protein will also serve a critical role in determining the structure and activity of the protein. In particular, the distribution of positively-charged residues in an α-helical region of a protein can result in positive charges lying on one face of the helix or may result in the charged residues being concentrated in some particular portion of the molecule. An alternative distribution of positively charged residues is for them to project into the solvent in a radial orientation to the core of the protein. This orientation is predicted for several of the MiAMP2 homologues (data not shown). The spacing which is required for positioning of the residues on one face of the helix or the spacing required to accomplish a radial orientation from the core can easily be determined by one skilled in the art using a helical wheel plot with the sequence of interest. A helical wheel plot uses the fact that, in α-helices, each turn of the helix is composed of 3.6 residues on average. This number translates to 100° of rotational translation per residue making it possible to construct a plot showing the distribution of side chains in a helical region. FIG. 8 shows how the spacing of charged residues can lead to most of the positively charged side chains being localised on one face of the helix. It will be appreciated by one of skill in the art that positive charges are conferred by arginine and lysine residues.

In order for the protein to develop into a helix-turn-helix structure, it is also necessary to have particular residues that favor α-helix formation and that also favor a turn structure in the middle portion of the amino acid sequence (and disfavor a helical structure in the turn region). This can be accomplished by a proline residue or residues in the middle of the turn segment as seen with many of the MiAMP2 homologues. When proline is not present, glycine can also contribute to breaking a continuous helix structure, and inducing the formation of a turn at this position. In one case (i.e., TcAMP1), it appears that serine may be taking on this role. It will be appreciated that the residues in this region of the protein will usually favor the formation of a turn structure; residues which fulfill this requirement include proline, glycine, serine, and aspartic acid; but, other residues are also allowed.

The DNA sequences reported here are an extremely powerful tool which can be used to obtain homologous genes from other species. Using the DNA sequences, one skilled in the art can design and synthesize oligonucleotide probes which can be used to screen cDNA libraries from other species of plants for the presence of genes encoding antimicrobial proteins homologous to the ones described here. This would simply involve construction of a cDNA library and subsequent screening of the library using as the oligonucleotide probe one or part of one of the sequences reported here (such as sequence ID. No. 2 or the PCR fragment described in Example 9). Other oligonucleotide sequences coding for proteins homologous to MiAMP2 can also be used for this purpose (e.g., DNA sequences corresponding to cotton and cocoa vicilins). Making and screening of a cDNA library can be carried out by purchasing a kit for said purpose (e.g., from Stratagene) or by following well established protocols described in available DNA cloning manuals (see *Current Protocols in Molecular Biology*, supra). It is relatively straight forward to construct libraries of various species and to specifically isolate vicilin homologues which are similar to the Macadamia, cotton, or cocoa vicilins by using a simple DNA hybridization technique to screen such libraries. Once cloned, these vicilin-related sequences can then be examined for the presence of MiAMP2-like subunits. Such subunits can easily be expressed in *E. coli* using the system described in Examples 10 and 11. Subsequently, these proteins can also be expressed in transgenic.

Genes, or fragments thereof, under the control of a constitutive or inducible promoter, can then be cloned into a biological system which allows expression of the protein encoded thereby. Transformation methods allowing for the protein to be expressed in a variety of systems are known. The protein can thus be expressed in any suitable system for the purpose of producing the protein for further use. Suitable hosts for the expression of the protein include *E. coli*, fungal cells, insect cells, mammalian cells, and plants. Standard methods for expressing proteins in such hosts are described in a variety of texts including section 16 (Protein Expression) of *Current Protocols in Molecular Biology* (supra).

Plant cells can be transformed with DNA constructs of the invention according to a variety of known methods (*Agrobacterium*, Ti plasmids, electroporation, micro-injections, micro-projectile gun, and the like). DNA sequences encoding the *Macadamia integrifolia* antimicrobial protein subunits (i.e. fragments a, b, c, or d from the MiAMP2 clones) as well as DNA coding for other homologues can be used in conjunction with a DNA sequence encoding a preprotein from which the mature protein is produced. This preprotein can contain a native or synthetic signal peptide sequence which will target the protein to a particular cell compartment (e.g., the apoplast or the vacuole). These coding sequences can be ligated to a plant promoter sequence that will ensure strong expression in plant cells. This promoter sequence might ensure strong constitutive expression of the protein in most or all plant cells, it may be a promoter which ensures expression in specific tissues or cells that are susceptible to microbial infection and it may also be a promoter which ensures strong induction of expression during the infection process. These types of gene cassettes will also include a transcription termination and polyadenylation sequence 3' of the antimicrobial protein coding region to ensure efficient production and stabilisation of the mRNA encoding the antimicrobial proteins. It is possible that efficient expression of the antimicrobial proteins disclosed herein might be facilitated by inclusion of their individual DNA sequences into a sequence encoding a much larger protein which is processed in planta to produce one or more active MiAMP2-like fragments.

Gene cassettes encoding the MiAMP2 series antimicrobial proteins (i.e., MiAMP2a, b, c, or d; or all of the subunits together; or the entire MiAMP2 clone) or homologues of the MiAMP2 proteins as described above can then be expressed in plant cells using two common methods. Firstly, the gene cassettes can be ligated into binary vectors carrying: i) left and right border sequences that flank the T-DNA of the *Agrobacterium tumefaciens* Ti plasmid; ii) a suitable selectable marker gene for the selection of antibiotic resistant plant cells; iii) origins of replication that function in either *A. tumefaciens* or *Escherichia coli;* and iv) antibiotic resistance genes that allow selection of plasmid-carrying cells of *A. tumefaciens* and *E. coli*. This binary vector carrying the chimaeric MiAMP2 encoding gene can be introduced by either electroporation or triparental mating into *A. tumefaciens* strains carrying disarmed Ti plasmids such as strains LBA4404, GV3101, and AGL1 or into *A. rhizogenes* strains such as A4 or NCCP1885. These Agrobacterium strains can then be co-cultivated with suitable plant explants or intact plant tissue and the transformed plant cells and/or regenerants selected using antibiotic resistance.

A second method of gene transfer to plants can be achieved by direct insertion of the gene in target plant cells. For example, an MiAMP2-encoding gene cassette can be co-precipitated onto gold or tungsten particles along with a plasmid encoding a chimaeric gene for antibiotic resistance in plants. The tungsten particles can be accelerated using a fast flow of helium gas and the particles allowed to bombard a suitable plant tissue. This can be an emblyogenic cell culture, a plant explant, a callus tissue or cell suspension or an intact meristem. Plants can be recovered using the antibiotic resistance gene for selection and antibodies used to detect plant cells expressing the MiAMP2 proteins or related fragments.

The expression of MiAMP2 proteins in the transgenic plants can be detected using either antibodies raised to the protein(s) or using antimicrobial bioassays. These and other related methods for the expression of MiAMP2 proteins or fragments thereof in plants are described in *Plant Molecular Biology* (2nd ed., edited by Gelvin, S. B. and Schilperoort, R. A., © 1994, published by Kluwer Academic Publishers, Dordrecht, The Netherlands)

Both monocotyledonous and dicotyledonous plants can be transformed and regenerated. Examples of genetically modified plants include maize, banana, peanut, field peas, sunflower, tomato, canola, tobacco, wheat, barley, oats, potato, soybeans, cotton, carnations, roses, sorghum. These, as well as other agricultural plants can be transformed with the antimicrobial genes such that they would exhibit a greater degree of resistance to pathogen attack. Alternatively, the proteins can be used for the control of diseases by topological application.

The invention also relates to application of antimicrobial protein in the control of pathogens of mammals, including humans. The protein can be used either in topological or intravenous applications for the control of microbial infections.

As indicated above in the description of the twelfth embodiment, the invention includes within its scope the preparation of antimicrobial proteins based on the prototype MiAMP2 series of proteins. New sequences can be designed from the MiAMP2 amino acid sequences which substantially retain the distribution of positively charged residues relative to cysteine residues as found in the MiAMP2 proteins. The new sequence can be synthesised or expressed from a gene encoding the sequence in an appropriate host cell. Suitable methods for such procedures have been described above. Expression of the new protein in a genetically engineered cell will typically result in a product having a correct three-dimensional structure, including correctly formed disulfide linkages between cysteine residues. However, even if the protein is chemically synthesised, methods are known in the art for further processing of the protein to break undesirable disulfide bridges and form the bridges between the desired cysteine residues to give the desired three-dimensional structure should this be necessary.

*Macadamia integrifolia* Antimicrobial Proteins Series Number 2

As indicated above, a new series of potent antimicrobial proteins has been identified in the seeds of *Macadamia integrifolia*. The proteins collectively are called the MiAMP2 series of antimicrobial proteins (or MiAMP2 proteins) because they are all found on one large preproprotein which is processed into smaller subunits, each exhibiting antimicrobial activity; they represent the second class of antimicrobial proteins isolated from *Macadamia integrifolia*. Each protein fragment of the series has a characteristic pI value. MiAMP2a, b, c, and d subunits as shown in FIG. 4 have predicted pI values of 4.4, 4.6, 11.5, and 11.6 respectively (predicted using raw sequence data without the His tag or cleavage sequences associated with expression of fragments in the vector pET16b), and contain two sets of CXXXC motifs (SEQ ID NO:40) which are important in stabilizing the three-dimensional structure of the protein through the formation of disulfide bonds. Additionally, the proteins contain either an added set of aromatic (tyrosine/phenylalanine) residues or an added set of cysteine residues located at positions which would give more stability to the helix-turn-helix structure as described above and in Example 8.

The amino acid sequences of the MiAMP2 series of proteins share significant homology with fragments of previously described proteins in sequence databases (Swiss Prot and Non-redundant databases) searched using the BLASTP algorithm (Altschul, S. F. et al. [1990] *J. Mol. Biol.* 215: 403). In particular, MiAMP2a, b, c and d sequences exhibit significant similarity with regions of cocoa vicilin and cotton vicilin (as seen in FIG. 6). Some similarity is also seen with fragments from other seed storage proteins of peanut (Burks, A. W. et al. [1995] *J Clin. Invest.* 96 (4), 1715–1721), maize (Belanger, F. C. and Kriz, A. L. [1991] *Genetics* 129 (3), 863–872), barley (Heck, G. R. et al. [1993] *Mol. Gen. Genet.* 239 (1–2), 209–218), and soybean (Sebastiani, F. L. et al. [1990] *Biol.* 15 (1), 197–201). Although, in some cases the homology is not extremely high (for example, 18% identity between MiAMP2a and cotton subunit 1; see FIG. 4), the spacing of the main four cysteine residues is conserved in all subunits and homologues. In addition, both cotton and cocoa vicilin-derived subunits retain the conserved tyrosine or phenylalanine residues as additional stabilizers of the tertiary structure. The cotton and cocoa vicilins with 525 and 590 amino acids, respectively, are much larger proteins than MiAMP2c (47 amino acids) (see FIGS. 4 and 6). Although MiAMP2 subunits also share some homology with MBP-1 antimicrobial protein from maize (Duvick, J. P. et al. (1992) *J Biol Chem* 267:18814–20) the number of residues between the CXXXC motifs is 13 which puts MBP-1 outside the specifications for the spacing given here in this application. MBP-1 is also a smaller protein (33 amino acids), overall, than the sequences claimed here and there is no evidence available the MBP-1 is derived from a larger seed storage protein other than some similarity with a portion of miaze globulin protein. However, MBP-1 cannot be derived from the maize globulin since maize globulin contains 10 residues between the two CXXXC motifs while MBP-1 contains 13. The alignments in FIGS. 4 and 6 show the similarity in cysteine spacing between MiAMP2 subunits and the cocoa and cotton vicilin-derived molecules. The cysteine and the aromatic tyrosine/phenylalanine residues in FIGS. 4 and 6 are highlighted with bold underlined text. FIG. 4 also shows the alignment of additional proteins which can be expressed in liquid culture and shown to exhibit antimicrobial activity.

All of the MiAMP2 homologues that have been tested exhibit antifungal activity. MiAMP2 homologues show very significant inhibition of fungal growth at concentrations as low as 2 μg/ml for some of the pathogens/microbes against which the proteins were tested. Thus they can be used to provide protection against several plant diseases. MiAMP2 homologues can be used as fungicides or antibiotics by application to plant parts. The proteins can also be used to inhibit growth of pathogens by expressing them in transgenic plants. The proteins can also be used for the control of human pathogens by topological application or intravenous injection. One characteristic of the proteins is that inhibition of some microbes is suppressed by the presence of $Ca^{2+}$ (1 mM). An example of this effect is provided for MiAMP2c subunit in Table 1.

Some of the MiAMP2 proteins and homologues could also function as insect control agents. Since some of the proteins are extremely basic (e.g., pI>11.5 for MiAMP2c and d subunits), they would maintain a strong net-positive charge even in the highly alkaline environment of an insect gut. This strong net-positive charge would enable it to interact with negatively charged structures within the gut. This interaction may lead to inefficient feeding, slowing of growth, and possibly death of the insect pest.

Non-limiting examples of the invention follow.

EXAMPLE 1

Extraction of Basic Protein from *Macadamia integrifolia* Seeds

Twenty five kilograms of Mi nuts (purchased from the Macadamia Nut Factory, Queensland, Australia) were ground in a food processor (The Big Oscar, Sunbeam) and the resulting meal was extracted for 2–4 hours at 4° C. with 50 L of an ice-cold extraction buffer containing 10 mM $NaH_2PO_4$, 15 mM $Na_2HPO_4$, 100 mM KCl, 2 mM EDTA, 0.75% polyvinylpolypyrolidone, and 0.5 mM phenylmethylsulfonyl fluoride (PMSF). The resulting homogenate was run through a kitchen strainer to remove larger particulate material and then further clarified by centrifugation (4000 rpm for 15 min) in a large capacity centrifuge. Solid ammonium sulphate was added to the supernatant to obtain 30% relative saturation and the precipitate allowed to form overnight with stirring at 4° C. Following centrifugation at 4000 rpm for 30 min, the supernatant was taken and ammonium sulphate added to achieve 70% relative saturation. The solution was allowed to precipitate overnight and then centrifuged at 4000 rpm for 30 min in order to collect the precipitated protein fraction. The precipitated protein was resuspended in a minimal volume of extraction buffer and centrifuged once again (13,000 rpm×30 min) to remove any insoluble material yet remaining. After dialysis (10 mM ethanolamine pH 9.0, 2 mM EDTA and 1 mM PMSF) to remove residual ammonium sulphate, the protein solution was passed through a Q-Sepharose Fast Flow column (5×12 cm) previously equilibrated with 10 mM ethanolamine (pH 9), 2 mM in EDTA). The collected flowthrough from this column represents the basic (pI>9) protein fraction of the seeds. This fraction was further purified as described in Example 3.

EXAMPLE 2

Antifungal and Antibacterial Activity Assays

In general, bioassays to assess antifungal and antibacterial activity were carried out in 96-well plates. Typically, the test organism was suspended in a synthetic growth medium consisting of $K_2HPO_4$ (2.5 mM), $MgSO_4$ (50 μM), $CaCl_2$ (50 μM), $FeSO_4$ (5 μM), $CoC_2$ (0.1 μM), $CuSO_4$ (0.1 μM), $Na_2MoO_4$ (2 μM), $H_3BO_3$ (0.5 μM), KI (0.1 μM), $ZnSO_4$ (0.5 μM), $MnSO_4$ (0.1 μM), glucose (10 g/L), asparagine (1 g/L), methionine (20 mg/L), myo-inositol (2 mg/L), biotin (0.2 mg/L), thiamine-HCl (1 mg/L) and pyridoxine-HCL (0.2 mg/L). The test organism consisted of bacterial cells, fungal spores (50,000 spores/ml) or fungal mycelial fragments (produced by blending a hyphal mass from a culture of the fungus to be tested and then filtering through a fine mesh to remove larger hyphal masses). Fifty microliter of the test organism suspended in medium was placed into each well of the microtiter plate. A further 50 μl of the test antimicrobial solution was added to appropriate wells. To deal with well-to-well variability in the bioassay, 4 replicates of each test solution were done. Sixteen wells from each 96-well plate were used as controls for comparison with the test solutions.

Unless otherwise stated, incubation was at 25° C. for 48 hours. All fungi including yeast were grown at 25° C. *E. coli* were grown at 37° C. and other bacteria were bioassayed at 28° C. Percent growth inhibition was measured by following the absorbance at 600 nm of growing cultures over various time intervals and is defined as 100 times the ratio of the average change in absorbance in the control wells minus the change in absorbance in the test well divided by the average change in absorbance at 600 nm for the control wells (i.e., [(avg change in control wells–change in test well)/(avg change in control wells)]×100). Typically, measurements were taken at 24 hour intervals and the period from 24–48 hours was used for % Inhibition measurements.

EXAMPLE 3

Purification of Antimicrobial Protein from *Macadamia integrifolia* Basic Protein Fraction The starting material for the isolation of the Mi antimicrobial protein was the basic fraction extracted from the mature seeds as described above in Example 1. This protein was further purified by cation exchange chromatography as shown in FIG. 1.

About 4 g of the basic protein fraction dissolved in 20 mM sodium succinate (pH 4) was applied to an S-Sepharose High Performance column (5×60 cm) (Pharmacia) previously equilibrated with the succinate buffer. The column was eluted at 17 ml/min with a linear gradient of 20 L from 0 to 2 M NaCl in 20 mM sodium succinate (pH 4). The eluate was monitored for protein by on-line measurement of the absorbance at 280 nm and collected in 200 ml fractions. Portions of each fraction were subsequently tested in the antifungal activity assay against *Phytopthora cryptogea* at a concentration of 100 μg/ml in the presence and absence of 1 mM $Ca^{2+}$. Results of bioassays are included in FIGS. 1*a* and 1*b* where the elution gradient is shown as a solid line and the shaded bars represent % Inhibition. The FIG. 1*a* assays were conducted without added $Ca^{2+}$ while 1 mM $Ca^{2+}$ was included in the FIG. 1*b* assays. Fractionation yielded a number of unresolved peaks eluting between 0.05 and 2 M NaCl. A peak eluting at about 16 hours into the separation (fractions 90–92) showed significant antimicrobial activity.

Figure 2:
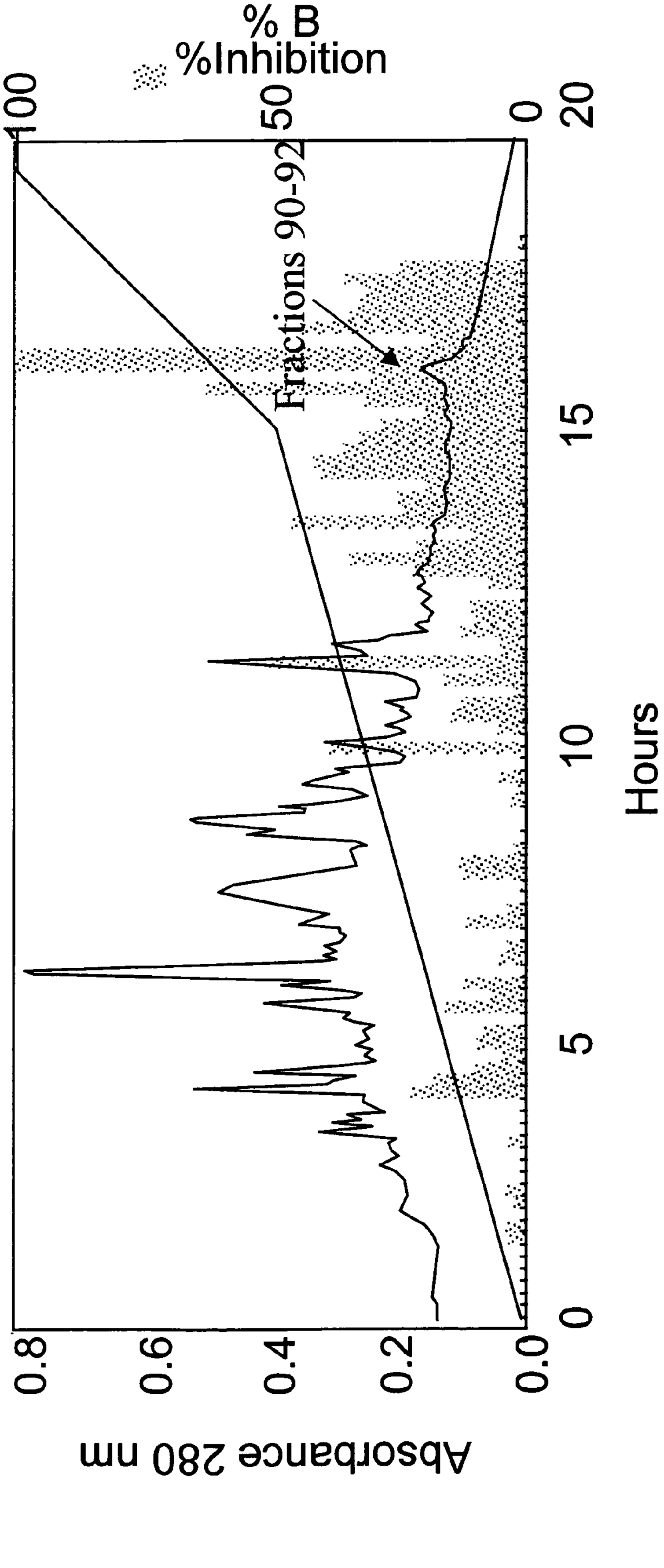
FIG. 2 shows the results of including 1 mM $Ca^{2+}$ in a parallel bioassay of fractions from the cation-exchange separation.
Figure 3:
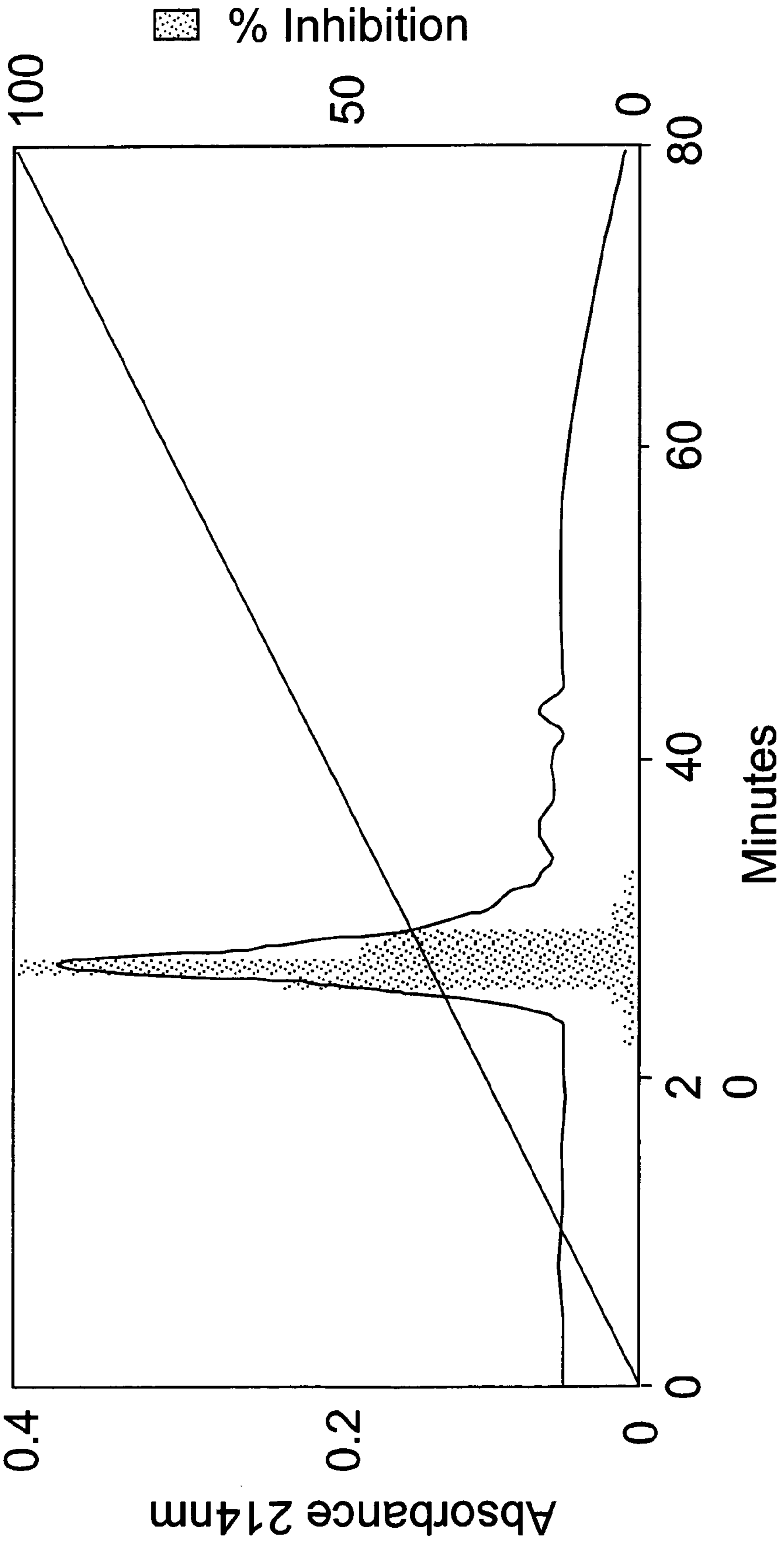
FIG. 3 shows a reverse-phase HPLC profile of highly inhibitory fractions containing MiAMP2c from the cation-exchange separation in FIGS. 1 and 2 together with % inhibition of growth exhibited by the HPLC fractions.

Fractions showing significant antimicrobial activity were further purified by reversed-phase chromatography. Aliquots of fractions 90–92 were loaded onto a Pep-S ($C_2/C_{18}$), column (25×0.93 cm) (Pharmacia) equilibrated with 95% $H_2O$/5% MeCN/0.1% TFA (=100% A). The column was eluted at 3 ml/min with a 240 ml linear gradient (80 min) from 100% A to 100% B (=5% $H_2O$/95% MeCN/0.1% TFA). Individual peaks were collected, vacuum dried three times in order to remove traces of TFA, and subsequently resuspended in 500 microliter of milli-Q water (Millipore Corporation water purification system) for use in bioassays as described in Example 2. FIG. 2 shows the HPLC profile of purified fraction 92 from the cation-exchange separation shown in FIGS. 1 and 2. Protein elution was monitored at 214 nm. The acetonitrile gradient is shown by the straight line. Individual peaks were bioassayed for antimicrobial activity: the bars in FIG. 3 show the inhibition corresponding to 15 μg/ml of material from each of the fractions. The active protein elutes at approximately 27 min (~30% MeCN/0.1% TFA) and is called MiAMP2c.

EXAMPLE 4

Purity of Isolated MiAMP2c

The purity of the isolated antimicrobial protein was verified by native SDS-PAGE followed by staining with coomassie blue protein staining solution. Electrophoresis was performed on a 10–20% tricine gradient gel (Novex) as per the manufacturers recommendations (100 V, 1–2 hour separation time). Under these conditions the purified MiAMP2c migrates as a single discrete band (<10 kDa in size). The detection of a single major band in the SDS-PAGE analysis together with single peaks eluting in the cation-exchange and reversed-phase separations (not shown), gives strong indication that the MiAMP2c preparation is greater than 95% pure and therefore the activity of the preparation was almost certainly due to the MiAMP2c alone and not to a minor contaminating component. A clean signal in mass spectrometric analysis (Example 5 below) also supports this conclusion.

EXAMPLE 5

Mass Spectroscopic Analysis of MiAMP2c

Purified MiAMP2c was submitted for mass spectroscopic analysis. Approximately 1 μg of protein in solution was used for testing. Analysis showed the protein to have a molecular weight of 6216.8 Da±2 Da. Additionally, the protein was subjected to reduction of disulfide bonds with dithiothreitol and alkylation with 4-vinylpyridine. The product of this reduction/alkylation was then submitted for mass spectroscopic analysis and was shown to have gained 427 mass units (i.e. molecular weight was increased by approximately 4×106 Da). The gain in mass indicated that four 4-vinylpyridine groups had reacted with the reduced protein, demonstrating that the protein contains a total of 4 cysteine residues. The cysteine content has also been subsequently confirmed through amino acid sequencing.

EXAMPLE 6

Amino Acid Sequence of MiAMP2c Protein

Approximately 1 μg of the pure protein which had been reduced and alkylated was subjected to Automated Edman degradation N-terminal sequencing. In the first sequencing run, the sequence of the first 39 residues was determined. Subsequently, approximately 1 mg of MiAMP2c was reacted with Cyanogen Bromide which cleaved the protein on the C-terminal side of Methionine-26. The C-terminal fragment generated by the cleavage reaction was purified by reversed-phase HPLC and sequenced, yielding the remaining sequence of MiAMP2c (i.e. residues 27–47). The full amino acid sequence is RQRDP QQQYE QCQER CQRHE TEPRH MQTCQ QRCER RYEKE KRKQQ KR and represents amino acids 118 to 164 of clone 3 from Example 9 (see FIG. 6 and SEQUENCE ID NO: 5). In the figure, cysteine residues are in bold type and underlined to facilitate recognition of the spacing patterns. Depending on the number of disulfide bonds that are formed, the protein mass will range from 6215.6 to 6219.6 Da. This is in close agreement with the mass of 6216.8±2 Da obtained by mass spectrometric analysis (Example 5). The measured mass closely approximates the predicted mass of MiAMP2c in a two-disulfide form as is expected to be the case.

EXAMPLE 7

Synthetic DNA Sequence Coding for MiAMP2c with a Leader Peptide

Using standard codon tables it is possible to reverse-translate the protein sequences to obtain DNA sequences that will code for the antimicrobial proteins. The software program MacVector 4.5.3 was used to enter the protein sequence and obtain a degenerate nucleotide sequence. A codon usage table for tobacco was referenced in order to pick codons that would be adequately represented in tobacco for purposes of obtaining high expression in this test plant. A 30 amino-acid leader peptide was also designed to ensure efficient processing of the signal peptide and secretion of the peptide extracellularly. For this purpose, the method of Von Hiejne was used to evaluate a series of possible leader sequences for probability of cleavage at the correct position [Von Hiejne, G. (1986) *Nucleic Acids Research* 14(11): 4683–4690]. In particular, the amino acid sequence MAWFH VSVCN AVFVV IIIIM LLMFV PVVRG (Sequence ID. No. 11) was found to give an optimal probability of correct processing of the signal peptide immediately following the G (Gly) of this leader sequence. A 5' untranslated region from tobacco mosaic virus was also added to this synthetic gene to promote higher translational efficiency [Dowson, M. J., et al. (1994) *Plant Mol. Biol. Rep.* 12(4): 347–357]. The synthetic gene also contains restriction sites at the 5' and 3' ends and immediately 5' of the start ATG for efficient cloning and subcloning procedures. FIG. 5 shows a synthetic DNA sequence suitable for use in plant expression experiments. In this Figure, the arrow shows where translation is initiated and the triangular symbol indicates the point of cleavage of the signal peptide.

EXAMPLE 8

Structure Prediction of MiAMP2c Protein

Using sequence analysis algorithms, putative secondary structure motifs can be assigned to the protein. Five different algorithms were used to predict whether α-helices, β-sheets, or turns can occur in the MiAMP2c protein (FIG. 4). Methods were obtained from the following sources: DPM method, Deleage, G., and Roux, B. (1987) *Prot. Eng.* 1:289–294; SOPMA method, Geourjon, C., and Deleage, G. (1994) *Prot. Eng.* 7:157–164; Gibrat method, Gibrat, J. F., Gamier, J., and Robson, B. (1987) *J. Mol. Biol.* 198: 425–443; Levin method, Levin, J. M., Robson, B., and Gamier, J. (1986) *FEBS Lett.* 205:303–308; and PhD method, Rost, B., And Sander, C. (1994) *Proteins* 19:55–72. FIG. 7 shows the predicted locations of α-helices, β-sheets and turns. The following symbols have been used in FIG. 7: C, coil (unstructured); H, alpha helix; E, β-sheet; and S, turn. Underlined residues are those which were predicted to exhibit an α-helical structure by at least 2 separate structure prediction methods; these are represented as helices in FIG. 8.

It is clear from the secondary structure predictions that the protein is highly α-helical. While secondary structure prediction is often difficult and inaccurate, this particular prediction gives a clear indication of the structure of the protein. Examination of the secondary-structure predictions show a clear preponderance of two α-helical regions broken by a stretch of about 5–8 residues. This is highly suggestive of a helix-turn-helix motif.

Helical wheel analysis of the MiAMP2c amino acid sequence shows that cysteine residues with a CXXXC spacing (SEQ ID NO:40)will be aligned on one face of the helix in which they are located. Since the cysteines are involved in disulfide bond formation, the cysteine side chains in one helix must form covalent bonds with the cysteine side chains located on the other helical segment. When the helical segments are arranged in such a way as to bring the cysteine side chains from each respective helix into proximity with the other cysteine side chains, the resulting three-dimensional structure is shown in FIG. 8. This structure exhibits a remarkable distribution of positively charge residues on one face of the protein comprised of two helices held together by two disulfide bonds. FIG. 8 shows how the spacing of positively charged residues in helical regions of this molecule will cause these side chains to lie on one face of the helix. The positively charged residues are the dark side chains outlined in black. Other dark side chains represent acidic residues. A proline residue (grey colour marked with a 'P') is located at the extreme left end of the molecule in the turn region. Solid black lines show where disulfide bonds connect the two helices. The dotted line shows where the two aromatic hydrophobic residues interact to add stability to the helix-turn-helix structure.

This helix-turn-helix structure will be adopted by all MiAMP2 homologues containing the same cysteine spacing and residues with helix and turn-forming propensities. Other MiAMP2 fragment sequences can be superimposed onto the global structure shown in FIG. 8. The overall structure will remain essentially the same but the charge distribution will vary according to the sequences involved. In the case of MiAMP2b, the dotted line would represent an added disulfide bridge instead of a hydrophobic interaction.

EXAMPLE 9 cDNA Cloning of Genes Corresponding to MiAMP2c

PCR Amplification of a Genomic Fragment of the MiAMP2c Gene

Using the reverse-translated nucleotide sequences, degenerate primers were made for use in PCR reactions with genomic DNA from Macadamia. Primer JPM17 sequence was 5' CAG CAG CAG TAT GAG CAG TG 3' and primer JPM20 degenerate sequence was 5' TTT TTC GTA (T/T)C (T/G) (G/T)C(T/G) TTC GCA 3' (SEQ ID NOS: 12 and 13). Primers JPM17 and JPM20 were used in PCR amplifications carried out for 30 cycles with 30 sec at 95° C., 1 min at 50° C., and 1 min at 72° C. PCR products with sizes close to those which were expected were directly sequenced (ABI PRISM Dye Terminator Cycle Sequencing Ready Reaction Kit from Perkin Elmer Corporation) after excising DNA bands from agarose gels and purifying them using a Qiagen DNA clean-up kit. Using this approach, it was possible to amplify a fragment of DNA of approximately 100 bp. Direct sequencing of this nucleotide fragment yielded the nucleotide sequence corresponding to a portion of the amino acid sequence of the antimicrobial protein MiAMP2c (amino acids 7–39 of FIG. 4). The partial nucleotide sequence obtained from the above-mentioned fragment excluding the primer sequences was 5' TCA GAA GCG CTG CCA ACG GCG CGA GAC AGA GCC ACG ACA CAT GCA AAT TTG TCA ACA ACG C 3' (corresponding to base pairs 264 to 324 in SEQ ID NO:6). This sequence can be used for a variety of purposes including screening of cDNA and genomic libraries for clones of MiAMP2 homologues or design of specific primers for PCR amplification reactions.

Messenger RNA Isolation from Macadamia Nut Kernels

Fifty-eight grams of Macadamia nut kernels were ground to powder under liquid nitrogen using a mortar and pestel. RNA from ground material was then purified using a Guanidine thiocyanate/Cesium chloride technique (*Current Protocols in Molecular Biology*, supra). Using this method approximately 5 mg of total RNA was isolated. Messenger RNA was then purified from total RNA using a spun column mRNA purification kit (Pharmacia).

cDNA Library Construction

A cDNA library was constructed in a lambda ZAP vector using a library kit from Stratagene. A total of 6 reactions were performed using 25 micrograms of messenger RNA. First and second strand cDNA synthesis was performed using MMLV Reverse transcriptase and DNA Polymerase I, respectively. After blunting the cDNA with Pfu DNA Polymerase, Eco RI linker adapters were ligated to the DNA. DNA was then kinased using T4 polynucleotide kinase and the DNA subsequently digested with Xho I restriction endonuclease. At this point cDNA material was fractionated according to size using a sephacryl-S500 column supplied with the kit. DNA was then ligated into the lambda ZAP vector. The vector containing ligated insert was then packaged into lambda phage (Gigapack III packaging extract from Stratagene).

Screening of Library

The library constructed above was then plated and screened in XL1-blue *E. coli* bacterial lawns growing in top agarose. Plaques containing individual clones were isolated by lifting onto Hybond N+ membranes (Amersham LIFE SCIENCE), hybridizing to a radiolabeled version of the genomic DNA fragment amplified above, imaging of the blot, and picking of positive clones for the next round of screening. After secondary and tertiary screening, plaques were sufficiently isolated to allow picking of single clones. Several clones were obtained, and subsequently the pBK-CMV vector portion from the larger lambda vector was excised.

Sequence of MiAMP2c cDNA Clones

Vectors (pBK-CMV) containing putative MiAMP2c clones were sequenced to obtain the DNA sequence of the cloned inserts. Seven clones were partially sequenced and an additional three clones were fully sequenced (see SEQ ID NOS: 2, 4 and 6 for DNA sequences of the macadamia clones). Translation of the DNA sequences showed that the full length clones encoded highly similar proteins of 666 amino acids. FIG. 6 shows that these proteins have substantial similarity to vicilin seed-storage proteins from cocoa and cotton. Stars show positions of conserved identities and dots show positions of conserved similarities. Examination of the protein sequences revealed that the exact MiAMP2c sequence is found within the translated protein sequence of clone 3 at amino acid positions 118 to 164 (see FIG. 6); clones 1 and 2 contained sequences differing from MiAMP2c by 2 residues and 3 residues, respectively, out of 47 amino acids total in the MiAMP2c sequence.

The translation products of the full-length clones (i.e., clones 1 and 2) consist of a short signal peptide from residues 1 to 28, a hydrophilic region from residues 29 to ~246, and then two segments stretching from residues 246 to 666 with a stretch of acidic residues separating them at positions 542–546.

Significantly, the hydrophilic region containing the sequence for MiAMP2c, also contains 3 additional segments which are very similar to MiAMP2 (termed MiAMP2a, b and d). These 4 segments (found between residues 28 and ~246) are separated by stretches in which approximately four out of five residues are acidic (usually glutamic acid). These acidic stretches occur at positions 64–68, 111–115, 171–174, and 241–246 and appear to delineate processing sites for cleavage of the 666-residue preproprotein into smaller functional fragments (acidic stretches delineating cleavage sites are shown as bold characters in FIG. 6). All four MiAMP2-like segments of the protein contain 2 doublets of cysteine residues separated by 10–12 residues to give the following pattern C-X-X-X-C-(10–12X)-C-X-X-X-C (SEQ ID NOs:37–39) where X is any amino acid, and C is cysteine. All four segments are expected to form helix-turn-helix motifs as described in Example 8 above. It is clear that the cysteines in these locations will form disulfide bridges that stabilize the structure of the proteins by holding the two helical portions together.

The predicted helix-turn-helix motifs can be further stabilized in several ways. The first method of stabilization is exemplified in segments 1 and 3 (i.e., residues 29–63 and 118–170, respectively, of the 666-residue Macadamia vicilin-like protein). These segments are stabilized by a hydrophobic ring-stacking interaction between two aromatic residues (one on each α-helical segment); this is normally accomplished with tyrosine residues but phenylalanine is also used. As with the cysteine residues, the location of these aromatic residues in the predicted α-helical segments is critical if they are to offer stabilization to the helix-turn-helix structure. In segments 1 and 3, the aromatic residues are 2 and 3 residues removed from the cysteine doublets as shown here: Z-X-X-C-X-X-X-C-(10–12X)-C-X-X-X-C-X-X-X-Z (SEQ ID NOs.:34–36 where C is cysteine and Z is usually tyrosine but can be substituted with phenylalanine as is done in segment 1.

The second way to stabilize the helix-turn-helix fragment is by using an added disulfide bridge as seen in fragment 2 (residues 71–110). This is accomplished by placing additional cysteine residues 2 and 3 residues removed from the cysteine doublets as shown here: nX-C-X-X-C-X-X-X-C-(10–12X)-C-X-X-X-C-X-X-X-C-nX (SEQ ID NOS: 31–33). This is the only report that the inventors know of where a helix-turn-helix domain in an antimicrobial protein is stabilized by three disulfide bridges. While segment 4 (residues 175–241) does not contain the extra disulfide bridge or the hydrophobic ring-stacking stabilization, it is probably stabilized by means of weaker ionic and or hydrogen bonding interactions.

EXAMPLE 10

Vectors for Liquid Culture Expression of MiAMP2 and Homologues

PCR primers flanking the nucleotide region coding for MiAMP2c were engineered to contain restriction sites for Nde I and Bam HI (corresponding to the 5' and 3' ends of the coding region, respectively; Primer JPM31 sequence: 5' A CAC CAT ATG CGA CAA CGT GAT CC 3'; Primer JPM32 sequence: 3' C GTT GTT TTC TCT ATT CCT AGG GTT G 5', SEQ ID NOS: 14 and 15). These primers were then used to amplify the coding region of MiAMP2c DNA. The PCR product from this amplification was then digested with Nde I and Bam HI and ligated into a pET17b vector (Novagen/Studier, F. W. et al. [1986] *J. Mol. Biol.* 189:113) with the coding region in-frame to produce the vector pET17-MiAMP2c.

A similar approach to the one above was used to construct vectors carrying the coding sequences of MiAMP2c homologues (i.e. MiAMP2a, b, and d as well as Tc AMP1, and TcAMP2). To construct the expression vectors for fragments a, b and d in MiAMP2 clone 1, specific PCR primers incorporating the Nde I and Bam HI sites were designed to amplify the fragments of interest. The products were then digested with the appropriate restriction enzymes and ligated into the Nde I/Bam HI sites of a pET16b vector [Novagen] containing a His tag and a Factor Xa cleavage site (amino acid sequence MGHHH HHHHH HHSSG HIEGR HM, SEQ ID NO:16). The protein products expressed from the pET16b vector is a fusion to the antimicrobial protein. The coding sequences for MiAMP2-like subunits from cocoa (FIG. 4, TcAMP1 and TcAMP2) were obtained from the published DNA sequence of the cocoa vicilin gene (Spencer, M. E. and Hodge R. [1992] *Planta* 186:567–576). Two MiAMP2-like fragments within the cocoa vicilin gene were located at the 5' end (corresponding to the residues shown in FIG. 4), and two sets of complimentary oligonucleotides corresponding to the desired coding sequences were designed. The complimentary oligonucleotides (90 to ~100 bases) corresponding to each cocoa subunit contained a 20 bp overlap and also contained the Nde I and Bam HI restriction endonuclease cut sites.

For TcAMP, the following nucleotides were synthesised:

```
TcAMP1 forward oligo  5' GGGAATTCCA TATGTATGAG CGTGATCCTC
                         GACAGCAATA CGAGCAATGC CAGAGGCGAT
                         GCGAGTCGGA AGCGACTGAA GAAAGGGAGC 3';
TcAMP1 reverse oligo  5' GAAGCGACTG AAGAAAGGGA GCAAGAGCAG
                         TGTGAACAAC GCTGTGAAAG GGAGTACAAG
                         GAGCAGCAGA GACAGCAATA GGGATCCACA C 3'.
```

For TcAMP2, the following oligonucleotides were used:

```
TcAMP2         5' GGGAATTCCA TATGCTTCAA AGGCAATACC
forward oligo  AGCAATGTCA AGGGCGTTGT CAAGAGCAAC
               AACAGGGGCA GAGAGAGCAG CAGCAGTGCC
               AGAGAAAATG C 3';
TcAMP2         5' GTGTGGATCC CTAGCTCCTA TTTTTTTTGT
reverse oligo  GATTATGGTA ATTCTCGTGC TCGCCTCTCT
               CTTGTTCCTT ATATTGCTCC CAGCATTTTC
               TCTGGCACTG CT 3'.
```

The oligonucleotide sets were added to individual PCR amplification reactions in order make individual PCR fragments containing the desired coding region. Since initial PCR amplifications gave fuzzy bands, reamplification of the original products was carried out using new 20 mer primers (complimentary to the 5' ends of the forward and reverse oligonucleotides shown above) designed to amplify the entire coding region of the cocoa subunits. Once amplified, the PCR products were restriction digested with the appropriate enzymes and ligated into the vector pET16b as above. This procedure was carried out for both cocoa fragments with similarities to MiAMP2c (shown in FIG. 4).

EXAMPLE 11

Expression in *E. coli* and Purification of MiAMP2c and Homologues

Starter cultures (50 ml) of *E. coli* strain BL21 (Grodberg, J. [1988*] J. Bacteriol.* 170:1245) transformed with the appropriate pET construct (Example 10) were added to 500 ml of NZCYM media (*Current Protocols in Molecular Biology*, supra) and cultured to an optical density of 0.6 (600 nm) and induced with the addition of 0.4 or 1.0 mM IPTG depending on whether pET17b (containing a T7 promoter) or pET16b (containing a His tag fusion and a T7 promoter/lac operator) vector was being used. After cells were induced, cultures were allowed to grow for 4 hours before harvesting. Aliquots of the growing cultures were removed at timed intervals and protein extracts run on an SDS-PAGE gel to follow the expression levels of MiAMP2 and homologues in the cultures. Fragments being expressed with a Histidine tag (i.e., in the pET16b vector), were harvested by centrifuging induced cell cultures at 5000 g for 10 minutes. Cell pellets were resuspended and broken by stirring for one hour in 6 M Guanidine-HCl, buffered with 100 mM sodium phosphate and 10 mM Tris at pH 8.0. Broken cell suspensions were centrifuged at 10,000 g for 20–30 minutes to settle the cellular debris. Supernatants were removed to fresh tubes and 500 mg of Ni-NTA fast flow resin (Qiagen) was added to each supernatant. After gentle mixing at 4° C. for 30–60 minutes, the suspension was loaded into a small column, rinsed two times with 8 M Urea (pH 8.0 and then pH 6.3) and subsequently, the protein was eluted using 8 M Urea pH 4.5. Protein fractions thus obtained were substantially pure but were further purified using an 9.3×250 mm C2/C18 reverse phase column (Pharmacia) and 75 minute gradient from 5% to 50% acetonitrile (0.1% TFA) flowing at 3 ml/min (data not shown).

All of the MiAMP2c homologues (except MiAMP2c which was expressed in pET17b) were expressed in the pET16b vector containing the Histidine tag. While induction of the MiAMP2c culture proceeded as above, the rest of the purification was somewhat different. In this case, MiAMP2c-expressing cells were harvested by centrifugation but were then resuspended in phosphate buffer (100 mM, pH 7.0 containing 10 mM EDTA and 1 mM PMSF) and broken open using a French press instrument. Cellular debris containing MiAMP2c inclusion bodies was solubilized using a 6 M Guanidine-HCl, 10 mM MES pH 6.0 buffer. Soluble material was then recovered after centrifugation to remove insoluble debris remaining from the solubilization step. Guanidine-HCl soluble material was then dialyzed against 10 mM MES pH 6.0 containing PMSF (1 mM) and EDTA (10 mM). Cation-exchange fractionation was carried out as described in Example 3 except on a smaller scale after the dialysis step. Subsequently, the major eluting protein from the cation-exchange column, which was MiAMP2c, was then further purified using reverse phase HPLC as described in Example 3.

Figure 9:
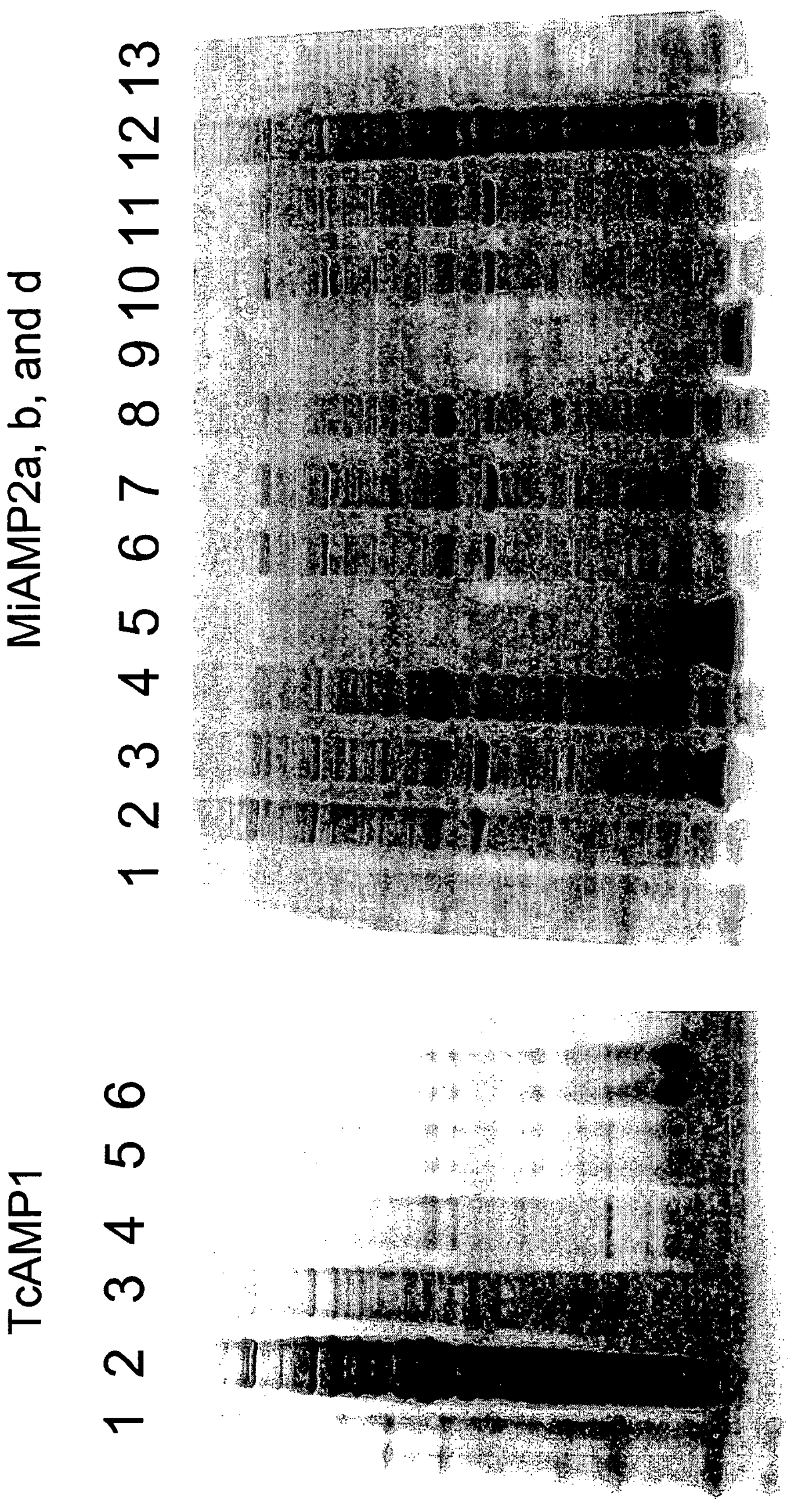
FIG. 9 shows stained SDS-PAGE gels of protein fractions at various stages in the expression and purification of TcAMP1 (Theobroma cacao subunit 1), MiAMP2a, MiAMP2b, MiAMP2c and MiAMP2d expressed in *E. coli* liquid culture.
Figure 10:
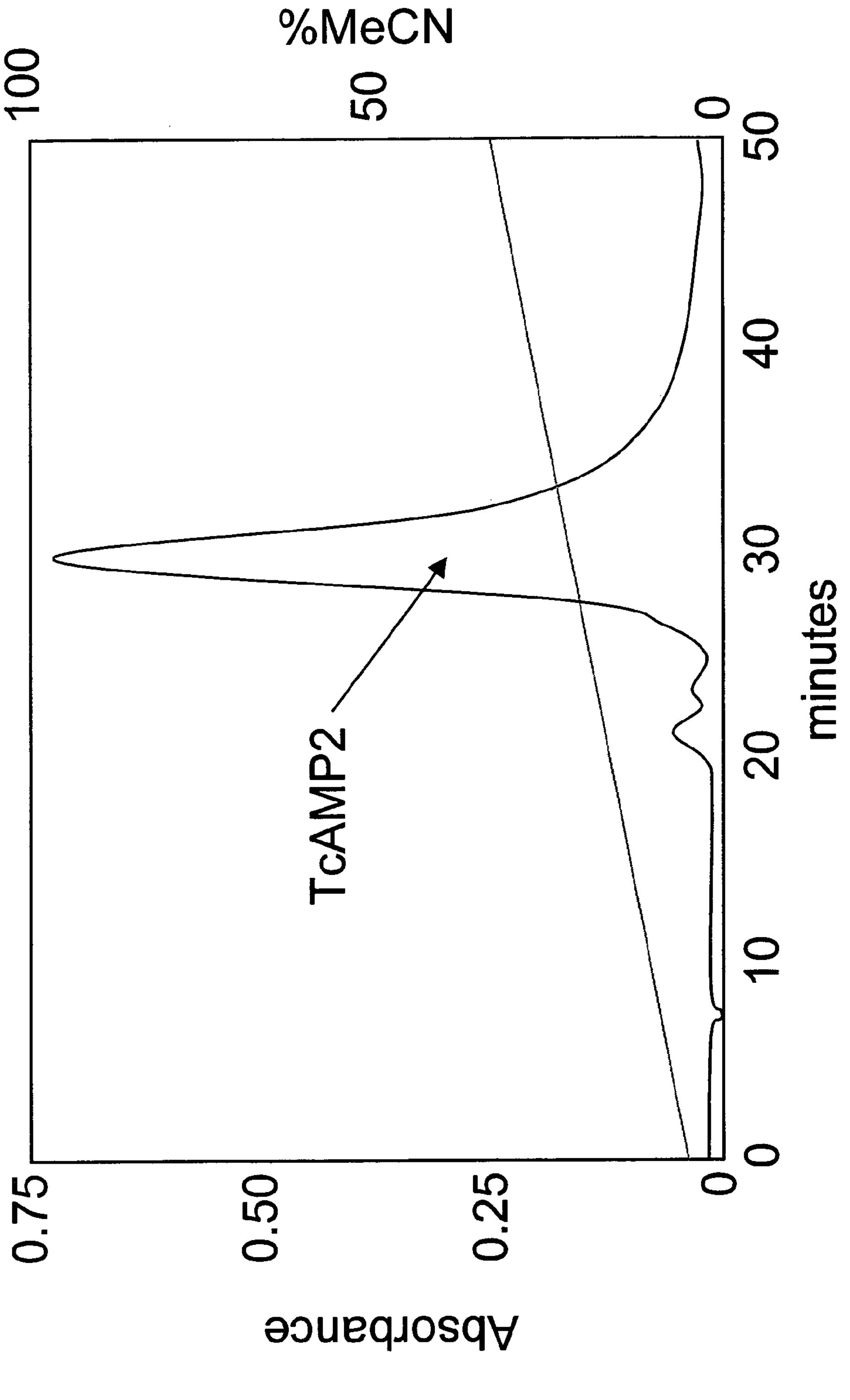
FIG. 10 shows the reverse-phase HPLC purification of cocoa subunit 2 (TcAMP2) after the initial purification step using Ni-NTA media.

FIG. 9 shows the SDS-PAGE gel analysis of the various purification stages obtained following induction with IPTG and subsequent purification of expressed proteins. Samples analysed during the TcAMP1 purification were are as follows: lane 1, molecular weight markers; lane 2, Ni-NTA non-binding fraction; lane 3, rinse of Ni-NTA resin with pH 8 urea; lane 4, rinse of Ni-NTA resin with pH 6.3 urea; lane 5, elution of TcAMP1 with pH 4.5 urea; and lane 6, second elution of TcAMP1 with pH 4.5 urea. TcAMP2 was purified in a similar manner and was also subjected to reverse-phase HPLC to further purify the fraction eluting from the Ni-NTA resin. FIG. 10 shows the reverse phase purification of cocoa subunit number 2 (TcAMP2).

SDS-PAGE gel analysis of the MiAMP2a, b, and d fragment purification is shown in the second panel of FIG. 9. Lane contents are as follows: lane 1, molecular weight markers; lane 2, MiAMP2a pre-induced cellular extract; lane 3, MiAMP2a IPTG induced cellular extract; lane 4, MiAMP2a Ni-NTA non-binding fraction; lane 5, MiAMP2a elution from Ni-NTA; lane 6, MiAMP2b pre-induced cellular extract; lane 7, MiAMP2b IPTG induced cellular extract; lane 8, MiAMP2b Ni-NTA non-binding fraction; lane 9, MiAMP2b elution from Ni-NTA; lane 10, MiAMP2d pre-induced cellular extract; lane 11, MiAMP2d IPTG induced cellular extract; lane 12, MiAMP2d Ni-NTA non-binding fraction; and lane 13, MiAMP2d elution from Ni-NTA.

Using the vectors described in Example 10, MiAMP2c, and 5 homologues (i.e., MiAMP2a, MiAMP2b, MiAMP2d, TcAMP1 and TcAMP2) were all expressed, purified and tested for antimicrobial activity. The approach taken above can be applied to all of the antimicrobial fragments described in FIG. 4. Purified fragments can then be tested for specific inhibition against microbial pathogens of interest.

EXAMPLE 12

Figure 11:
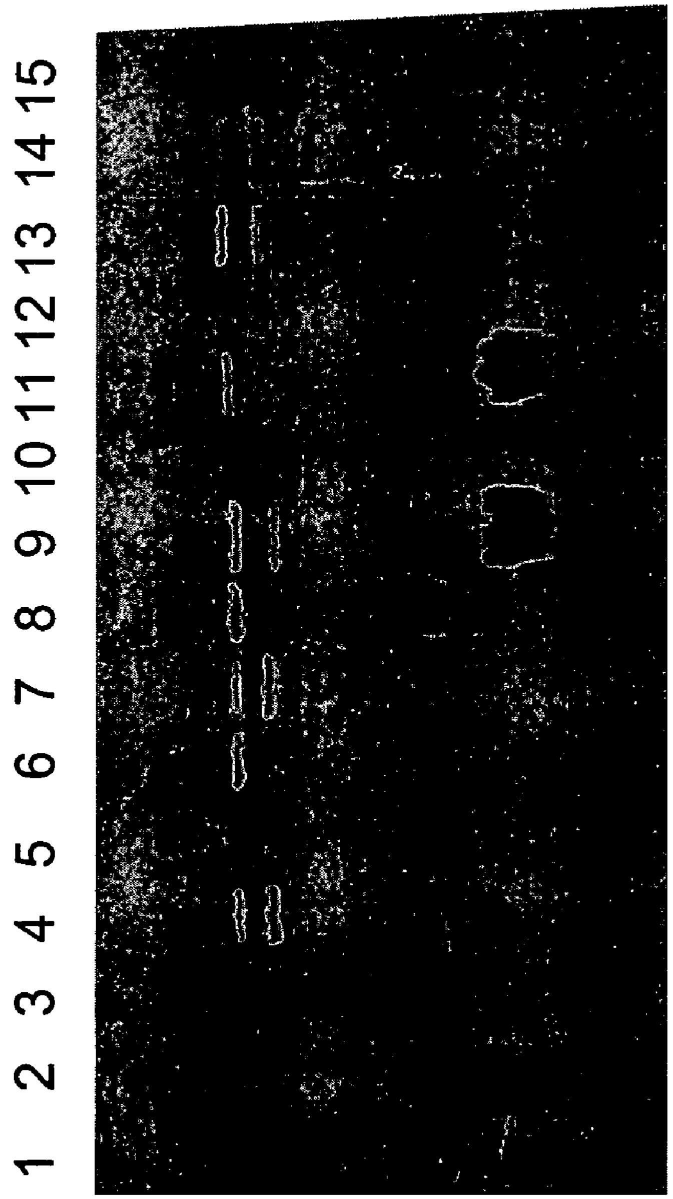
FIG. 11 shows a western blot of crude protein extracts from various plant species using rabbit antiserum raised to MiAMP2c.

Detection of MiAMP2 Homologues in Other Species Using Antibodies Raised to MiAMP2c Rabbits were immunised intramuscularly according to standard protocols with MiAMP2 conjugated to diphtheria toxoid suspended in Fruends incomplete adjuvent. Serum was harvested from the animals at regular intervals after giving the animal added doses of MiAMP2 adjuvent to boost the immune response. Approximately 100 ml of serum were collected and used for screening of crude extracts obtained from several plant seeds. One hundred gram quantities of seeds were ground and extracted to obtain a crude extract as in Example 1. Aliquots of protein were separated on SDS-PAGE gels and the gels were then blotted onto nitrocellulose membrane for subsequent detection of antibody reacting proteins. The membranes were incubated with MiAMP2c rabbit primary antibodies, washed and then incubated with alkaline phosphatase-conjugated goat anti-rabbit IgG for colorimetric detection of antigenic bands using the chemical 5-bromo-4-chloro-3-indolyl phosphate/nitroblue tetrazolium substrate system (Schleicher and Schuell). FIG. 11 shows that various other species contain immunologically-related proteins of similar size to MiAMP2c. Lanes 1–15 contain the extracts from the following species: 1) *Stenocarpus sinuatus,* 2) *Stenocarpus sinuatus* (1/10 loading), 3) *Restio tremulus,* 4) *Mesomalaena tetragona,* 5) *Nitraria billardieri,* 6) *Petrophile canescens,* 7) *Synaphae acutiloba,* 8) *Dryandra formosa,* 9) *Lambertia inermis,* 10) *Stirlingia latifolia,* 11) *Xylomelum angustifolium,* 12) *Conospermum bracteosuin,* 13) *Conospermum triplinernium,* 14) Molecular weight marker, 15) *Macacamia integrifolia* pure MiAMP2c. Lanes 1–13 contain a variety of species, some of which show the presence of antigenically related proteins of a similar size to MiAMP2c. Other bands exhibiting higher molecular weights probably represent the larger precursor seed storage proteins from which the antimicrobial proteins are derived. Antigenically-related proteins can be seen in lanes 1, 2, 4, 6, 7, 8, 9, and 11–13.

Bioassays were also performed using crude extracts from various Proteaceae species. Specifically, extracts from *Banksia robur, Banksia canei, Hakea gibbosa, Stenocarpus sinuatus*, and *Stirlingia latifolia* have all been shown to exhibit antimicrobial activity. This activity may derive from MiAMP2 homologues since these species are related to Macadamia.

EXAMPLE 13

Purification of MiAMP2c Homologues in Another Species Using Antibodies Raised to MiAMP2c Based on the detection of immunologically related proteins in other species of the family Proteaceae and the presence of antimicrobial activity in crude extracts, *Stenocarpus sinuatis* was chosen for a large scale fractionation experiment in an attempt to isolate MiAMP2c homologues. Five kg of *S. sinuatus* seed was frozen in liquid nitrogen and ground in a food processor (Big Oscaar Sunbeam). The ground seed was immediately placed into 12 L of 50 mM $H_2SO_4$ extraction buffer and extracted at 4° C. for 1 hour with stirring. The slurry was then centrifuged for 20 min at 10,000 g to remove particulate matter. The supernatant was then adjusted to pH 9 using a 50 mM ammonia solution. PMSF and EDTA were added to final concentrations of 1 and 10 mM respectively.

The crude protein extract was applied to an anion exchange column (Amberlite IRA-938, Rohm and Haas) (3 cm×90 cm) equilibrated with 50 mM $NH_4Ac$ pH 9.0 at a flow rate of 40 ml/min. The unbound protein comprising the basic protein fraction was collected and used in the subsequent purification steps.

The basic protein fraction was adjusted to pH 5.5 with acetic acid and then applied at 10 ml/minute over 12 h to a SP-Sepharose Fast Flow (Pharmacia) Column (5 cm×60 cm) pre-equilibrated with 25 mM ammonium acetate. The column was then washed for 3.5 h with 25 mM Acetate pH 5.5. Elution of bound proteins was achieved by applying a linear gradient of $NH_4Ac$ from 25 mM to 2.0 M (pH 5.5) at 10 ml/min over 10 h. Absorbance of the eluate was observed at 280 nm and 100 ml fractions collected (see FIG. 12).

Cation-exchange fractions that cross-reacted with the antiserum (fractions 14–28, FIG. 12) were then further purified by reverse phase chromatography. Cross-reacting fractions were loaded onto a 7 μm C18 reverse phase column (Brownlee) equilibrated with 90% $H_2O$, 10% acetonitrile and 0.1% Trifluoroacetic acid (TFA) (=100% A). Bound proteins were eluted with a linear gradient from 100% A to 100% B (5% H2O, 95% acetonitrile, 0.08% TFA). The absorbance of the eluted proteins was monitored at 214 nm and 280 nm. The eluted proteins were dried under vacuum and resuspended in water three times to remove traces of TFA from the samples. Reverse phase protein elution fractions 20 to 61 were analysed by pooling 2 adjacent fractions and performing a western blot analysis (see FIG. 13). Fractions 22–41 gave a weak positive reaction and fractions 42–57 gave a strong positive reaction to the anti-MiAMP2c antiserum. Fractions that showed antifungal activity against *S. sclerotiorum* at 50 μg/ml and 10 μg/ml are indicated by arrows on the chromatogram.

Using the approach above, several active fractions (termed SsAMP1 and SsAMP2) were obtained which were assessed for their antifungal activity against *Sclerotinia sclerotiorum, Alternaria brassicola, Leptosphaeria maeulans, Verticilium dahlias* and *Fusarium oxysporum*. Bioassays were carried out as described in Example 2 and results shown in Example 15. Another fragment which reacted with MiAMP2 antiserum was purified and sequenced (SsAMP3) but insufficient protein was available for characterisation of antimicrobial activity. Partial sequences obtained from these proteins are shown in FIG. 4 (SEQ ID NOS: 26, 27 and 28). Full sequencing of the peptides or cloning of cDNAs encoding the seed storage proteins from this species will reveal the extent of homology between these peptides and MiAMP2-series homologues.

EXAMPLE 14

Synthesis of Small Fragments of MiAMP2c

In an effort to determine if the full MiAMP2c molecule was absolutely necessary for the protein to exhibit antimicrobial activity, two separate peptides were chemically synthesized by Auspep Pty. Ltd. (Australia). For each peptide, the cysteine residues were changed to alanine residues so that disulfide bonds were no longer capable of being formed between two separate protein chains. Tyrosine residues were also changed to alanine since it was expected that tyrosine also participated in the helix-turn-helix stabilization and this would not be needed in the synthetic peptides lacking one of the helices. Alanine is also favorable to the formation of alpha-helices so it bshould not interfere with the native helical structure to a large degree. Peptide one is comprised of 22 amino acids from 118 to 139 in the amino acid sequence of clone 3 (sequence: RQRDP QQQAE QAQKR AQRRE TE, SEQUENCE ID NO:9). Peptide 2 is 25 amino acids in length and runs from 140 to 164 in clone 3 (sequence: PRHMQ IAQQR AERRA EKEKR KQQKR, SEQ ID NO:10). Peptides 1 and 2 are labeled MiAMP2c pep1 and MiAMP2c pep2 respectively. These peptides were resuspended in Milli-Q water and bioassayed against a number of fungi. As seen in Table 2, peptide 2 has inhibitory activity against a variety of fungi whereas peptide 1 exhibited little or no activity. Mixtures of peptide 1 and peptide 2 exhibit similar levels of activity as seen with peptide 2 alone indicating that only peptide 2 is exhibiting activity. The fact that peptide 2 exhibits antimicrobial activity in the absence of the helix-turn-helix structure exhibited by MiAMP2c reveals that the helix-turn-helix structure is not absolutely necessary for the peptides to retain activity. Nevertheless, peptide 2 did not exhibit the same degree of activity on a molar basis as MiAMP2c (whole fragment) indicating that the helix-turn-helix structure is important for maximal expression of antimicrobial activity by the fragments involved. It is also expected that the helix-turn-helix structure will confer greater stability to the MiAMP2 homologues, thus rendering these proteins less susceptible to proteolytic cleavage and other forms of degredation. Greater stability would lead to maintaining antimicrobial activity over a longer period of time.

EXAMPLE 15

Antifungal Activity of MiAMP2c Homologues and Fragment(s)

MiAMP2c and each of the various MiAMP2 homologues were tested against a variety of fungi as concentrations ranging from 2 to 50 μg/ml. Table 1 shows the $IC_{50}$ value of pure MiAMP2c against various fungi and bacteria. In the table, the ">50" indicates that 50% inhibition of the fungus was not achieved at 50 μg/ml which was the highest concentration tested. The abbreviation "ND" indicates that the test was not performed or that results could not be interpreted. The antimicrobial activity of MiAMP2c was also tested in the presence of 1 mM $Ca^{2+}$ in the test medium and the $IC_{50}$ values for these tests are given in the right-hand column. As can be seen in the table, the inhibitory activity of MiAMP2c is greatly reduced (although not eliminated) in the presence of $Ca^{2+}$.

TABLE 1

Concentrations of MiAMP2c at which 50% inhibition of growth was observed

| Organism | $IC_{50}$ (μg/ml) | $IC_{50}$ + $Ca^{2+}$ (μg/ml) |
|---|---|---|
| *Alternaria helianthi* | 5–10 | ND |
| *Candida albicans* | >50 | >50 |
| *Ceratocystis paradoxa* | 20–50 | >50 |
| *Cercospora nicotianae* | 5–10 | 5–10 |
| *Clavibacter michiganensis* | 50 | >50 |
| *Chalara elegans* | 2–5 | 10–20 |
| *Fusarium oxysporum* | 10 | 20–50 |
| *Sclerotinia sclerotiorum* | 20–50 | >50 |
| *Phytophthora cryptogea* | 5–10 | 10–25 |
| *Phytophthora parasitica nicotiana* | 10–20 | >50 |
| *Verticillium dahliae* | 5–10 | >50 |
| *Ralstonia solanacearum* | >50 | >50 |
| *Pseudomonas syringae tabaci* | >50 | >50 |
| *Saccharomyces cerevisiae* | 20–50 | >50 |
| *Escherichia coli* | >50 | >50 |

Table 2 shows the the antimicrobial activity of various homologues and fragments of MiAMP2c. In the table, the following abbreviations are used: Ab, *Altern aria brassicola;* Cp: *Ceratocystis paradoxa;* Foc: *Fusarium oxysporum;* Lm: *Leptosphaeria maculans;* Ss: *Scierotinia sclerotiorum;* Vd: *Verticillium dahlias*. The ">50" indicates that concentrations higher than 50 μg/ml were not tested so that an $IC_{50}$ value could not be established. A blank space indicates that the test was not performed or that results could not be interpreted.

The TcAMP1 and 2 used for the results presented in Table 2 were derived from cocoa vicilin (Examples 10 and 11). SsAMP1 and 2 show reactivity with MiAMP2c antibodies and also exhibit antimicrobial activity as seen in the table below. The versions of MiAMP2a, b and d as well as TcAMP1 and TcAMP2 tested in the bioassays all contain a His tag fusion resulting from expression in the vector pET16b. MiAMP2c pep1 and 2 are the N and C terminal regions, respectively, of MiAMP2c antimicrobial peptide as specified in Example 14 above. The concentration value listed for 'MiAMP2c pep1+2' is the concentration of each individual peptide in the mixture. It should be remembered that MiAMP2c pep1 and pep2 are both about ½ the size of MiAMP2c; comparisons of the activity of these peptides with the MiAMP2c protein should, therefore, be made on a molar basis rather than on a strict μg/ml concentration basis. Peptides were only tested in media A which did not contain added $Ca^{2+}$.

TABLE 2

$IC_{50}$ values (μg/ml) of MiAMP2 related proteins against various fungi

| Peptide tested | Fungus used in bioassy | | | | | |
|---|---|---|---|---|---|---|
| | Ab | Cp | Foc | Lm | Ss | Vd |
| MiAMP2a | | | 5–10 | 2.5–5 | 5–10 | |
| MiAMP2b | | | 2.5 | 2.5 | 5–10 | |
| MiAMP2c | | 20–50 | 10 | | 20–50 | 5–10 |
| MiAMP2d | | | 5 | 2.5 | 5–10 | |
| MiAMP2c pep1 | | | 100<br>31 | | >50 | |
| MiAMP2c pep2 | | | 10–20 | 10–20 | 50 | 10–20 |
| MiAMP2c pep1 + 2 | | | 10–25 | | 50 | |
| TcAMP1 | | 10 | 5–10 | 2–5 | 10 | 5–20 |
| TcAMP2 | | 5–10 | 5–10 | 2–5 | 5 | 5–20 |
| SsAMP1 | | | 20–50 | 20–50 | 20–50 | 10–20 |
| SsAMP2 | 20–50 | | >50 | >50 | >50 | >50 |

It is worthy of note that while the TcAMP1 and 2 sequences are readily available in the public data bases, no antimicrobial activity had ever been assigned to them. These sequences were derived from much larger proteins involved in seed storage functions. The inventors have thus described a completely new activity for a small portion of the overall cocoa vicilin molecules. The activity of cotton fragments 1, 2, and 3 has been exemplified by other authors (Chung, R. P. T. et al. [1997] *Plant Science* 127:1–16).

EXAMPLE 16

Construction of the Plant Transfomation Vector PCV91-MiAMP2c

Figure 12:
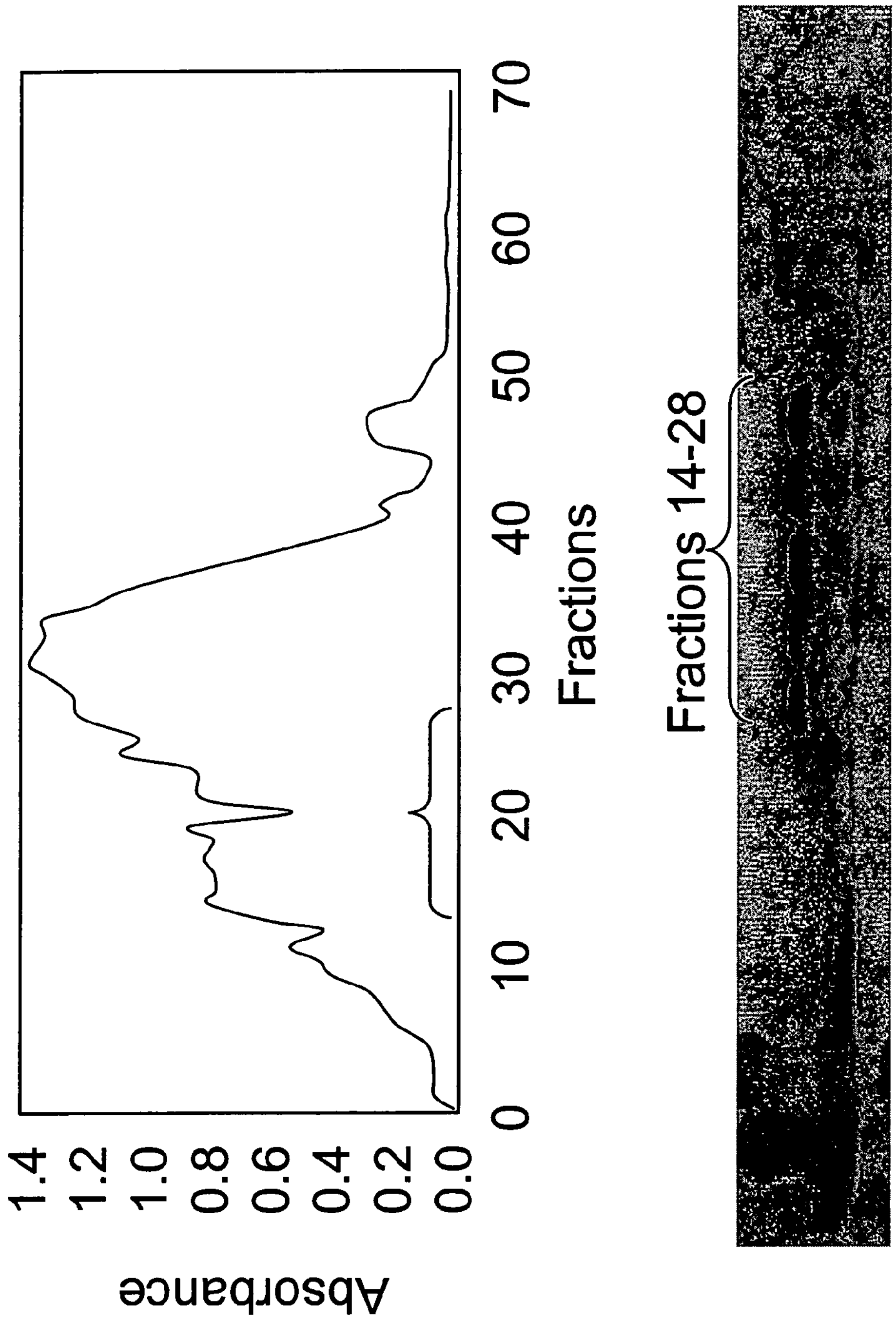
FIG. 12 shows a cation-exchange fractionation of the *Stenocarpus sinuatus* basic protein fraction along with the accompanying western blot which shows the presence of immunologically-related proteins in a range of fractions.
Figure 13:
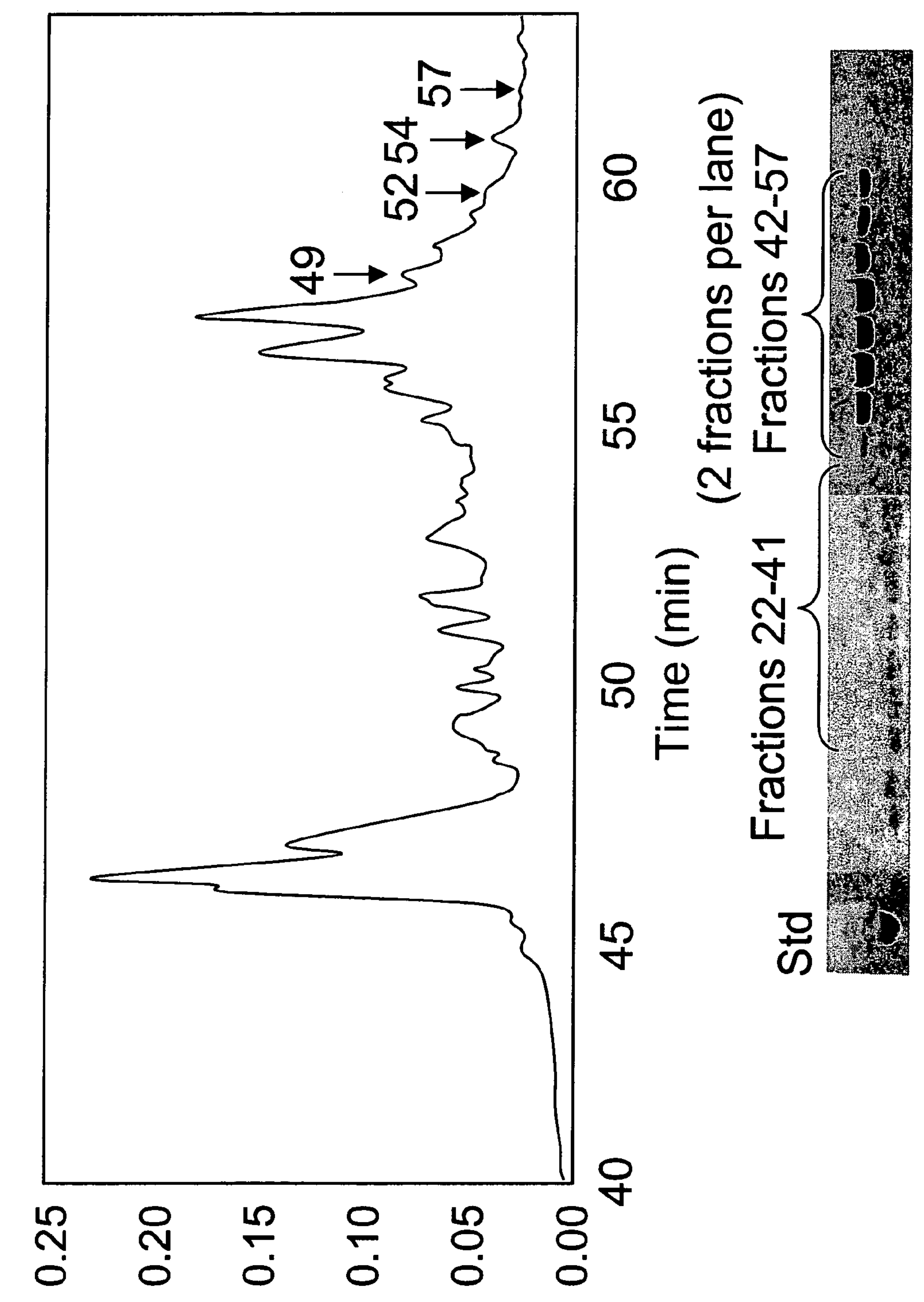
FIG. 13 shows a reverse-phase HPLC separation of *Stenocarpus sinuatus* cation-exchange fractions which had previously reacted with MiAMP2c antibodies (see FIG. 14). A western blot is also presented which reveals the presence of putative MiAMP2c homologues in individual HPLC fractions.
Figure 14:
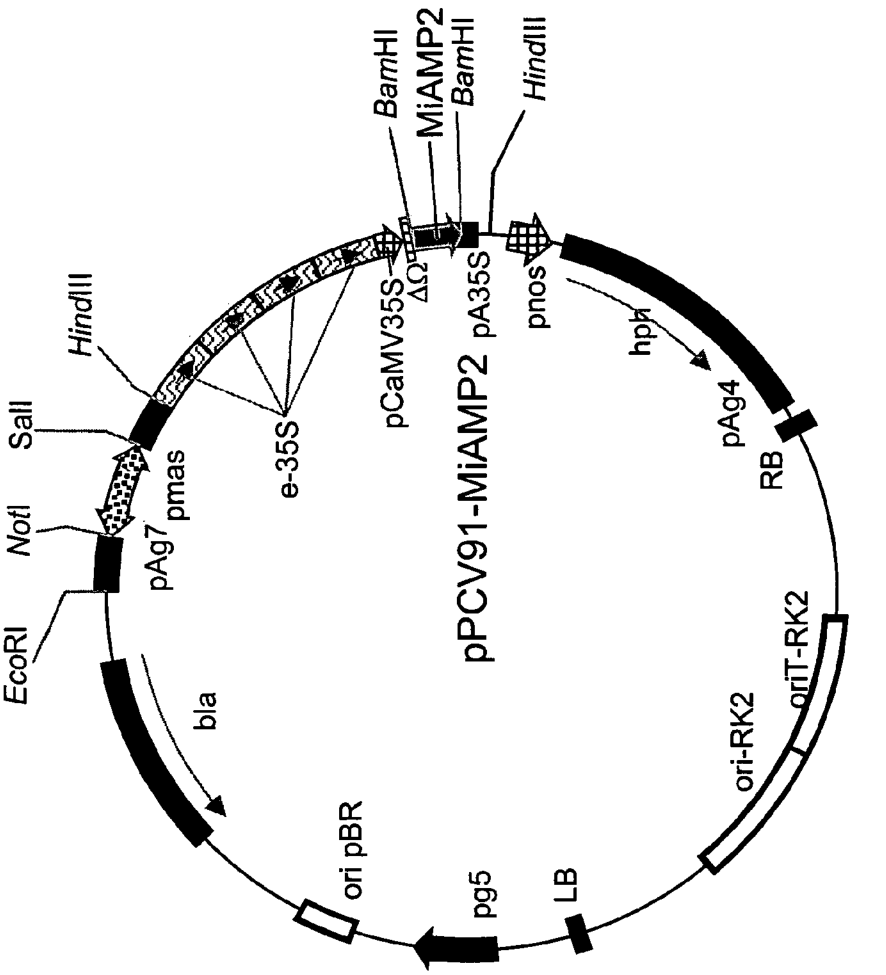
FIG. 14 is a map of the binary vector pPCV91-MiAMP2c as an example of a vector that can be used to express these antimicrobial proteins in transgenic plants.

The expression vector pPCV91-MiAMP2c (FIG. 14) contains the full coding region of the MiAMP2c (Example 7) DNA flanked at it 5' end by the strong constitutive promoter of 35S RNA from the cauliflower mosaic virus (pCaMV35S) (Odel et al., [1985] *Nature* 313: 810–812) with a quadruple-repeat enhancer element (e-35S) to allow for high transcriptional activity (Kay et al. [1987] *Science* 236:1299–1302). The coding region of MiAMP2c DNA is flanked at its 3' end by the polyadenylation sequence of 35S RNA of the cauliflower mosaic virus (pA35S). The plasmid backbone of this vector is the plasmid pPCV91 (Walden, R. et al. [1990] *Methods Mol. Cell. Biol.* 1:175–194). The plasmid also contains other elements useful for plant transformation such as an ampicillin resistance gene (bla) and a hygromycin resistance gene (hph) driven by the nos promoter (pnos). These and other features allow for selection in various cloning and transformation procedures. The plasmid pPCV91-MiAMP2c was constructed as follows: A cloned fragment encoding MiAMP2c (Example 7) was digested using restriction enzymes to release the MiAMP2c gene fragment containing a synthetic leader sequence. The binary vector pPCV91 was digested with the restriction enzyme Bam HI. Both the MiAMP2c DNA fragment containing and the binary vector were ligated using T4 DNA ligase to produce pPCV91-MiAMP2c binary vector for plant transformation (FIG. 12).

Using this approach, other homologues of MiAMP2c can be expressed in plants. Not only can individual homologues be expressed, but they may be expressed in combination with other proteins as fusion proteins or as portions of larger precursor proteins. For example, it is possible to express the N-terminal region of MiAMP2 clone 1 (amino acids 1 to ~246) which contains a signal peptide and the hydrophilic region containing four antimicrobial segments. Transgenic plants can then be assessed to examine whether the individual fragments are being processed into the expected fragments by the processing machinery already present in the plant cells. It is also possible to express the entire MiAMP2 clone 1 (amino acids 1 to 666) and to examine the processing of the entire protein when expressed in transgenic plants. Homologous regions from other sequences can also be used in multiple combinations with, for example, ten (10) or more MiAMP2-like fragments expressed as one large fusion protein with acidic cleavage sites located as proper locations between each of the fragments. As well as linking MiAMP2 fragments together, it would also be possible to link MiAMP2 fragments to other useful proteins for expression in plants.

EXAMPLE 17

Transgenic Plants Expressing MiAMP2c (or Related Fragments)

The disarmed *Agrobacterium tumefaciens* strain GV3101 (pMP90RK) (Koncz, Cs. [1986*] Mol. Gen. Genet.* 204: 383–396) was transformed with the vector pPCV91 -MiAMP2c (Example 16) using the method of Walkerpeach et al. (Plant Mol. Biol. Manual B1:1–19 [1994]) adapted from Van Haute et al (*EMBO J.* 2:411–417 1983]).

Figure 15:
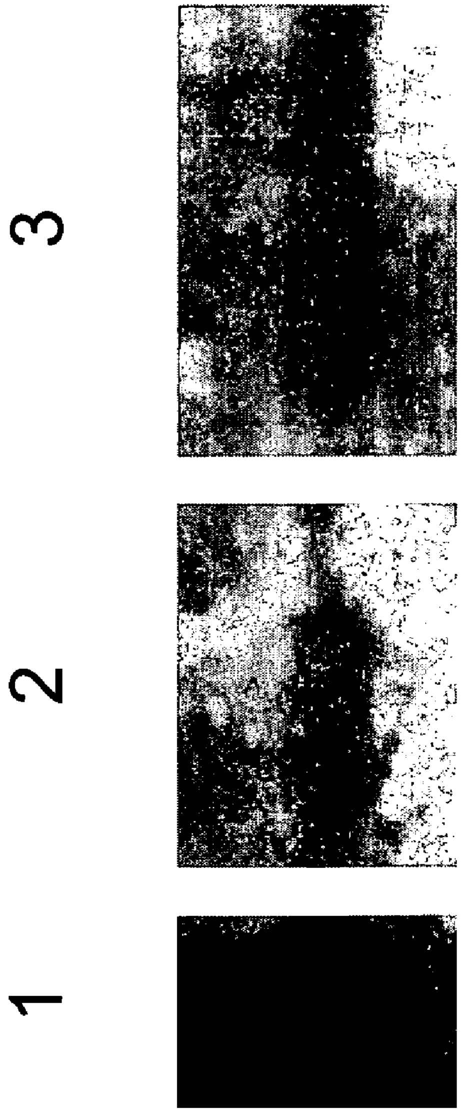
FIG. 15 shows a western blot to detect MiAMP2c expressed in transgenic tobacco plants.

Tobacco transformation was carried out using leaf discs of *Nicotiana tabacum* based on the method of Horsch et al. (*Science* 227:1229–1231 [1985]) and co-culturing strains containing pPCV91-MiAMP2c. After co-cultivation of *Agrobacterium* and tobacco leaf disks, transgenic plants (transformed with pPCV91-MiAMP2c) were regenerated on media containing 50 μg/ml hygromycin and 500 μg/ml Cefotaxime. These transgenic plants were analysed for expression of the newly-introduced genes using standard western blotting techniques (FIG. 15). FIG. 15 shows a western blot of extracts from trangenic tobacco carrying the construct for MiAMP2c from example 16. Lane 1 contains pure MiAMP2c as a standard, lanes 2 and 3 contain extracts from transgenic plants carrying the pPCV91-MiAMP2c construct. As can be see in the figure, faint bands are present at approximately the correct molecular weight, indicating that the transgenic plants appear to be expressing the MiAMP2c protein. Plants capable of constitutive expression of the introduced genes may be selected and self-pollinated to give seed. F1 seedlings of the transgenic plants may be further analysed.

EXAMPLE 18

MiAMP2c Homologues

Every homologue of MiAMP2c that has been tested has exhibited some antimicrobial activity. This evidence indicates that other homologues will also exhibit antimicrobial activity. These homologues include fragments from 1) peanut (Burks, A. W. et al. [1995*] J. Clin. Invest.* 96 (4), 1715–1721), 2) maize (Belanger, F. C. and Kriz, A. L. [1991*] Genetics* 129 (3), 863–872), 3) barley (Heck, G. R. et al. [1993*] Mol. Gen. Genet.* 239 (1–2), 209–218), and 4) soybean (Sebastiani, F. al. [1990*] Plant Mol. Biol.* 15 (1), 197–201). (see SEQ ID NOS: 21, 22, 24, and 25). Other sequences derived from seed storage proteins of the 7S class are also expected to yield homologues of MiAMP2 proteins.

The invention claimed is:

1. An isolated or purified protein fragment having antimicrobial activity, wherein said protein fragment is a polypeptide consisting of the sequence, C-3X-C-nX-C-3X-C (SEQ ID NOS: 38 and 39), wherein n is 11 or 12, X is any amino acid residue other than cysteine, and C is cysteine.

2. An isolated or purified protein having antimicrobial activity and having a sequence selected from the group consisting of SEQ ID NO:1, SEQ ID NO:3, and SEQ ID NO:5.

3. A composition comprising the protein fragment of claim 1 together with an agriculturally-acceptable carrier diluent or excipient.

4. A composition comprising the protein fragment of claim 1 together with a pharmaceutically-acceptable carrier diluent or excipient.

5. An isolated or purified protein fragment having antimicrobial activity, wherein said protein fragment is a polypeptide consisting of the sequence Z-2X-C-3X-C-(10–12) X-C-3X-C-3X-Z (SEQ ID NOS: 34–36)), wherein X is any amino acid residue other than cysteine, and C is cysteine, and Z is tyrosine or phenylalanine.

6. An isolated or purified protein fragment having antimicrobial activity, wherein said protein fragment is a polypeptide consisting of the sequence C-2X-C-3X-C-(10–12)X-C-3X-C-3X-C (SEQ ID NOS: 31–33), wherein X is any amino acid residue other than cysteine, and C is cysteine.

7. An isolated or purified protein fragment having antimicrobial activity, wherein said protein fragment is selected from the group consisting of:

residues 29 to 73 of SEQ ID NO:1
residues 74 to 116 of SEQ ID NO:1
residues 117 to 185 of SEQ ID NO:1
residues 186 to 248 of SEQ ID NO:1
residues 29 to 73 of SEQ ID NO:3
residues 74 to 116 of SEQ ID NO:3
residues 117 to 185 of SEQ ID NO:3
residues 186 to 248 of SEQ ID NO:3
residues 33 to 75 of SEQ ID NO:5
residues 76 to 144 of SEQ ID NO:5
residues 145 to 210 of SEQ ID NO:5
residues 34 to 80 of SEQ ID NO:7
residues 81 to 140 of SEQ ID NO:7
residues 33 to 79 of SEQ ID NO:8
residues 80 to 119 of SEQ ID NO:8
residues 120 to 161 of SEQ ID NO:8
residues 32 to 91 of SEQ ID NO:21
residues 25 to 84 of SEQ ID NO:22
residues 29 to 94 of SEQ ID NO:24; and
residues 31 to 85 of SEQ ID NO:25.

8. A composition comprising the protein fragment of claim 7 together with an agriculturally-acceptable carrier diluent or excipient.

9. A composition comprising the protein fragment of claim 7 together with a pharmaceutically-acceptable carrier, diluent or excipient.

10. A method of reducing the number of microbes infesting a plant, the method comprising administering to said plant an effective amount of the composition of claim 3 for a period sufficient to reduce the number of said microbes.

11. A method of controlling microbial infestation of a mammal, the method comprising treating the mammal with a composition according to claim 4.

12. The method of claim 11, wherein said mammal is a human.

13. A method of controlling microbial infestation of a mammal, the method comprising treating the mammal with a composition according to claim 8.

14. The method of claim 13, wherein said mammal is a human.

15. A method of reducing the number of microbes infesting a plant, the method comprising administering to said plant an effective amount of the composition of claim 8 for a period sufficient to reduce the number of said microbes.

16. A composition comprising the isolated or purified protein of claim 2 together with an agriculturally-acceptable carrier diluent or excipient.

17. A method of reducing the number of microbes infesting a plant, the method comprising administering to said plant an effective amount of the isolated or purified protein of claim 2 for a period sufficient to reduce the number of said microbes.

18. A method of reducing the number of microbes infesting a plant, the method comprising administering to said plant an effective amount of the protein fragment of claim 5 for a period sufficient to reduce the number of said microbes.

19. A method of reducing the number of microbes infesting a plant, the method comprising administering to said plant an effective amount of the protein fragment of claim 6 for a period sufficient to reduce the number of said microbes.

20. A method of reducing the number of microbes infesting a plant, the method comprising administering to said plant an effective amount of the protein fragment of claim 7 for a period sufficient to reduce the number of said microbes.

21. A method of reducing the number of microbes infesting a plant, the method comprising administering to said plant an effective amount of the composition of claim 16 for a period sufficient to reduce the number of said microbes.

22. The method of claim 18, wherein said microbe is a fungus.

23. The method of claim 19, wherein said microbe is a fungus.

* * * * *

SEQUENCE LISTING

```
<160> NUMBER OF SEQ ID NOS:  40

<210> SEQ ID NO 1
<211> LENGTH: 666
<212> TYPE: PRT
<213> ORGANISM: Macadamia integrifolia

<400> SEQUENCE: 1

Met Ala Ile Asn Thr Ser Asn Leu Cys Ser Leu Leu Phe Leu Leu Ser
 1              5                   10                  15

Leu Phe Leu Leu Ser Thr Thr Val Ser Leu Ala Glu Ser Glu Phe Asp
            20                  25                  30

Arg Gln Glu Tyr Glu Glu Cys Lys Arg Gln Cys Met Gln Leu Glu Thr
        35                  40                  45

Ser Gly Gln Met Arg Arg Cys Val Ser Gln Cys Asp Lys Arg Phe Glu
    50                  55                  60

Glu Asp Ile Asp Trp Ser Lys Tyr Asp Asn Gln Glu Asp Pro Gln Thr
65                  70                  75                  80

Glu Cys Gln Gln Cys Gln Arg Arg Cys Arg Gln Gln Glu Ser Gly Pro
                85                  90                  95

Arg Gln Gln Gln Tyr Cys Gln Arg Arg Cys Lys Glu Ile Cys Glu Glu
            100                 105                 110

Glu Glu Glu Tyr Asn Arg Gln Arg Asp Pro Gln Gln Gln Tyr Glu Gln
        115                 120                 125
```

-continued

```
Cys Gln Lys His Cys Gln Arg Arg Glu Thr Glu Pro Arg His Met Gln
    130                 135                 140

Thr Cys Gln Gln Arg Cys Glu Arg Arg Tyr Glu Lys Glu Lys Arg Lys
145                 150                 155                 160

Gln Gln Lys Arg Tyr Glu Glu Gln Gln Arg Glu Asp Glu Glu Lys Tyr
                165                 170                 175

Glu Glu Arg Met Lys Glu Glu Asp Asn Lys Arg Asp Pro Gln Gln Arg
            180                 185                 190

Glu Tyr Glu Asp Cys Arg Arg Arg Cys Glu Gln Gln Glu Pro Arg Gln
        195                 200                 205

Gln His Gln Cys Gln Leu Arg Cys Arg Glu Gln Gln Arg Gln His Gly
    210                 215                 220

Arg Gly Gly Asp Met Met Asn Pro Gln Arg Gly Gly Ser Gly Arg Tyr
225                 230                 235                 240

Glu Glu Gly Glu Glu Glu Gln Ser Asp Asn Pro Tyr Tyr Phe Asp Glu
                245                 250                 255

Arg Ser Leu Ser Thr Arg Phe Arg Thr Glu Glu Gly His Ile Ser Val
            260                 265                 270

Leu Glu Asn Phe Tyr Gly Arg Ser Lys Leu Leu Arg Ala Leu Lys Asn
        275                 280                 285

Tyr Arg Leu Val Leu Leu Glu Ala Asn Pro Asn Ala Phe Val Leu Pro
    290                 295                 300

Thr His Leu Asp Ala Asp Ala Ile Leu Leu Val Ile Gly Gly Arg Gly
305                 310                 315                 320

Ala Leu Lys Met Ile His His Asp Asn Arg Glu Ser Tyr Asn Leu Glu
                325                 330                 335

Cys Gly Asp Val Ile Arg Ile Pro Ala Gly Thr Thr Phe Tyr Leu Ile
            340                 345                 350

Asn Arg Asp Asn Asn Glu Arg Leu His Ile Ala Lys Phe Leu Gln Thr
        355                 360                 365

Ile Ser Thr Pro Gly Gln Tyr Lys Glu Phe Phe Pro Ala Gly Gly Gln
    370                 375                 380

Asn Pro Glu Pro Tyr Leu Ser Thr Phe Ser Lys Glu Ile Leu Glu Ala
385                 390                 395                 400

Ala Leu Asn Thr Gln Thr Glu Lys Leu Arg Gly Val Phe Gly Gln Gln
                405                 410                 415

Arg Glu Gly Val Ile Ile Arg Ala Ser Gln Glu Gln Ile Arg Glu Leu
            420                 425                 430

Thr Arg Asp Asp Ser Glu Ser Arg His Trp His Ile Arg Arg Gly Gly
        435                 440                 445

Glu Ser Ser Arg Gly Pro Tyr Asn Leu Phe Asn Lys Arg Pro Leu Tyr
    450                 455                 460

Ser Asn Lys Tyr Gly Gln Ala Tyr Glu Val Lys Pro Glu Asp Tyr Arg
465                 470                 475                 480

Gln Leu Gln Asp Met Asp Leu Ser Val Phe Ile Ala Asn Val Thr Gln
                485                 490                 495

Gly Ser Met Met Gly Pro Phe Phe Asn Thr Arg Ser Thr Lys Val Val
            500                 505                 510

Val Val Ala Ser Gly Glu Ala Asp Val Glu Met Ala Cys Pro His Leu
        515                 520                 525

Ser Gly Arg His Gly Gly Arg Gly Gly Gly Lys Arg His Glu Glu Glu
    530                 535                 540

Glu Asp Val His Tyr Glu Gln Val Arg Ala Arg Leu Ser Lys Arg Glu
```

-continued 545 550 555 560

Ala Ile Val Val Leu Ala Gly His Pro Val Val Phe Val Ser Ser Gly
565 570 575

Asn Glu Asn Leu Leu Leu Phe Ala Phe Gly Ile Asn Ala Gln Asn Asn
580 585 590

His Glu Asn Phe Leu Ala Gly Arg Glu Arg Asn Val Leu Gln Gln Ile
595 600 605

Glu Pro Gln Ala Met Glu Leu Ala Phe Ala Ala Pro Arg Lys Glu Val
610 615 620

Glu Glu Ser Phe Asn Ser Gln Asp Gln Ser Ile Phe Phe Pro Gly Pro
625 630 635 640

Arg Gln His Gln Gln Gln Ser Pro Arg Ser Thr Lys Gln Gln Gln Pro
645 650 655

Leu Val Ser Ile Leu Asp Phe Val Gly Phe
660 665

<210> SEQ ID NO 2
<211> LENGTH: 2171
<212> TYPE: DNA
<213> ORGANISM: Macadamia integrifolia
<220> FEATURE:
<221> NAME/KEY: sig_peptide
<222> LOCATION: (1)...(85)
<221> NAME/KEY: mat_peptide
<222> LOCATION: (86)...(1999)

<400> SEQUENCE: 2
atggcgatca atacatcaaa tttatgttct cttctctttc tcctttcact cttccttctg 60
tctacgacag tgtctcttgc tgaaagtgaa tttgacaggc aggaatatga ggagtgcaaa 120
cggcaatgca tgcagttgga gacatcaggc cagatgcgtc ggtgtgtgag tcagtgcgat 180
aagagatttg aagaggatat agattggtct aagtatgata accaagagga tcctcagacg 240
gaatgccaac aatgccagag gcgatgcagg cagcaggaga gtggcccacg tcagcaacaa 300
tactgccaac gacgctgcaa ggaaatatgt gaagaagaag aagaatataa ccgacaacgt 360
gatccacagc agcaatacga gcaatgtcag aagcactgcc aacggcgcga gacagagcca 420
cgtcacatgc aaacatgtca acaacgctgc gagaggagat atgaaaagga gaaacgtaag 480
caacaaaaga gatatgaaga gcaacaacgt gaagacgaag agaaatatga agagcgaatg 540
aaggaagaag ataacaaacg cgatccacaa caaagagagt acgaagactg ccggaggcgc 600
tgcgaacaac aggagccacg tcagcagcac cagtgccagc taagatgccg agagcagcag 660
aggcaacacg gccgaggtgg cgatatgatg aaccctcaga ggggaggcag cggcagatac 720
gaggagggag aagaggagca aagcgacaac ccctactact tcgacgaacg aagcttaagt 780
acaaggttca ggaccgagga aggccacatc tcagttctgg agaacttcta tggtagatcc 840
aagcttctac gcgcactaaa aaactatcgc ttggtgctcc tcgaggctaa ccccaacgcc 900
ttcgtgctcc ctacccactt ggatgcagat gccattctct tggtcatagg agggagagga 960
gccctcaaaa tgatccacca cgacaacaga gaatcctaca acctcgagtg tggagacgta 1020
atcagaatcc cagctggaac cacattctac ttaatcaacc gagacaacaa cgagaggctc 1080
cacatagcca agttcttaca gaccatatcc actcctggcc aatacaagga attcttccca 1140
gctggaggcc aaaacccaga gccgtacctc agtaccttca gcaaagagat tctcgaggct 1200
gcgctcaaca cacaaacaga gaagctgcgt ggggtgtttg gacagcaaag ggagggagtg 1260
ataattaggg cgtcacagga gcagatcagg gagttgactc gagatgactc agagtcacga 1320

-continued cactggcata taaggagagg tggtgaatca agcaggggac cttacaatct gttcaacaaa 1380
aggccactgt actccaacaa atacggtcaa gcctacgaag tcaaacctga ggactacagg 1440
caactccaag acatggactt atcggttttc atagccaacg tcacccaggg atccatgatg 1500
ggtcccttct tcaacactag gtctacaaag gtggtagtgg tggctagtgg agaggcagat 1560
gtggaaatgg catgccctca cttgtcggga agacacggcg gccgcggtgg aggaaaaagg 1620
catgaggagg aagaggatgt gcactatgag caggttagag cacgtttgtc gaagagagag 1680
gccattgttg ttctggcagg tcatcccgtc gtcttcgttt catccggaaa cgagaacctg 1740
ctgctttttg catttggaat caatgcccaa aacaaccacg agaacttcct cgcggggaga 1800
gagaggaacg tgctgcagca gatagagcca caggcaatgg agctagcgtt tgccgctcca 1860
aggaaagagg tagaagagtc atttaacagc caggaccagt ctatcttctt tcctgggccc 1920
aggcagcacc agcaacagtc gccccgctcc accaagcaac aacagcctct cgtctccatt 1980
ctggacttcg ttggcttcta aagttccaca aaaaagagtg tgttatgtag tataggttag 2040
tagctcctag ctcggtgtat gagagtggta agagactaag acgctaaatc cctaagtaac 2100
taacctggcg agcttgcgtg tatgcaaata aagaggaaca gctttccaac tttaaaaaaa 2160
aaaaaaaaaa a 2171

<210> SEQ ID NO 3
<211> LENGTH: 666
<212> TYPE: PRT
<213> ORGANISM: Macadamia integrifolia
<220> FEATURE:
<221> NAME/KEY: SIGNAL
<222> LOCATION: (1)...(28)
<221> NAME/KEY: PEPTIDE
<222> LOCATION: (29)...(666)

<400> SEQUENCE: 3

Met Ala Ile Asn Thr Ser Asn Leu Cys Ser Leu Leu Phe Leu Leu Ser
1 5 10 15

Leu Phe Leu Leu Ser Thr Thr Val Ser Leu Ala Glu Ser Glu Phe Asp
20 25 30

Arg Gln Glu Tyr Glu Glu Cys Lys Arg Gln Cys Met Gln Leu Glu Thr
35 40 45

Ser Gly Gln Met Arg Arg Cys Val Ser Gln Cys Asp Lys Arg Phe Glu
50 55 60

Glu Asp Ile Asp Trp Ser Lys Tyr Asp Asn Gln Asp Asp Pro Gln Thr
65 70 75 80

Asp Cys Gln Gln Cys Gln Arg Arg Cys Arg Gln Gln Glu Ser Gly Pro
85 90 95

Arg Gln Gln Gln Tyr Cys Gln Arg Arg Cys Lys Glu Ile Cys Glu Glu
100 105 110

Glu Glu Glu Tyr Asn Arg Gln Arg Asp Pro Gln Gln Gln Tyr Glu Gln
115 120 125

Cys Gln Glu Arg Cys Gln Arg His Glu Thr Glu Pro Arg His Met Gln
130 135 140

Thr Cys Gln Gln Arg Cys Glu Arg Arg Tyr Glu Lys Glu Lys Arg Lys
145 150 155 160

Gln Gln Lys Arg Tyr Glu Glu Gln Gln Arg Glu Asp Glu Glu Lys Tyr
165 170 175

Glu Glu Arg Met Lys Glu Glu Asp Asn Lys Arg Asp Pro Gln Gln Arg
180 185 190

-continued

```
Glu Tyr Glu Asp Cys Arg Arg Arg Cys Glu Gln Gln Glu Pro Arg Gln
        195                 200                 205

Gln Tyr Gln Cys Gln Arg Arg Cys Arg Glu Gln Gln Arg Gln His Gly
    210                 215                 220

Arg Gly Gly Asp Leu Ile Asn Pro Gln Arg Gly Gly Ser Gly Arg Tyr
225                 230                 235                 240

Glu Glu Gly Glu Glu Lys Gln Ser Asp Asn Pro Tyr Tyr Phe Asp Glu
                245                 250                 255

Arg Ser Leu Ser Thr Arg Phe Arg Thr Glu Glu Gly His Ile Ser Val
            260                 265                 270

Leu Glu Asn Phe Tyr Gly Arg Ser Lys Leu Leu Arg Ala Leu Lys Asn
        275                 280                 285

Tyr Arg Leu Val Leu Leu Glu Ala Asn Pro Asn Ala Phe Val Leu Pro
    290                 295                 300

Thr His Leu Asp Ala Asp Ala Ile Leu Leu Val Thr Gly Gly Arg Gly
305                 310                 315                 320

Ala Leu Lys Met Ile His Arg Asp Asn Arg Glu Ser Tyr Asn Leu Glu
                325                 330                 335

Cys Gly Asp Val Ile Arg Ile Pro Ala Gly Thr Thr Phe Tyr Leu Ile
            340                 345                 350

Asn Arg Asp Asn Asn Glu Arg Leu His Ile Ala Lys Phe Leu Gln Thr
        355                 360                 365

Ile Ser Thr Pro Gly Gln Tyr Lys Glu Phe Phe Pro Ala Gly Gly Gln
    370                 375                 380

Asn Pro Glu Pro Tyr Leu Ser Thr Phe Ser Lys Glu Ile Leu Glu Ala
385                 390                 395                 400

Ala Leu Asn Thr Gln Ala Glu Arg Leu Arg Gly Val Leu Gly Gln Gln
                405                 410                 415

Arg Glu Gly Val Ile Ile Ser Ala Ser Gln Glu Gln Ile Arg Glu Leu
            420                 425                 430

Thr Arg Asp Asp Ser Glu Ser Arg Arg Trp His Ile Arg Arg Gly Gly
        435                 440                 445

Glu Ser Ser Arg Gly Pro Tyr Asn Leu Phe Asn Lys Arg Pro Leu Tyr
    450                 455                 460

Ser Asn Lys Tyr Gly Gln Ala Tyr Glu Val Lys Pro Glu Asp Tyr Arg
465                 470                 475                 480

Gln Leu Gln Asp Met Asp Val Ser Val Phe Ile Ala Asn Ile Thr Gln
                485                 490                 495

Gly Ser Met Met Gly Pro Phe Phe Asn Thr Arg Ser Thr Lys Val Val
            500                 505                 510

Val Val Ala Ser Gly Glu Ala Asp Val Glu Met Ala Cys Pro His Leu
        515                 520                 525

Ser Gly Arg His Gly Gly Arg Arg Gly Gly Lys Arg His Glu Glu Glu
    530                 535                 540

Glu Asp Val His Tyr Glu Gln Val Lys Ala Arg Leu Ser Lys Arg Glu
545                 550                 555                 560

Ala Ile Val Val Pro Val Gly His Pro Val Val Phe Val Ser Ser Gly
                565                 570                 575

Asn Glu Asn Leu Leu Leu Phe Ala Phe Gly Ile Asn Ala Gln Asn Asn
            580                 585                 590

His Glu Asn Phe Leu Ala Gly Arg Glu Arg Asn Val Leu Gln Gln Ile
        595                 600                 605
```

-continued

```
Glu Pro Gln Ala Met Glu Leu Ala Phe Ala Ala Pro Arg Lys Glu Val
    610                 615                 620

Glu Glu Leu Phe Asn Ser Gln Asp Glu Ser Ile Phe Phe Pro Gly Pro
625                 630                 635                 640

Arg Gln His Gln Gln Gln Ser Ser Arg Ser Thr Lys Gln Gln Gln Pro
                645                 650                 655

Leu Val Ser Ile Leu Asp Phe Val Gly Phe
            660                 665


<210> SEQ ID NO 4
<211> LENGTH: 2171
<212> TYPE: DNA
<213> ORGANISM: Macadamia integrifolia
<220> FEATURE:
<221> NAME/KEY: sig_peptide
<222> LOCATION: (1)...(86)
<221> NAME/KEY: mat_peptide
<222> LOCATION: (87)...(1999)

<400> SEQUENCE: 4

atggcgatca atacatcaaa tttatgttct cttctctttc tcctttccct cttccttctg     60

tcaacgacag tgtctcttgc tgaaagtgaa tttgacaggc aggaatatga ggagtgcaaa    120

cggcaatgca tgcagttgga gacatcaggc cagatgcgtc ggtgtgtgag tcagtgcgat    180

aagagatttg aagaggatat agattggtct aagtatgata accaagacga tcctcagacg    240

gattgccaac aatgccagag gcgatgcagg cagcaggaga gtggcccacg tcagcaacaa    300

tactgccaac gacgctgcaa ggaaatatgt gaagaagaag aagaatataa ccgacaacgt    360

gatccacagc agcaatacga gcaatgtcag gagcgctgcc aacggcacga gacagagcca    420

cgtcacatgc aaacatgtca acaacgctgc gagaggagat atgaaaagga gaaacgtaag    480

caacaaaaga gatatgaaga gcaacaacgt gaagacgaag agaaatatga agagcgaatg    540

aaggaagaag ataacaaacg cgatccacaa caaagagagt acgaagactg ccggaggcgc    600

tgcgaacaac aggagccacg tcagcagtac cagtgccagc gaagatgccg agagcagcag    660

aggcaacacg gccgaggtgg tgatttgatt aaccctcaga ggggaggcag cggcagatac    720

gaggagggag aagagaagca aagcgacaac ccctactact tcgacgaacg aagcttaagt    780

acaaggttca ggaccgagga aggccacatc tcagttctgg agaacttcta tggtagatcc    840

aagcttctac gcgcactaaa aaactatcgc ttggtgctcc tcgaggctaa ccccaacgcc    900

ttcgtgctcc ctacccactt ggacgcagat gccattctct tggtcaccgg agggagagga    960

gccctcaaaa tgatccaccg tgacaacaga gaatcctaca acctcgagtg tggagacgta   1020

atcagaatcc cagctggaac cacattctac ttaatcaacc gagacaacaa cgagaggctc   1080

cacatagcca agttcttaca gaccatatcc actcctggcc aatacaagga attcttccca   1140

gctggaggcc aaaacccaga gccgtacctc agtaccttca gcaaagagat tctcgaggct   1200

gcgctcaaca cacaagcaga gaggctgcgt ggggtgcttg gacagcaaag ggagggagtg   1260

ataattagtg cgtcacagga gcagatcagg gagttgactc gagatgactc agagtcacga   1320

cgctggcata taaggagagg tggtgaatca agcaggggac cttacaatct gttcaacaaa   1380

aggccactgt actccaacaa atacggtcaa gcctacgaag tcaaacctga ggactacagg   1440

caactccaag acatggacgt atcggttttc atagccaaca tcacccaggg atccatgatg   1500

ggtcccttct tcaacactag gtctacaaag gtggtagtgg tggctagtgg agaggcagat   1560

gtggaaatgg catgccctca cttgtcggga agacacggcg gccgccgtgg agggaaaagg   1620
```

-continued

```
catgaggagg aagaggatgt gcactatgag caggttaaag cacgtttgtc gaagagagag   1680

gccattgttg ttccggtagg tcatcccgtc gtcttcgttt catccggaaa cgagaacctg   1740

ctgctttttg catttggaat caatgcccaa aacaaccacg agaacttcct cgcggggaga   1800

gagaggaacg tgctgcagca gatagagcca caggcaatgg agctagcgtt tgccgctcca   1860

aggaaagagg tagaagagtt atttaacagc caggacgagt ctatcttctt tcctgggccc   1920

aggcagcacc agcaacagtc ttcccgctcc accaagcaac aacagcctct cgtctccatt   1980

ctggacttcg ttggcttcta aagttctaca aaaaagagtg tgttatgtag tataggttag   2040

tagctcctag ctcggtgtat gcgagtggta agagaccaag acgctaaatc cctaagtaac   2100

taacctggcg agcttgcgtg tatgcaaata aagaggaaca gctttccaac tttaaaaaaa   2160

aaaaaaaaaa a                                                        2171
```

```
<210> SEQ ID NO 5
<211> LENGTH: 625
<212> TYPE: PRT
<213> ORGANISM: Macadamia integrifolia
<220> FEATURE:
<221> NAME/KEY: PEPTIDE
<222> LOCATION: (1)...(625)
<223> OTHER INFORMATION: Partial mature peptide

<400> SEQUENCE: 5

Gln Cys Met Gln Leu Glu Thr Ser Gly Gln Met Arg Arg Cys Val Ser
 1               5                  10                  15

Gln Cys Asp Lys Arg Phe Glu Glu Asp Ile Asp Trp Ser Lys Tyr Asp
            20                  25                  30

Asn Gln Glu Asp Pro Gln Thr Glu Cys Gln Gln Cys Gln Arg Arg Cys
        35                  40                  45

Arg Gln Gln Glu Ser Asp Pro Arg Gln Gln Gln Tyr Cys Gln Arg Arg
    50                  55                  60

Cys Lys Glu Ile Cys Glu Glu Glu Glu Glu Tyr Asn Arg Gln Arg Asp
65                  70                  75                  80

Pro Gln Gln Gln Tyr Glu Gln Cys Gln Lys Arg Cys Gln Arg Arg Glu
                85                  90                  95

Thr Glu Pro Arg His Met Gln Ile Cys Gln Gln Arg Cys Glu Arg Arg
            100                 105                 110

Tyr Glu Lys Glu Lys Arg Lys Gln Gln Lys Arg Tyr Glu Glu Gln Gln
        115                 120                 125

Arg Glu Asp Glu Glu Lys Tyr Glu Glu Arg Met Lys Glu Gly Asp Asn
    130                 135                 140

Lys Arg Asp Pro Gln Gln Arg Glu Tyr Glu Asp Cys Arg Arg His Cys
145                 150                 155                 160

Glu Gln Gln Glu Pro Arg Leu Gln Tyr Gln Cys Gln Arg Arg Cys Gln
                165                 170                 175

Glu Gln Gln Arg Gln His Gly Arg Gly Gly Asp Leu Met Asn Pro Gln
            180                 185                 190

Arg Gly Gly Ser Gly Arg Tyr Glu Glu Gly Glu Glu Lys Gln Ser Asp
        195                 200                 205

Asn Pro Tyr Tyr Phe Asp Glu Arg Ser Leu Ser Thr Arg Phe Arg Thr
    210                 215                 220

Glu Glu Gly His Ile Ser Val Leu Glu Asn Phe Tyr Gly Arg Ser Lys
225                 230                 235                 240

Leu Leu Arg Ala Leu Lys Asn Tyr Arg Leu Val Leu Leu Glu Ala Asn
                245                 250                 255
```

-continued

```
Pro Asn Ala Phe Val Leu Pro Thr His Leu Asp Ala Asp Ala Ile Leu
            260                 265                 270

Leu Val Ile Gly Gly Arg Gly Ala Leu Lys Met Ile His Arg Asp Asn
        275                 280                 285

Arg Glu Ser Tyr Asn Leu Glu Cys Gly Asp Val Ile Arg Ile Pro Ala
    290                 295                 300

Gly Thr Thr Phe Tyr Leu Ile Asn Arg Asp Asn Asn Glu Arg Leu His
305                 310                 315                 320

Ile Ala Lys Phe Leu Gln Thr Ile Ser Thr Pro Gly Gln Tyr Lys Glu
                325                 330                 335

Phe Phe Pro Ala Gly Gly Gln Asn Pro Glu Pro Tyr Leu Ser Thr Phe
            340                 345                 350

Ser Lys Glu Ile Leu Glu Ala Ala Leu Asn Thr Gln Thr Glu Arg Leu
        355                 360                 365

Arg Gly Val Leu Gly Gln Gln Arg Glu Gly Val Ile Ile Arg Ala Ser
    370                 375                 380

Gln Glu Gln Ile Arg Glu Leu Thr Arg Asp Asp Ser Glu Ser Arg Arg
385                 390                 395                 400

Trp His Ile Arg Arg Gly Gly Glu Ser Ser Arg Gly Pro Tyr Asn Leu
                405                 410                 415

Phe Asn Lys Arg Pro Leu Tyr Ser Asn Lys Tyr Gly Gln Ala Tyr Glu
            420                 425                 430

Val Lys Pro Glu Asp Tyr Arg Gln Leu Gln Asp Met Asp Val Ser Val
        435                 440                 445

Phe Ile Ala Asn Ile Thr Gln Gly Ser Met Met Gly Pro Phe Phe Asn
    450                 455                 460

Thr Arg Ser Thr Lys Val Val Val Val Ala Ser Gly Glu Ala Asp Val
465                 470                 475                 480

Glu Met Ala Cys Pro His Leu Ser Gly Arg His Gly Gly Arg Gly Gly
                485                 490                 495

Gly Lys Arg His Glu Glu Glu Glu Glu Val His Tyr Glu Gln Val Arg
            500                 505                 510

Ala Arg Leu Ser Lys Arg Glu Ala Ile Val Val Leu Ala Gly His Pro
        515                 520                 525

Val Val Phe Val Ser Ser Gly Asn Glu Asn Leu Leu Leu Phe Ala Phe
    530                 535                 540

Gly Ile Asn Ala Gln Asn Asn His Glu Asn Phe Leu Ala Gly Arg Glu
545                 550                 555                 560

Arg Asn Val Leu Gln Gln Ile Glu Pro Gln Ala Met Glu Leu Ala Phe
                565                 570                 575

Ala Ala Ser Arg Lys Glu Val Glu Glu Leu Phe Asn Ser Gln Asp Glu
            580                 585                 590

Ser Ile Phe Phe Pro Gly Pro Arg Gln His Gln Gln Gln Ser Pro Arg
        595                 600                 605

Ser Thr Lys Gln Gln Gln Pro Leu Val Ser Ile Leu Asp Phe Val Gly
    610                 615                 620

Phe
625


<210> SEQ ID NO 6
<211> LENGTH: 2140
<212> TYPE: DNA
<213> ORGANISM: Macadamia integrifolia
<220> FEATURE:
```

-continued

<221> NAME/KEY: mat_peptide
<222> LOCATION: (1)...(1875)
<223> OTHER INFORMATION: partial mature peptide

<400> SEQUENCE: 6

```
caatgcatgc agttagagac atcaggccag atgcgtcggt gtgtgagtca gtgcgataag     60
agatttgaag aggatataga ttggtctaag tatgataacc aagaggatcc tcagacggaa    120
tgccaacaat gccagaggcg atgcaggcag caggagagtg acccacgtca gcaacaatac    180
tgccaacgac gctgcaagga aatatgtgaa gaagaagaag aatataaccg acaacgtgat    240
ccacagcagc aatacgagca atgtcagaag cgctgccaac ggcgcgagac agagccacgt    300
cacatgcaaa tatgtcaaca acgctgcgag aggagatatg aaaaggagaa acgtaagcaa    360
caaaagagat atgaagagca acaacgtgaa gacgaagaga aatatgaaga gcgaatgaag    420
gaaggagata acaaacgcga tccacaacaa agagagtacg aagactgccg gcggcactgc    480
gaacaacagg agccacgtct gcagtaccag tgccagcgaa gatgccaaga gcagcagagg    540
caacacggcc gaggtggcga tttgatgaac cctcagaggg gaggcagcgg cagatacgag    600
gagggagaag agaagcaaag cgacaacccc tactacttcg acgaacgaag cttaagtaca    660
aggttcagga ccgaggaagg ccacatctca gttctggaga acttctatgg tagatccaag    720
cttctacgcg cactaaaaaa ctatcgcttg gtgctcctcg aggctaaccc caacgccttc    780
gtgctcccta cccacttgga tgcagatgcc attctcttgg tcatcggagg gagaggagcc    840
ctcaaaatga tccaccgtga caacagagaa tcctacaacc tcgagtgtgg agacgtaatc    900
agaatcccag ctggaaccac attctactta atcaaccgag acaacaacga gaggctccac    960
atagccaagt tcttacagac catatccact cctggccaat acaaggaatt cttcccagct   1020
ggaggccaaa acccagagcc gtacctcagt accttcagca aagagattct cgaggctgcg   1080
ctcaacacac aaacagagag gctgcgtggg gtgcttggac agcaaaggga gggagtgata   1140
attagggcgt cacaggagca gatcagggag ttgactcgag atgactcaga gtcacgacgc   1200
tggcatataa ggagaggtgg tgaatcaagc aggggacctt acaatctgtt caacaaaagg   1260
ccactgtact ccaacaaata cggtcaagcc tacgaagtca aacctgagga ctacaggcaa   1320
ctccaagaca tggacgtatc agttttcata gccaacatca cccagggatc catgatgggt   1380
cccttcttca acactaggtc tacaaaggtg gtagtggtgg ctagtggaga ggcagatgtg   1440
gaaatggcat gccctcactt gtcgggaaga cacggcggcc gcggtggagg gaaaaggcat   1500
gaggaggaag aggaggtgca ctatgagcag gttagagcac gtttgtcgaa gagagaggcc   1560
attgttgttc tggcaggtca tcccgtcgtc ttcgtttcat ccggaaacga aaacctgctg   1620
ctttttgcat ttggaatcaa tgcccaaaac aaccacgaga acttcctcgc ggggagagag   1680
aggaacgtgc tgcagcagat agagccacag gcaatggagc tagcgtttgc cgcttcaagg   1740
aaagaggtag aagagttatt taacagccag gacgagtcta tcttctttcc tgggcccagg   1800
cagcaccagc aacagtcgcc ccgctccacc aagcaacaac agcctctcgt ctccattctg   1860
gacttcgttg gcttctaaag ttctacaaaa aagagtgtgt tatgtagtat aggttagtag   1920
ctcctagctc ggtgtatgag agtggtaaga gactaagacg ctaaatccct aagtaactaa   1980
cctggcgagc ttgcgtgtat gcaaataaag aggaacagct ttccaacttt agaaagctct   2040
ttttttttt tttttcttt ctttttctta agaaataaac gaacgtagat tgcggctcaa   2100
aaaaaaaaaa aaaaaaaaaa aaaaaaaaaa aaaaaaaaaa                          2140
```

-continued

<210> SEQ ID NO 7
<211> LENGTH: 525
<212> TYPE: PRT
<213> ORGANISM: Theobroma cacao

<400> SEQUENCE: 7

```
Met Val Ile Ser Lys Ser Pro Phe Ile Val Leu Ile Phe Ser Leu Leu
 1               5                  10                  15

Leu Ser Phe Ala Leu Leu Cys Ser Gly Val Ser Ala Tyr Gly Arg Lys
            20                  25                  30

Gln Tyr Glu Arg Asp Pro Arg Gln Gln Tyr Glu Gln Cys Gln Arg Arg
        35                  40                  45

Cys Glu Ser Glu Ala Thr Glu Glu Arg Glu Gln Glu Gln Cys Glu Gln
    50                  55                  60

Arg Cys Glu Arg Glu Tyr Lys Glu Gln Gln Arg Gln Gln Glu Glu Glu
65                  70                  75                  80

Leu Gln Arg Gln Tyr Gln Gln Cys Gln Gly Arg Cys Gln Glu Gln Gln
                85                  90                  95

Gln Gly Gln Arg Glu Gln Gln Gln Cys Gln Arg Lys Cys Trp Glu Gln
            100                 105                 110

Tyr Lys Glu Gln Glu Arg Gly Glu His Glu Asn Tyr His Asn His Lys
        115                 120                 125

Lys Asn Arg Ser Glu Glu Glu Glu Gly Gln Gln Arg Asn Asn Pro Tyr
    130                 135                 140

Tyr Phe Pro Lys Arg Arg Ser Phe Gln Thr Arg Phe Arg Asp Glu Glu
145                 150                 155                 160

Gly Asn Phe Lys Ile Leu Gln Arg Phe Ala Glu Asn Ser Pro Pro Leu
                165                 170                 175

Lys Gly Ile Asn Asp Tyr Arg Leu Ala Met Phe Glu Ala Asn Pro Asn
            180                 185                 190

Thr Phe Ile Leu Pro His His Cys Asp Ala Glu Ala Ile Tyr Phe Val
        195                 200                 205

Thr Asn Gly Lys Gly Thr Ile Thr Phe Val Thr His Glu Asn Lys Glu
    210                 215                 220

Ser Tyr Asn Val Gln Arg Gly Thr Val Val Ser Val Pro Ala Gly Ser
225                 230                 235                 240

Thr Val Tyr Val Val Ser Gln Asp Asn Gln Glu Lys Leu Thr Ile Ala
                245                 250                 255

Val Leu Ala Leu Pro Val Asn Ser Pro Gly Lys Tyr Glu Leu Phe Phe
            260                 265                 270

Pro Ala Gly Asn Asn Lys Pro Glu Ser Tyr Tyr Gly Ala Phe Ser Tyr
        275                 280                 285

Glu Val Leu Glu Thr Val Phe Asn Thr Gln Arg Glu Lys Leu Glu Glu
    290                 295                 300

Ile Leu Glu Glu Gln Arg Gly Gln Lys Arg Gln Gln Gly Gln Gln Gly
305                 310                 315                 320

Met Phe Arg Lys Ala Lys Pro Glu Gln Ile Arg Ala Ile Ser Gln Gln
                325                 330                 335

Ala Thr Ser Pro Arg His Arg Gly Gly Glu Arg Leu Ala Ile Asn Leu
            340                 345                 350

Leu Ser Gln Ser Pro Val Tyr Ser Asn Gln Asn Gly Arg Phe Phe Glu
        355                 360                 365

Ala Cys Pro Glu Asp Phe Ser Gln Phe Gln Asn Met Asp Val Ala Val
    370                 375                 380
```

-continued

```
Ser Ala Phe Lys Leu Asn Gln Gly Ala Ile Phe Val Pro His Tyr Asn
385                 390                 395                 400

Ser Lys Ala Thr Phe Val Val Phe Val Thr Asp Gly Tyr Gly Tyr Ala
                405                 410                 415

Gln Met Ala Cys Pro His Leu Ser Arg Gln Ser Gln Gly Ser Gln Ser
            420                 425                 430

Gly Arg Gln Asp Arg Arg Glu Gln Glu Glu Glu Ser Glu Glu Glu Thr
        435                 440                 445

Phe Gly Glu Phe Gln Gln Val Lys Ala Pro Leu Ser Pro Gly Asp Val
    450                 455                 460

Phe Val Ala Pro Ala Gly His Ala Val Thr Phe Phe Ala Ser Lys Asp
465                 470                 475                 480

Gln Pro Leu Asn Ala Val Ala Phe Gly Leu Asn Ala Gln Asn Asn Gln
                485                 490                 495

Arg Ile Phe Leu Ala Gly Arg Pro Phe Phe Leu Asn His Lys Gln Asn
            500                 505                 510

Thr Asn Val Ile Lys Phe Thr Val Lys Ala Ser Ala Tyr
        515                 520                 525


<210> SEQ ID NO 8
<211> LENGTH: 590
<212> TYPE: PRT
<213> ORGANISM: Gossypium hirsutum (cotton)

<400> SEQUENCE: 8

Met Val Arg Asn Lys Ser Ala Cys Val Val Leu Leu Phe Ser Leu Phe
 1               5                  10                  15

Leu Ser Phe Gly Leu Leu Cys Ser Ala Lys Asp Phe Pro Gly Arg Arg
            20                  25                  30

Gly Asp Asp Asp Pro Pro Lys Arg Tyr Glu Asp Cys Arg Arg Arg Cys
        35                  40                  45

Glu Trp Asp Thr Arg Gly Gln Lys Glu Gln Gln Gln Cys Glu Glu Ser
    50                  55                  60

Cys Lys Ser Gln Tyr Gly Glu Lys Asp Gln Gln Gln Arg His Arg Pro
65                  70                  75                  80

Glu Asp Pro Gln Arg Arg Tyr Glu Glu Cys Gln Gln Glu Cys Arg Gln
                85                  90                  95

Gln Glu Glu Arg Gln Gln Pro Gln Cys Gln Gln Arg Cys Leu Lys Arg
            100                 105                 110

Phe Glu Gln Glu Gln Gln Gln Ser Gln Arg Gln Phe Gln Glu Cys Gln
        115                 120                 125

Gln His Cys His Gln Gln Glu Gln Arg Pro Glu Lys Lys Gln Gln Cys
    130                 135                 140

Val Arg Glu Cys Arg Glu Lys Tyr Gln Glu Asn Pro Trp Arg Gly Glu
145                 150                 155                 160

Arg Glu Glu Glu Ala Glu Glu Glu Glu Thr Glu Glu Gly Glu Gln Glu
                165                 170                 175

Gln Ser His Asn Pro Phe His Phe His Arg Arg Ser Phe Gln Ser Arg
            180                 185                 190

Phe Arg Glu Glu His Gly Asn Phe Arg Val Leu Gln Arg Phe Ala Ser
        195                 200                 205

Arg His Pro Ile Leu Arg Gly Ile Asn Glu Phe Arg Leu Ser Ile Leu
    210                 215                 220

Glu Ala Asn Pro Asn Thr Phe Val Leu Pro His His Cys Asp Ala Glu
225                 230                 235                 240
```

-continued

```
Lys Ile Tyr Leu Val Thr Asn Gly Arg Gly Thr Leu Thr Phe Leu Thr
                245                 250                 255

His Glu Asn Lys Glu Ser Tyr Asn Ile Val Pro Gly Val Val Val Lys
            260                 265                 270

Val Pro Ala Gly Ser Thr Val Tyr Leu Ala Asn Gln Asp Asn Lys Glu
        275                 280                 285

Lys Leu Ile Ile Ala Val Leu His Arg Pro Val Asn Asn Pro Gly Gln
    290                 295                 300

Phe Glu Glu Phe Phe Pro Ala Gly Ser Gln Arg Pro Gln Ser Tyr Leu
305                 310                 315                 320

Arg Ala Phe Ser Arg Glu Ile Leu Glu Pro Ala Phe Asn Thr Arg Ser
                325                 330                 335

Glu Gln Leu Asp Glu Leu Phe Gly Gly Arg Gln Ser Arg Arg Arg Gln
            340                 345                 350

Gln Gly Gln Gly Met Phe Arg Lys Ala Ser Gln Glu Gln Ile Arg Ala
        355                 360                 365

Leu Ser Gln Glu Ala Thr Ser Pro Arg Glu Lys Ser Gly Glu Arg Phe
    370                 375                 380

Ala Phe Asn Leu Leu Ser Gln Thr Pro Arg Tyr Ser Asn Gln Asn Gly
385                 390                 395                 400

Arg Phe Phe Glu Ala Cys Pro Pro Glu Phe Arg Gln Leu Arg Asp Ile
                405                 410                 415

Asn Val Thr Val Ser Ala Leu Gln Leu Asn Gln Gly Ser Ile Phe Val
            420                 425                 430

Pro His Tyr Asn Ser Lys Ala Thr Phe Val Ile Leu Val Thr Glu Gly
        435                 440                 445

Asn Gly Tyr Ala Glu Met Val Ser Pro His Leu Pro Arg Gln Ser Ser
    450                 455                 460

Tyr Glu Glu Glu Glu Glu Glu Asp Glu Glu Glu Glu Gln Glu Gln Glu
465                 470                 475                 480

Glu Glu Arg Arg Ser Gly Gln Tyr Arg Lys Ile Arg Ser Arg Leu Ser
                485                 490                 495

Arg Gly Asp Ile Phe Val Val Pro Ala Asn Phe Pro Val Thr Phe Val
            500                 505                 510

Ala Ser Gln Asn Gln Asn Leu Arg Met Thr Gly Phe Gly Leu Tyr Asn
        515                 520                 525

Gln Asn Ile Asn Pro Asp His Asn Gln Arg Ile Phe Val Ala Gly Lys
    530                 535                 540

Ile Asn His Val Arg Gln Trp Asp Ser Gln Ala Lys Glu Leu Ala Phe
545                 550                 555                 560

Gly Val Ser Ser Arg Leu Val Asp Glu Ile Phe Asn Ser Asn Pro Gln
                565                 570                 575

Glu Ser Tyr Phe Val Ser Arg Gln Arg Gln Arg Ala Ser Glu
            580                 585                 590
```

<210> SEQ ID NO 9
<211> LENGTH: 22
<212> TYPE: PRT
<213> ORGANISM: Artificial Sequence
<220> FEATURE:
<223> OTHER INFORMATION: Peptide 1 from M. integrifolia MiAMP2c in which Cys is replaced with Ala and Tyr is replaced with Ala, MiAMP2cpep1.

<400> SEQUENCE: 9

-continued

```
Arg Gln Arg Asp Pro Gln Gln Gln Ala Glu Gln Ala Gln Lys Arg Ala
 1              5                   10                  15

Gln Arg Arg Glu Thr Glu
            20


<210> SEQ ID NO 10
<211> LENGTH: 25
<212> TYPE: PRT
<213> ORGANISM: Artificial Sequence
<220> FEATURE:
<223> OTHER INFORMATION: Peptide 2 from M. integrifolia MiAMP2c,
      MiAMPcpep2.

<400> SEQUENCE: 10

Pro Arg His Met Gln Ile Ala Gln Gln Arg Ala Glu Arg Arg Ala Glu
 1              5                   10                  15

Lys Glu Lys Arg Lys Gln Gln Lys Arg
            20                  25


<210> SEQ ID NO 11
<211> LENGTH: 36
<212> TYPE: PRT
<213> ORGANISM: Artificial Sequence
<220> FEATURE:
<223> OTHER INFORMATION: Synthetic DNA sequence coding for a leader
      peptide.

<400> SEQUENCE: 11

Ser Glu Gln Ile Asp Asn Met Ala Trp Phe His Val Ser Val Cys Asn
 1              5                   10                  15

Ala Val Phe Val Val Ile Ile Ile Ile Met Leu Leu Met Phe Val Pro
            20                  25                  30

Val Val Arg Gly
        35


<210> SEQ ID NO 12
<211> LENGTH: 20
<212> TYPE: DNA
<213> ORGANISM: Artificial Sequence
<220> FEATURE:
<223> OTHER INFORMATION: Primer JPM17 which binds to M. integrifolia
      MiAMP2c.

<400> SEQUENCE: 12

cagcagcagt atgagcagtg                                                  20


<210> SEQ ID NO 13
<211> LENGTH: 21
<212> TYPE: DNA
<213> ORGANISM: Artificial Sequence
<220> FEATURE:
<223> OTHER INFORMATION: Primer JMP20, a degenerate primer that binds to
      MiAMP2-like sequences.

<400> SEQUENCE: 13

tttttcgtak ckkckttcgc a                                                21


<210> SEQ ID NO 14
<211> LENGTH: 24
<212> TYPE: DNA
<213> ORGANISM: Artificial Sequence
<220> FEATURE:
<223> OTHER INFORMATION: Primer JPM31 corresponding to the 5' coding
      region of MiAMP2c and containing Nde1 and BamH1 sites.

<400> SEQUENCE: 14
```

-continued acaccatatg cgacaacgtg atcc 24

<210> SEQ ID NO 15
<211> LENGTH: 26
<212> TYPE: DNA
<213> ORGANISM: Artificial Sequence
<220> FEATURE:
<223> OTHER INFORMATION: Primer JPM32 corresponding to the 3' coding region of MiAMP2c and containing Nde1 and BamH1 sites.

<400> SEQUENCE: 15
cgttgttttc tctattccta gggttg 26

<210> SEQ ID NO 16
<211> LENGTH: 22
<212> TYPE: PRT
<213> ORGANISM: Artificial Sequence
<220> FEATURE:
<223> OTHER INFORMATION: Peptide containing His tag and Factor Xa cleavage site of PET16b vector.

<400> SEQUENCE: 16

Met Gly His His His His His His His His His His Ser Ser Gly His
1 5 10 15

Ile Glu Gly Arg His Met
20

<210> SEQ ID NO 17
<211> LENGTH: 90
<212> TYPE: DNA
<213> ORGANISM: Artificial Sequence
<220> FEATURE:
<223> OTHER INFORMATION: TcAMP1 forward oligonucleotide.

<400> SEQUENCE: 17
gggaattcca tatgtatgag cgtgatcctc gacagcaata cgagcaatgc cagaggcgat 60
gcgagtcgga agcgactgaa gaaagggagc 90

<210> SEQ ID NO 18
<211> LENGTH: 91
<212> TYPE: DNA
<213> ORGANISM: Artificial Sequence
<220> FEATURE:
<223> OTHER INFORMATION: TcAMP1 reverse oligonucleotide.

<400> SEQUENCE: 18
gaagcgactg aagaaaggga gcaagagcag tgtgaacaac gctgtgaaag ggagtacaag 60
gagcagcaga gacagcaata gggatccaca c 91

<210> SEQ ID NO 19
<211> LENGTH: 101
<212> TYPE: DNA
<213> ORGANISM: Artificial Sequence
<220> FEATURE:
<223> OTHER INFORMATION: TcAMP2 forward oligonucleotide.

<400> SEQUENCE: 19
gggaattcca tatgcttcaa aggcaatacc agcaatgtca agggcgttgt caagagcaac 60
aacaggggca gagagagcag cagcagtgcc agagaaaatg c 101

<210> SEQ ID NO 20
<211> LENGTH: 102
<212> TYPE: DNA

-continued

<213> ORGANISM: Artificial Sequence
<220> FEATURE:
<223> OTHER INFORMATION: TcAMP2 reverse oligonucleotide.

<400> SEQUENCE: 20
gtgtggatcc ctagctccta ttttttttgt gattatggta attctcgtgc tcgcctctct 60
cttgttcctt atattgctcc cagcattttc tctggcactg ct 102

<210> SEQ ID NO 21
<211> LENGTH: 614
<212> TYPE: PRT
<213> ORGANISM: Peanut

<400> SEQUENCE: 21

Met Arg Gly Arg Val Ser Pro Leu Met Leu Leu Leu Gly Ile Leu Val
1 5 10 15

Leu Ala Ser Val Ser Ala Thr Gln Ala Lys Ser Pro Tyr Arg Lys Thr
20 25 30

Glu Asn Pro Cys Ala Gln Arg Cys Leu Gln Ser Cys Gln Gln Glu Pro
35 40 45

Asp Asp Leu Lys Gln Lys Ala Cys Glu Ser Arg Cys Thr Lys Leu Glu
50 55 60

Tyr Asp Pro Arg Cys Val Tyr Asp Thr Gly Ala Thr Asn Gln Arg His
65 70 75 80

Pro Pro Gly Glu Arg Thr Arg Gly Arg Gln Pro Gly Asp Tyr Asp Asp
85 90 95

Asp Arg Arg Gln Pro Arg Arg Glu Glu Gly Gly Arg Trp Gly Pro Ala
100 105 110

Glu Pro Arg Glu Arg Glu Arg Glu Glu Asp Trp Arg Gln Pro Arg Glu
115 120 125

Asp Trp Arg Arg Pro Ser His Gln Gln Pro Arg Lys Ile Arg Pro Glu
130 135 140

Gly Arg Glu Gly Glu Gln Glu Trp Gly Thr Pro Gly Ser Glu Val Arg
145 150 155 160

Glu Glu Thr Ser Arg Asn Asn Pro Phe Tyr Phe Pro Ser Arg Arg Phe
165 170 175

Ser Thr Arg Tyr Gly Asn Gln Asn Gly Arg Ile Arg Val Leu Gln Arg
180 185 190

Phe Asp Gln Arg Ser Lys Gln Phe Gln Asn Leu Gln Asn His Arg Ile
195 200 205

Val Gln Ile Glu Ala Arg Pro Asn Thr Leu Val Leu Pro Lys His Ala
210 215 220

Asp Ala Asp Asn Ile Leu Val Ile Gln Gln Gly Gln Ala Thr Val Thr
225 230 235 240

Val Ala Asn Gly Asn Asn Arg Lys Ser Phe Asn Leu Asp Glu Gly His
245 250 255

Ala Leu Arg Ile Pro Ser Gly Phe Ile Ser Tyr Ile Leu Asn Arg His
260 265 270

Asp Asn Gln Asn Leu Arg Val Ala Lys Ile Ser Met Pro Val Asn Thr
275 280 285

Pro Gly Gln Phe Glu Asp Phe Phe Pro Ala Ser Ser Arg Asp Gln Ser
290 295 300

Ser Tyr Leu Gln Gly Phe Ser Arg Asn Thr Leu Glu Ala Ala Phe Asn
305 310 315 320

Ala Glu Phe Asn Glu Ile Arg Arg Val Leu Leu Glu Glu Asn Ala Gly

-continued

```
                325                 330                 335

Gly Glu Gln Glu Glu Arg Gly Gln Arg Arg Arg Ser Thr Arg Ser Ser
            340                 345                 350

Asp Asn Glu Gly Val Ile Val Lys Val Ser Lys Glu His Val Gln Glu
        355                 360                 365

Leu Thr Lys His Ala Lys Ser Val Ser Lys Lys Gly Ser Glu Glu Glu
    370                 375                 380

Asp Ile Thr Asn Pro Ile Asn Leu Arg Asp Gly Glu Pro Asp Leu Ser
385                 390                 395                 400

Asn Asn Phe Gly Arg Leu Phe Glu Val Lys Pro Asp Lys Lys Asn Pro
                405                 410                 415

Gln Leu Gln Asp Leu Asp Met Met Leu Thr Cys Val Glu Ile Lys Glu
            420                 425                 430

Gly Ala Leu Met Leu Pro His Phe Asn Ser Lys Ala Met Val Ile Val
        435                 440                 445

Val Val Asn Lys Gly Thr Gly Asn Leu Glu Leu Val Ala Val Arg Lys
    450                 455                 460

Glu Gln Gln Gln Arg Gly Arg Arg Glu Gln Glu Trp Glu Glu Glu Glu
465                 470                 475                 480

Glu Asp Glu Glu Glu Glu Gly Ser Asn Arg Glu Val Arg Arg Tyr Thr
                485                 490                 495

Ala Arg Leu Lys Glu Gly Asp Val Phe Ile Met Pro Ala Ala His Pro
            500                 505                 510

Val Ala Ile Asn Ala Ser Ser Glu Leu His Leu Leu Gly Phe Gly Ile
        515                 520                 525

Asn Ala Glu Asn Asn His Arg Ile Phe Leu Ala Gly Asp Lys Asp Asn
    530                 535                 540

Val Ile Asp Gln Ile Glu Lys Gln Ala Lys Asp Leu Ala Phe Pro Gly
545                 550                 555                 560

Ser Gly Glu Gln Val Glu Lys Leu Ile Lys Asn Gln Arg Glu Ser His
                565                 570                 575

Phe Val Ser Ala Arg Pro Gln Ser Gln Ser Pro Ser Ser Pro Glu Lys
            580                 585                 590

Glu Asp Gln Glu Glu Glu Asn Gln Gly Gly Lys Gly Pro Leu Leu Ser
        595                 600                 605

Ile Leu Lys Ala Phe Asn
    610


<210> SEQ ID NO 22
<211> LENGTH: 582
<212> TYPE: PRT
<213> ORGANISM: Maize

<400> SEQUENCE: 22

Met Val Ser Ala Arg Ile Val Val Leu Leu Ala Thr Leu Leu Cys Ala
 1               5                  10                  15

Ala Ala Ala Val Ala Ser Ser Trp Glu Asp Asp Asn His His His His
            20                  25                  30

Gly Gly His Lys Ser Gly Gln Cys Val Arg Arg Cys Glu Asp Arg Pro
        35                  40                  45

Trp His Gln Arg Pro Arg Cys Leu Glu Gln Cys Arg Glu Glu Glu Arg
    50                  55                  60

Glu Lys Arg Gln Glu Arg Ser Arg His Glu Ala Asp Asp Arg Ser Gly
65                  70                  75                  80
```

-continued

```
Glu Gly Ser Ser Glu Asp Glu Arg Glu Gln Glu Lys Glu Lys Gln Lys
                85                  90                  95

Asp Arg Arg Pro Tyr Val Phe Asp Arg Arg Ser Phe Arg Arg Val Val
            100                 105                 110

Arg Ser Glu Gln Gly Ser Leu Arg Val Leu Arg Pro Phe Asp Glu Val
        115                 120                 125

Ser Arg Leu Leu Arg Gly Ile Arg Asp Tyr Arg Val Ala Val Leu Glu
    130                 135                 140

Ala Asn Pro Arg Ser Phe Val Val Pro Ser His Thr Asp Ala His Cys
145                 150                 155                 160

Ile Cys Tyr Val Ala Glu Gly Glu Gly Val Val Thr Thr Ile Glu Asn
                165                 170                 175

Gly Glu Arg Arg Ser Tyr Thr Ile Lys Gln Gly His Val Phe Val Ala
            180                 185                 190

Pro Ala Gly Ala Val Thr Tyr Leu Ala Asn Thr Asp Gly Arg Lys Lys
        195                 200                 205

Leu Val Ile Thr Lys Ile Leu His Thr Ile Ser Val Pro Gly Glu Phe
    210                 215                 220

Gln Phe Phe Phe Gly Pro Gly Gly Arg Asn Pro Glu Ser Phe Leu Ser
225                 230                 235                 240

Ser Phe Ser Lys Ser Ile Gln Arg Ala Ala Tyr Lys Thr Ser Ser Asp
                245                 250                 255

Arg Leu Glu Arg Leu Phe Gly Arg His Gly Gln Asp Lys Gly Ile Ile
            260                 265                 270

Val Arg Ala Thr Glu Glu Gln Thr Arg Glu Leu Arg Arg His Ala Ser
        275                 280                 285

Glu Gly Gly His Gly Pro His Trp Pro Leu Pro Pro Phe Gly Glu Ser
    290                 295                 300

Arg Gly Pro Tyr Ser Leu Leu Asp Gln Arg Pro Ser Ile Ala Asn Gln
305                 310                 315                 320

His Gly Gln Leu Tyr Glu Ala Asp Ala Arg Ser Phe His Asp Leu Ala
                325                 330                 335

Glu His Asp Val Ser Val Ser Phe Ala Asn Ile Thr Ala Gly Ser Met
            340                 345                 350

Ser Ala Pro Leu Phe Asn Thr Arg Ser Phe Lys Ile Ala Tyr Val Pro
        355                 360                 365

Asn Gly Lys Gly Tyr Ala Glu Ile Val Cys Pro His Arg Gln Ser Gln
    370                 375                 380

Gly Gly Glu Ser Glu Arg Glu Arg Asp Lys Gly Arg Arg Ser Glu Glu
385                 390                 395                 400

Glu Glu Glu Glu Ser Ser Glu Glu Gln Glu Glu Ala Gly Gln Gly Tyr
                405                 410                 415

His Thr Ile Arg Ala Arg Leu Ser Pro Gly Thr Ala Phe Val Val Pro
            420                 425                 430

Ala Gly His Pro Phe Val Ala Val Ala Ser Arg Asp Ser Asn Leu Gln
        435                 440                 445

Ile Val Cys Phe Glu Val His Ala Asp Arg Asn Glu Lys Val Phe Leu
    450                 455                 460

Ala Gly Ala Asp Asn Val Leu Gln Lys Leu Asp Arg Val Ala Lys Ala
465                 470                 475                 480

Leu Ser Phe Ala Ser Lys Ala Glu Glu Val Asp Glu Val Leu Gly Ser
                485                 490                 495

Arg Arg Glu Lys Gly Phe Leu Pro Gly Pro Glu Glu Ser Gly Gly His
```

-continued

```
            500                 505                 510

Glu Glu Arg Glu Gln Glu Glu Glu Glu Arg Glu Glu Arg His Gly Gly
        515                 520                 525

Arg Gly Glu Arg Glu Arg His Gly Arg Glu Glu Arg Glu Lys Glu Glu
    530                 535                 540

Glu Arg Glu Gly Arg His Gly Gly Arg Glu Glu Arg Glu Glu Glu Glu
545                 550                 555                 560

Arg His Gly Arg Gly Arg Arg Glu Glu Val Ala Glu Thr Leu Met Arg
                565                 570                 575

Met Val Thr Ala Arg Met
            580


<210> SEQ ID NO 23
<211> LENGTH: 33
<212> TYPE: PRT
<213> ORGANISM: Maize

<400> SEQUENCE: 23

Arg Ser Gly Arg Gly Glu Cys Arg Arg Gln Cys Leu Arg Arg His Glu
 1               5                  10                  15

Gly Gln Pro Trp Glu Thr Gln Glu Cys Met Arg Arg Cys Arg Arg Arg
            20                  25                  30

Gly


<210> SEQ ID NO 24
<211> LENGTH: 637
<212> TYPE: PRT
<213> ORGANISM: Barley

<400> SEQUENCE: 24

Met Ala Thr Arg Ala Lys Ala Thr Ile Pro Leu Leu Phe Leu Leu Gly
 1               5                  10                  15

Thr Ser Leu Leu Phe Ala Ala Ala Val Ser Ala Ser His Asp Asp Glu
            20                  25                  30

Asp Asp Arg Arg Gly Gly His Ser Leu Gln Gln Cys Val Gln Arg Cys
        35                  40                  45

Arg Gln Glu Arg Pro Arg Tyr Ser His Ala Arg Cys Val Gln Glu Cys
    50                  55                  60

Arg Asp Asp Gln Gln Gln His Gly Arg His Glu Gln Glu Glu Glu Gln
65                  70                  75                  80

Gly Arg Gly Arg Gly Trp His Gly Glu Gly Glu Arg Glu Glu Glu His
                85                  90                  95

Gly Arg Gly Arg Gly Arg His Gly Glu Gly Glu Arg Glu Glu Glu His
            100                 105                 110

Gly Arg Gly Arg Gly Arg His Gly Glu Gly Glu Arg Glu Glu Glu Arg
        115                 120                 125

Gly Arg Gly His Gly Arg His Gly Glu Gly Glu Arg Glu Glu Glu Arg
    130                 135                 140

Gly Arg Gly Arg Gly Arg His Gly Glu Gly Glu Arg Glu Glu Glu Glu
145                 150                 155                 160

Gly Arg Gly Arg Gly Arg Arg Gly Glu Gly Glu Arg Asp Glu Glu Gln
                165                 170                 175

Gly Asp Ser Arg Arg Pro Tyr Val Phe Gly Pro Arg Ser Phe Arg Arg
            180                 185                 190

Ile Ile Gln Ser Asp His Gly Phe Val Arg Ala Leu Arg Pro Phe Asp
        195                 200                 205
```

-continued

Gln Val Ser Arg Leu Leu Arg Gly Ile Arg Asp Tyr Arg Val Ala Ile
    210                 215                 220

Met Glu Val Asn Pro Arg Ala Phe Val Val Pro Gly Phe Thr Asp Ala
225                 230                 235                 240

Asp Gly Val Gly Tyr Val Ala Gln Gly Glu Gly Val Leu Thr Val Ile
                245                 250                 255

Glu Asn Gly Glu Lys Arg Ser Tyr Thr Val Lys Glu Gly Asp Val Ile
            260                 265                 270

Val Ala Pro Ala Gly Ser Ile Met His Leu Ala Asn Thr Asp Gly Arg
        275                 280                 285

Arg Lys Leu Val Ile Ala Lys Ile Leu His Thr Ile Ser Val Pro Gly
    290                 295                 300

Lys Phe Gln Phe Leu Ser Val Lys Pro Leu Leu Ala Ser Leu Ser Lys
305                 310                 315                 320

Arg Val Leu Arg Ala Ala Phe Lys Thr Ser Asp Glu Arg Leu Glu Arg
                325                 330                 335

Leu Phe Asn Gln Arg Gln Gly Gln Glu Lys Thr Arg Ser Val Ser Ile
            340                 345                 350

Val Arg Ala Ser Glu Glu Gln Leu Arg Glu Leu Arg Arg Glu Ala Ala
        355                 360                 365

Glu Gly Gly Gln Gly His Arg Trp Pro Leu Pro Pro Phe Arg Gly Asp
    370                 375                 380

Ser Arg Asp Thr Phe Asn Leu Leu Glu Gln Arg Pro Lys Ile Ala Asn
385                 390                 395                 400

Arg His Gly Arg Leu Tyr Glu Ala Asp Ala Arg Ser Phe His Ala Leu
                405                 410                 415

Ala Asn Gln Asp Val Arg Val Ala Val Ala Asn Ile Thr Pro Gly Ser
            420                 425                 430

Met Thr Ala Pro Tyr Leu Asn Thr Gln Ser Phe Lys Leu Ala Val Val
        435                 440                 445

Leu Glu Gly Glu Gly Glu Val Gln Ile Val Cys Pro His Leu Gly Arg
    450                 455                 460

Glu Ser Glu Ser Glu Arg Glu His Gly Lys Gly Arg Arg Arg Glu Glu
465                 470                 475                 480

Glu Glu Asp Asp Gln Arg Gln Gln Arg Arg Arg Gly Ser Glu Ser Glu
                485                 490                 495

Ser Glu Glu Glu Glu Glu Gln Gln Arg Tyr Glu Thr Val Arg Ala Arg
            500                 505                 510

Val Ser Arg Gly Ser Ala Phe Val Val Pro Pro Gly His Pro Val Val
        515                 520                 525

Glu Ile Ser Ser Ser Gln Gly Ser Ser Asn Leu Gln Val Val Cys Phe
    530                 535                 540

Glu Ile Asn Ala Glu Arg Asn Glu Arg Val Trp Leu Ala Gly Arg Asn
545                 550                 555                 560

Asn Val Ile Gly Lys Leu Gly Ser Pro Ala Gln Glu Leu Thr Phe Gly
                565                 570                 575

Arg Pro Ala Arg Glu Val Gln Glu Val Phe Arg Ala Gln Asp Gln Asp
            580                 585                 590

Glu Gly Phe Val Ala Gly Pro Glu Gln Gln Ser Arg Glu Gln Glu Gln
        595                 600                 605

Glu Gln Glu Arg His Arg Arg Arg Gly Asp Arg Gly Arg Gly Asp Glu
    610                 615                 620

-continued

```
Ala Val Glu Thr Phe Leu Arg Met Ala Thr Gly Ala Ile
625                 630                 635
```

<210> SEQ ID NO 25
<211> LENGTH: 605
<212> TYPE: PRT
<213> ORGANISM: Soybean (Glycine max)

<400> SEQUENCE: 25

```
Met Met Arg Ala Arg Phe Pro Leu Leu Leu Leu Gly Leu Val Phe Leu
 1               5                  10                  15

Ala Ser Val Ser Val Ser Phe Gly Ile Ala Tyr Trp Glu Lys Glu Asn
            20                  25                  30

Pro Lys His Asn Lys Cys Leu Gln Ser Cys Asn Ser Glu Arg Asp Ser
        35                  40                  45

Tyr Arg Asn Gln Ala Cys His Ala Arg Cys Asn Leu Leu Lys Val Glu
    50                  55                  60

Lys Glu Glu Cys Glu Glu Gly Glu Ile Pro Arg Pro Arg Pro Arg Pro
65                  70                  75                  80

Gln His Pro Glu Arg Glu Pro Gln Gln Pro Gly Glu Lys Glu Glu Asp
                85                  90                  95

Glu Asp Glu Gln Pro Arg Pro Ile Pro Phe Pro Arg Pro Gln Pro Arg
            100                 105                 110

Gln Glu Glu Glu His Glu Gln Arg Glu Glu Gln Glu Trp Pro Arg Lys
        115                 120                 125

Glu Glu Lys Arg Gly Glu Lys Gly Ser Glu Glu Glu Asp Glu Asp Glu
    130                 135                 140

Asp Glu Glu Gln Asp Glu Arg Gln Phe Pro Phe Pro Arg Pro Pro His
145                 150                 155                 160

Gln Lys Glu Glu Arg Asn Glu Glu Glu Asp Glu Asp Glu Glu Gln Gln
                165                 170                 175

Arg Glu Ser Glu Glu Ser Glu Asp Ser Glu Leu Arg Arg His Lys Asn
            180                 185                 190

Lys Asn Pro Phe Leu Phe Gly Ser Asn Arg Phe Glu Thr Leu Phe Lys
        195                 200                 205

Asn Gln Tyr Gly Arg Ile Arg Val Leu Gln Arg Phe Asn Gln Arg Ser
    210                 215                 220

Pro Gln Leu Gln Asn Leu Arg Asp Tyr Arg Ile Leu Glu Phe Asn Ser
225                 230                 235                 240

Lys Pro Asn Thr Leu Leu Leu Pro Asn His Ala Asp Ala Asp Tyr Leu
                245                 250                 255

Ile Val Ile Leu Asn Gly Thr Ala Ile Leu Ser Leu Val Asn Asn Asp
            260                 265                 270

Asp Arg Asp Ser Tyr Arg Leu Gln Ser Gly Asp Ala Leu Arg Val Pro
        275                 280                 285

Ser Gly Thr Thr Tyr Tyr Val Val Asn Pro Asp Asn Asn Glu Asn Leu
    290                 295                 300

Arg Leu Ile Thr Leu Ala Ile Pro Val Asn Lys Pro Gly Arg Phe Glu
305                 310                 315                 320

Ser Phe Phe Leu Ser Ser Thr Glu Ala Gln Gln Ser Tyr Leu Gln Gly
                325                 330                 335

Phe Ser Arg Asn Ile Leu Glu Ala Ser Tyr Asp Thr Lys Phe Glu Glu
            340                 345                 350

Ile Asn Lys Val Leu Phe Ser Arg Glu Glu Gly Gln Gln Gln Gly Glu
        355                 360                 365
```

-continued

```
Gln Arg Leu Gln Glu Ser Val Ile Val Glu Ile Ser Lys Glu Gln Ile
    370                 375                 380

Arg Ala Leu Ser Lys Arg Ala Lys Ser Ser Ser Arg Lys Thr Ile Ser
385                 390                 395                 400

Ser Glu Asp Lys Pro Phe Asn Leu Arg Ser Arg Asp Pro Ile Tyr Ser
                405                 410                 415

Asn Lys Leu Gly Lys Phe Phe Glu Ile Thr Pro Glu Lys Asn Pro Gln
            420                 425                 430

Leu Arg Asp Leu Asp Ile Phe Leu Ser Ile Val Asp Met Asn Glu Gly
        435                 440                 445

Ala Leu Leu Leu Pro His Phe Asn Ser Lys Ala Ile Val Ile Leu Val
    450                 455                 460

Ile Asn Glu Gly Asp Ala Asn Ile Glu Leu Val Gly Leu Lys Glu Gln
465                 470                 475                 480

Gln Gln Glu Gln Gln Gln Glu Glu Gln Pro Leu Glu Val Arg Lys Tyr
                485                 490                 495

Arg Ala Glu Leu Ser Glu Gln Asp Ile Phe Val Ile Pro Ala Gly Tyr
            500                 505                 510

Pro Val Val Val Asn Ala Thr Ser Asn Leu Asn Phe Phe Ala Ile Gly
        515                 520                 525

Ile Asn Ala Glu Asn Asn Gln Arg Asn Phe Leu Ala Gly Ser Gln Asp
    530                 535                 540

Asn Val Ile Ser Gln Ile Pro Ser Gln Val Gln Glu Leu Ala Phe Pro
545                 550                 555                 560

Gly Ser Ala Gln Ala Val Glu Lys Leu Leu Lys Asn Gln Arg Glu Ser
                565                 570                 575

Tyr Phe Val Asp Ala Gln Pro Lys Lys Lys Glu Glu Gly Asn Lys Gly
            580                 585                 590

Arg Lys Gly Pro Leu Ser Ser Ile Leu Arg Ala Phe Tyr
        595                 600                 605


<210> SEQ ID NO 26
<211> LENGTH: 23
<212> TYPE: PRT
<213> ORGANISM: Stenocarpus sinuatus
<220> FEATURE:
<221> NAME/KEY: PEPTIDE
<222> LOCATION: (1)...(23)
<223> OTHER INFORMATION: Partial MiAMP2c homologous peptide.

<400> SEQUENCE: 26

Val Lys Glu Asp His Gln Phe Glu Thr Arg Gly Glu Ile Leu Glu Cys
 1               5                  10                  15

Tyr Arg Leu Cys Gln Gln Gln
            20


<210> SEQ ID NO 27
<211> LENGTH: 17
<212> TYPE: PRT
<213> ORGANISM: Stenocarpus sinuatus
<220> FEATURE:
<221> NAME/KEY: PEPTIDE
<222> LOCATION: (1)...(27)
<223> OTHER INFORMATION: Partial MiAMP2c homologous peptide.

<400> SEQUENCE: 27

Gln Lys His Arg Ser Gln Ile Leu Gly Cys Tyr Leu Xaa Cys Gln Gln Leu
 1               5                  10                  15
```

-continued

<210> SEQ ID NO 28
<211> LENGTH: 28
<212> TYPE: PRT
<213> ORGANISM: Stenocarpus sinuatus
<220> FEATURE:
<221> NAME/KEY: PEPTIDE
<222> LOCATION: (1)...(28)
<223> OTHER INFORMATION: Partial MiAMP2c homologous peptide.

<400> SEQUENCE: 28

Leu Asp Pro Ile Arg Gln Gln Gln Leu Cys Gln Met Arg Cys Gln Gln
1 5 10 15

Gln Glu Lys Asp Pro Arg Gln Gln Gln Gln Cys Lys
20 25

<210> SEQ ID NO 29
<211> LENGTH: 368
<212> TYPE: DNA
<213> ORGANISM: Artificial Sequence
<220> FEATURE:
<223> OTHER INFORMATION: A synthetic nucleotide sequence which can be used for the expression and secretion of MiAMP2c, containing the leader sequence from SEQ ID NO:11 and SEQ ID NO:5.
<221> NAME/KEY: CDS
<222> LOCATION: (103)...(333)

<400> SEQUENCE: 29
aactctagag cggccgcgtc gactattttt acaacaatta ccaacaacaa caaacaacaa 60
acaacattac aattactatt tacaattaca ggatccacaa ca atg gct tgg ttc 114
Met Ala Trp Phe
1 cac gtt tct gtt tgt aac gct gtt ttc gtt gtt att att att att atg 162
His Val Ser Val Cys Asn Ala Val Phe Val Val Ile Ile Ile Ile Met
5 10 15 20 ctt ctt atg ttc gtt cct gtt gtt aga ggt aga caa aga gat cct caa 210
Leu Leu Met Phe Val Pro Val Val Arg Gly Arg Gln Arg Asp Pro Gln
25 30 35 caa caa tac gag caa tgt caa aag agg tgt caa agg aga gag act gag 258
Gln Gln Tyr Glu Gln Cys Gln Lys Arg Cys Gln Arg Arg Glu Thr Glu
40 45 50 cct aga cac atg caa att tgt cag caa agg tgt gaa agg agg tac gag 306
Pro Arg His Met Gln Ile Cys Gln Gln Arg Cys Glu Arg Arg Tyr Glu
55 60 65 aag gag aag agg aag caa caa aag agg tgaggatccg tcgacgcggc 353
Lys Glu Lys Arg Lys Gln Gln Lys Arg
70 75 cgcagatcta gacaa 368

<210> SEQ ID NO 30
<211> LENGTH: 77
<212> TYPE: PRT
<213> ORGANISM: Artificial Sequence
<220> FEATURE:
<223> OTHER INFORMATION: A synthetic peptide sequence which can be used for the expression and secretion of MiAMP2c containing the leader sequence from SEQ ID NO:11 and peptide sequence from SEQ ID NO:5.

<400> SEQUENCE: 30

Met Ala Trp Phe His Val Ser Val Cys Asn Ala Val Phe Val Val Ile
1 5 10 15

Ile Ile Ile Met Leu Leu Met Phe Val Pro Val Val Arg Gly Arg Gln
20 25 30

Arg Asp Pro Gln Gln Gln Tyr Glu Gln Cys Gln Lys Arg Cys Gln Arg

-continued

```
        35                  40                  45

Arg Glu Thr Glu Pro Arg His Met Gln Ile Cys Gln Gln Arg Cys Glu
    50                  55                  60

Arg Arg Tyr Glu Lys Glu Lys Arg Lys Gln Gln Lys Arg
65                  70                  75


<210> SEQ ID NO 31
<211> LENGTH: 27
<212> TYPE: PRT
<213> ORGANISM: Artificial Sequence
<220> FEATURE:
<223> OTHER INFORMATION: Consensus sequence for antimicrobial peptides
      wherein X is any amino acid.

<400> SEQUENCE: 31

Cys Xaa Xaa Cys Xaa Xaa Xaa Cys Xaa Xaa Xaa Xaa Xaa Xaa Xaa Xaa
 1               5                  10                  15

Xaa Xaa Cys Xaa Xaa Xaa Cys Xaa Xaa Xaa Cys
            20                  25


<210> SEQ ID NO 32
<211> LENGTH: 28
<212> TYPE: PRT
<213> ORGANISM: Artificial Sequence
<220> FEATURE:
<223> OTHER INFORMATION: Consensus sequence for antimicrobial peptides
      wherein X is any amino acid.

<400> SEQUENCE: 32

Cys Xaa Xaa Cys Xaa Xaa Xaa Cys Xaa Xaa Xaa Xaa Xaa Xaa Xaa Xaa
 1               5                  10                  15

Xaa Xaa Xaa Cys Xaa Xaa Xaa Cys Xaa Xaa Xaa Cys
            20                  25


<210> SEQ ID NO 33
<211> LENGTH: 29
<212> TYPE: PRT
<213> ORGANISM: Artificial Sequence
<220> FEATURE:
<223> OTHER INFORMATION: Consensus sequence for antimicrobial peptides
      wherein X is any amino acid.

<400> SEQUENCE: 33

Cys Xaa Xaa Cys Xaa Xaa Xaa Cys Xaa Xaa Xaa Xaa Xaa Xaa Xaa Xaa
 1               5                  10                  15

Xaa Xaa Xaa Xaa Cys Xaa Xaa Xaa Cys Xaa Xaa Xaa Cys
            20                  25


<210> SEQ ID NO 34
<211> LENGTH: 27
<212> TYPE: PRT
<213> ORGANISM: Artificial Sequence
<220> FEATURE:
<223> OTHER INFORMATION: Consensus sequence for antimicrobial peptides,
      wherein X is any amino acid and  the first and
      last X are Phenylalanine or Tyrosine.

<400> SEQUENCE: 34

Xaa Xaa Xaa Cys Xaa Xaa Xaa Cys Xaa Xaa Xaa Xaa Xaa Xaa Xaa Xaa
 1               5                  10                  15

Xaa Xaa Cys Xaa Xaa Xaa Cys Xaa Xaa Xaa Xaa
            20                  25


<210> SEQ ID NO 35
```

-continued

<211> LENGTH: 28
<212> TYPE: PRT
<213> ORGANISM: Artificial Sequence
<220> FEATURE:
<223> OTHER INFORMATION: Consensus sequence for antimicrobial peptides wherein X is any amino acid and the first and last X are phenylalanine or Tyrosine.

<400> SEQUENCE: 35

Xaa Xaa Xaa Cys Xaa Xaa Xaa Cys Xaa Xaa Xaa Xaa Xaa Xaa Xaa Xaa
1 5 10 15

Xaa Xaa Xaa Cys Xaa Xaa Xaa Cys Xaa Xaa Xaa Xaa
20 25

<210> SEQ ID NO 36
<211> LENGTH: 29
<212> TYPE: PRT
<213> ORGANISM: Artificial Sequence
<220> FEATURE:
<223> OTHER INFORMATION: Consensus sequence for antimicrobial peptides wherein X is any amino acid and the first and last X are phenylalanine or Tyrosine.

<400> SEQUENCE: 36

Xaa Xaa Xaa Cys Xaa Xaa Xaa Cys Xaa Xaa Xaa Xaa Xaa Xaa Xaa Xaa
1 5 10 15

Xaa Xaa Xaa Xaa Cys Xaa Xaa Xaa Cys Xaa Xaa Xaa Xaa
20 25

<210> SEQ ID NO 37
<211> LENGTH: 20
<212> TYPE: PRT
<213> ORGANISM: Artificial Sequence
<220> FEATURE:
<223> OTHER INFORMATION: Consensus sequence for antimicrobial peptides wherein X is any amino acid.

<400> SEQUENCE: 37

Cys Xaa Xaa Xaa Cys Xaa Xaa Xaa Xaa Xaa Xaa Xaa Xaa Xaa Xaa Cys
1 5 10 15

Xaa Xaa Xaa Cys
20

<210> SEQ ID NO 38
<211> LENGTH: 21
<212> TYPE: PRT
<213> ORGANISM: Artificial Sequence
<220> FEATURE:
<223> OTHER INFORMATION: Consensus sequence for antimicrobial peptides wherein X is any amino acid.

<400> SEQUENCE: 38

Cys Xaa Xaa Xaa Cys Xaa Xaa Xaa Xaa Xaa Xaa Xaa Xaa Xaa Xaa Xaa
1 5 10 15

Cys Xaa Xaa Xaa Cys
20

<210> SEQ ID NO 39
<211> LENGTH: 22
<212> TYPE: PRT
<213> ORGANISM: Artificial Sequence
<220> FEATURE:
<223> OTHER INFORMATION: Consensus sequence for antimicrobial peptides wherein X is any amino acid.

<400> SEQUENCE: 39

-continued

```
Cys Xaa Xaa Xaa Cys Xaa Xaa Xaa Xaa Xaa Xaa Xaa Xaa Xaa Xaa Xaa
 1               5                  10                  15

Xaa Cys Xaa Xaa Xaa Cys
            20


<210> SEQ ID NO 40
<211> LENGTH: 5
<212> TYPE: PRT
<213> ORGANISM: Artificial Sequence
<220> FEATURE:
<223> OTHER INFORMATION: Consensus sequence for antimicrobial peptides
      wherein X is any amino acid.

<400> SEQUENCE: 40

Cys Xaa Xaa Xaa Cys
 1               5
```